(12) United States Patent
Lundy et al.

(10) Patent No.: US 6,531,492 B1
(45) Date of Patent: Mar. 11, 2003

(54) HETEROCYCLO-ALKYLSULFONYL PYRAZOLE DERIVATIVES AS ANTI-INFLAMMATORY/ANALGESIC AGENTS

(75) Inventors: Kristin M. Lundy, Groton, CT (US); Hengmiao Cheng, East Lyme, CT (US); Subas M. Sakya, East Lyme, CT (US); Jin Li, Pawcatuck, CT (US); Martha L. Minich, Gales Ferry, CT (US); Chikara Uchida, Chita-gun (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/724,446

(22) Filed: Nov. 28, 2000

Related U.S. Application Data
(60) Provisional application No. 60/168,701, filed on Dec. 3, 1999.

(51) Int. Cl.⁷ .................. C07D 401/04; A61K 31/4439
(52) U.S. Cl. ..................... 514/341; 546/275.4
(58) Field of Search ................. 546/275.4; 514/341

(56) References Cited

FOREIGN PATENT DOCUMENTS

| | | |
|---|---|---|
| EP | 418845 | 3/1991 |
| EP | 554829 | 6/1994 |
| WO | 9500501 | 4/1995 |
| WO | 9515315 | 6/1995 |
| WO | 9515316 | 6/1995 |
| WO | 9515317 | 6/1995 |
| WO | 9515318 | 6/1995 |
| WO | 9603387 | 2/1996 |
| WO | 9603392 | 2/1996 |
| WO | 9608482 | 3/1996 |
| WO | 9619469 | 6/1996 |
| WO | 9636623 | 11/1996 |
| WO | 9711704 | 4/1997 |
| WO | 9713755 | 4/1997 |
| WO | 9714691 | 4/1997 |
| WO | 9716435 | 5/1997 |

OTHER PUBLICATIONS

CA 131:5253, Angermann et al. 1999.*
CA 131:307102, Yalamoori et al. 1999.*
Vane, J.R.; Mitchell, J.A.; Appleton, I.; Tomlinson, A.; Bishop–Bailey, D.; Croxtoll, J.; Willoughby, D. A. *Proc. Natl. Acad. Sci. USA*, 1994, 91, 2046.

* cited by examiner

*Primary Examiner*—Jane Fan
(74) *Attorney, Agent, or Firm*—Peter C. Richardson; Gregg C. Benson; B. Timothy Creagan

(57) ABSTRACT

The present invention relates to compounds of the formula

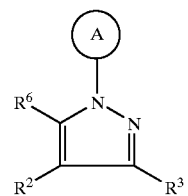

I wherein $R^2$, $R^3$, $R^6$ and A are defined as in the specification, to pharmaceutical compositions containing them and to their medicinal use. The compounds of the invention are useful in the treatment or alleviation of inflammation and other inflammation associated disorders, such as osteoarthritis, rheumatoid arthritis, colon cancer and Alzheimer's disease, in mammals (preferably humans, dogs, cats and livestock).

12 Claims, No Drawings

HETEROCYCLO-ALKYLSULFONYL PYRAZOLE DERIVATIVES AS ANTI-INFLAMMATORY/ANALGESIC AGENTS

This application is a U.S. non-provisional application of U.S. provisional application No. 60/168,701, filed Dec. 3, 1999.

BACKGROUND OF THE INVENTION

This invention relates to heterocyclo-alkylsulfonyl pyrazole derivatives and methods of treatment and pharmaceutical compositions for the treatment of cyclooxygenase mediated diseases. The compounds of this invention inhibit the biosynthesis of prostaglandins by intervention of the action of the enzyme cyclooxygenase on arachidonic acid, and are therefore useful in the treatment or alleviation of inflammation and other inflammation associated disorders, such as arthritis, neurodegeneration and colon cancer, in mammals, preferably humans, dogs, cats or livestock.

Nonsteroidal anti-inflammatory drugs (NSAIDs) are widely used in treating pain and the signs and symptoms of arthritis because of their analgesic and anti-inflammatory activity. It is accepted that common NSAIDs work by blocking the activity of cyclooxygenase (COX), also known as prostaglandin G/H synthase (PGHS), the enzyme that converts arachidonic acid into prostanoids. Prostaglandins, especially prostaglandin $E_2$ ($PGE_2$), which is the predominant eicosanoid detected in inflammation conditions, are mediators of pain, fever and other symptoms associated with inflammation. Inhibition of the biosynthesis of prostaglandins has been a therapeutic target of anti-inflammatory drug discovery. The therapeutic use of conventional NSAIDs is, however, limited due to drug associated side effects, including life threatening ulceration and renal toxicity. An alternative to NSAIDs is the use of corticosteriods, however, long term therapy can also result in severe side effects.

The use of NSAIDs in dogs and cats has been more limited than that in humans, e.g., only three such NSAIDs have been approved by the Food and Drug Administration, Committee on Veterinary Medicine (FDA/CVM), for use in dogs in the United States, i.e., ETOGESIC® (etodolac), ARQUEL® (meclofenamic acid) and RIMADYL® (carprofen). Consequently, there is less experience and knowledge in veterinary medicine about safety and efficacy issues surrounding the use of NSAIDs in dogs. In veterinary medicine, for example, the most common indication for NSAIDs is the treatment of degenerative joint disease (DJD), which in dogs often results from a variety of developmental diseases, e.g., hip dysplasia and osteochondrosis, as well as from traumatic injuries to joints. In addition to the treatment of chronic pain and inflammation, NSAIDs are also useful in dogs for treating post-surgical acute pain, as well as for treating clinical signs associated with osteoarthritis.

Two forms of COX are now known, a constitutive isoform (COX-1) and an inducible isoform (COX-2) of which expression is upregulated at sites of inflammation (Vane, J. R.; Mitchell, J. A.; Appleton, I.; Tomlinson, A.; Bishop-Bailey, D.; Croxtoll, J.; Willoughby, D. A. *Proc. Natl. Acad. Sci. USA*, 1994, 91, 2046). COX-1 is thought to play a physiological role and to be responsible for gastrointestinal and renal protection. On the other hand, COX-2 appears to play a pathological role and is believed to be the predominant isoform present in inflammation conditions. A pathological role for prostaglandins has been implicated in a number of human disease states including rheumatoid arthritis and osteoarthritis, pyrexia, asthma, bone resorption, cardiovascular diseases, dysmenorrhea, premature labour, nephritis, nephrosis, atherosclerosis, hypotension, shock, pain, cancer, and Alzheimer disease. It is believed that compounds that selectively inhibit the biosynthesis of prostaglandins by intervention of the induction phase of the inducible enzyme COX-2 and/or by intervention of the activity of the enzyme COX-2 on arachidonic acid would provide alternate therapy to the use of NSAIDs or corticosteriods in that such compounds would exert anti-inflammatory effects without the adverse side effects associated with COX-1 inhibition.

A variety of sulfonylbenzene compounds which inhibit COX have been disclosed in patent publications (WO 97/16435, WO 97/14691, WO 96/19469, WO 96/36623, WO 96/03392, WO 96/03387, WO 97/727181, WO 96/936617, WO 96/19469, WO 96/08482, WO 95/00501, WO 95/15315, WO 95/15316, WO 95/15317, WO 95/15318, WO 97/13755, EP 0799523, EP 418845, and EP 554829). Especially important is International Publication Number WO 97/11704, which discloses pyrazole compounds substituted by optionally substituted aryl.

SUMMARY OF THE INVENTION

The present invention relates to compounds of the formula

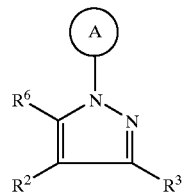

I wherein A is a heterocycle selected from the group consisting of

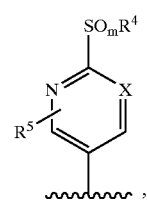

A1

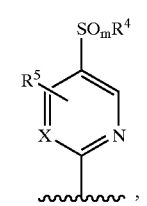

A2

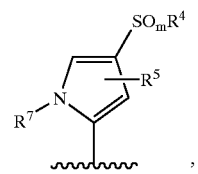

A3

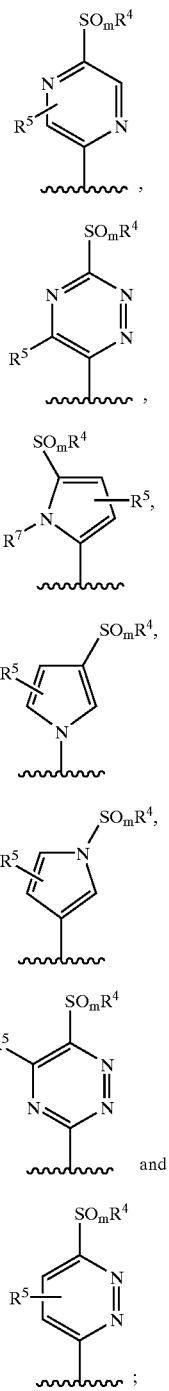

m is 0, 1 or 2;

X is CR⁸ or N;

R² is hydrogen, halo (more preferably chloro or fluoro, most preferably fluoro), $(C_1-C_6)$alkyl, $(C_2-C_6)$alkenyl, $(C_2-C_6)$alkynyl, $(C_1-C_6)$alkoxy, $(C_1-C_6)$alkyl-(C=O)—, formyl, formamidyl, cyano, nitro, HO—(C=O)—, $(C_1-C_6)$alkoxycarbonyl, aminocarbonyl, N—$(C_1-C_6)$alkylaminocarbonyl, N,N—[$(C_1-C_6)$alkyl]₂aminocarbonyl, N—$(C_6-C_{10})$arylaminocarbonyl, N,N—[$(C_6-C_{10})$aryl]₂aminocarbonyl, N—$(C_1-C_6)$alkyl-N—$(C_6-C_{10})$arylaminocarbonyl, $(C_6-C_{10})$aryl, $(C_6-C_{10})$aryloxy, $(C_2-C_9)$heteroaryl, $(C_2-C_9)$heteroaryloxy, morpholinocarbonyl, $(C_1-C_6)$alkoxyaminocarbonyl or $(C_1-C_6)$alkyl-carbonylamino;

wherein said R² $(C_1-C_6)$alkyl group may optionally be substituted with one to three substitutents independently selected from halo, hydroxy, $(C_1-C_6)$alkoxy, cyano, nitro, HO—(C=O)—, $(C_1-C_6)$alkoxycarbonyl, aminocarbonyl, N—$(C_1-C_6)$alkylaminocarbonyl, N,N—[$(C_1-C_6)$alkyl]₂aminocarbonyl, N—$(C_6-C_{10})$arylaminocarbonyl, N,N—[$(C_6-C_{10})$aryl]₂aminocarbonyl, N—$(C_1-C_6)$alkyl-N—$(C_6-C_{10})$arylaminocarbonyl, $(C_6-C_{10})$aryl, $(C_6-C_{10})$aryloxy, $(C_2-C_9)$heteroaryl, $(C_2-C_9)$heteroaryloxy, morpholinocarbonyl, $(C_1-C_6)$alkoxyaminocarbonyl or $(C_1-C_6)$alkyl-carbonylamino;

R³ is hydrogen, halo (more preferably chloro or fluoro, most preferably fluoro), $(C_1-C_6)$alkyl, $(C_2-C_6)$alkenyl, $(C_2-C_6)$alkynyl, $(C_1-C_6)$alkoxy, $(C_1-C_6)$alkyl-(C=O)—, formyl, formamidyl, cyano, nitro, HO—(O=C)—, $(C_1-C_6)$alkoxycarbonyl, aminocarbonyl, N—$(C_1-C_6)$alkylaminocarbonyl, N,N—[$(C_1-C_6)$alkyl]₂aminocarbonyl, N—$(C_6-C_{10})$arylaminocarbonyl, N,N—[$(C_6-C_{10})$aryl]₂aminocarbonyl, N—$(C_1-C_6)$alkyl-N—$(C_6-C_{10})$arylaminocarbonyl, $(C_6-C_{10})$aryl, $(C_6-C_{10})$aryloxy, $(C_2-C_9)$heteroaryl, $(C_2-C_9)$heteroaryloxy, morpholinocarbonyl, $(C_1-C_6)$alkoxyaminocarbonyl or $(C_1-C_6)$alkyl-carbonylamino;

wherein said R³ $(C_1-C_8)$alkyl group may optionally be substituted with one to three substitutents independently selected from halo, hydroxy, $(C_1-C_6)$alkoxy, cyano, nitro, HO—(C=O)—, $(C_1-C_6)$alkoxycarbonyl, aminocarbonyl, N—$(C_1-C_6)$alkylaminocarbonyl, N,N—[$(C_1-C_6)$alkyl]₂aminocarbonyl, N—$(C_6-C_{10})$arylaminocarbonyl, N,N—[$(C_6-C_{10})$aryl]₂aminocarbonyl, N—$(C_1-C_6)$alkyl-N—$(C_6-C_{10})$arylaminocarbonyl, $(C_6-C_{10})$aryl, $(C_6-C_{10})$aryloxy, $(C_2-C_9)$heteroaryl, $(C_2-C_9)$heteroaryloxy, morpholinocarbonyl, $(C_1-C_6)$alkoxyaminocarbonyl or $(C_1-C_6)$alkyl-carbonylamino;

R⁴ is $(C_1-C_6)$alkyl (preferably methyl) optionally substituted by one to three halo atoms (preferably fluoro);

R⁵ is hydrogen; halo (preferably fluoro or chloro); hydroxy; mercapto; $(C_1-C_6)$alkyl; $(C_1-C_6)$alkoxy optionally substituted with one to three halogen atoms (preferably fluoro); $(C_2-C_6)$alkenyl; $(C_2-C_6)$alkynyl; cyano; formyl; $(C_1-C_6)$alkylcarbonyl; $(C_1-C_6)$alkyl-C(=O)—O—; HO—(O=C)—; $(C_1-C_6)$alkoxy-(C=O)—; aminocarbonyl; N—$(C_1-C_6)$alkylaminocarbonyl; N,N—[$(C_1-C_6)$alkyl]₂aminocarbonyl; nitro; amino; $(C_1-C_6)$alkylamino; [$(C_1-C_6)$alkyl]₂amino; or $(C_1-C_6)$alkyl-S—;

wherein said R⁵ $(C_1-C_6)$alkyl group may optionally be substituted with one to three substitutents independently selected from halo, hydroxy, $(C_1-C_6)$alkoxy, cyano, nitro, amino, $(C_1-C_6)$alkylamino, $(C_1-C_6)$dialkylamino, HO—(O=C)—, $(C_1-C_6)$alkoxycarbonyl, aminocarbonyl, N—$(C_1-C_6)$alkylaminocarbonyl, N,N—[$(C_1-C_6)$alkyl]₂aminocarbonyl, N—$(C_6-C_{10})$arylaminocarbonyl, N,N—[$(C_6-C_{10})$aryl]₂aminocarbonyl, N—$(C_1-C_6)$alkyl-N—$(C_6-C_{10})$arylaminocarbonyl, $(C_6-C_{10})$aryl, $(C_6-C_{10})$aryloxy, $(C_2-C_9)$heteroaryl, $(C_2-C_9)$heteroaryloxy, morpholino-carbonyl, $(C_1-C_6)$alkoxyaminocarbonyl or $(C_1-C_6)$alkyl-carbonylamino;

$R^6$ is selected from the group consisting of (a) phenyl optionally substituted by 1–3 substituents independently selected from the group consisting of halo (preferably chloro, bromo or fluoro), hydroxy, cyano, mercapto, HO—(C=O)—, nitro, $(C_1-C_6)$ alkyl, $(C_2-C_6)$alkenyl, $(C_1-C_6)$alkoxy, —OCF$_3$, $(C_1-C_6)$alkyl-S—, $(C_1-C_6)$alkyl-S(=O)—, $(C_1-C_6)$ alkyl-SO$_2$—, amino, $(C_1-C_6)$alkylamino, di[$(C_1-C_8)$alkyl]amino, H$_2$N—(C=O)—, $(C_1-C_6)$ alkyl-NH—(C=O)—, di[$(C_1-C_6)$alkyl]-N—(C=O)—, $(C_1-C_6)$alkyl-(C=O)—O—, $(C_1-C_6)$ alkyl-(C=O)—N(R')—, formyl, $(C_1-C_6)$alkyl-(C=O)—, $(C_1-C_6)$alkoxy-(C=O)—, $(C_6-C_{10})$aryl and $(C_2-C_9)$heterocyclic; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$alkoxy, $(C_1-C_6)$alkyl-S—, $(C_1-C_6)$alkyl-S(=O)—, $(C_1-C_6)$ alkyl-SO$_2$—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)— and $(C_1-C_6)$alkoxy-(C=O)—; wherein R' is hydrogen or $(C_1-C_6)$alkyl;

(b) phenyl fused to a saturated, partially saturated or aromatic (5- to 7-membered)-carbocyclic ring; wherein either of said phenyl or said fused saturated, partially saturated or aromatic (5- to 7-membered)-carbocyclic ring is optionally substituted by 1 to 2 substituents per ring, wherein said substituents are independently selected from the group consisting of halo (preferably chloro, bromo or fluoro), hydroxy, cyano, mercapto, HO—(C=O)—, nitro, $(C_1-C_6)$ alkyl, $(C_2-C_6)$alkenyl, $(C_2-C_6)$alkynyl, $(C_1-C_6)$ alkoxy, —OCF$_3$, $(C_1-C_6)$alkyl-S—, $(C_1-C_6)$alkyl-S(=O)—, $(C_1-C_6)$alkyl-SO$_2$—, amino, $(C_1-C_6)$ alkylamino, di[$(C_1-C_6)$alkyl]amino, H$_2$N—(C=O)—, $(C_1-C_6)$alkyl-NH—(C=O)—, di[$(C_1-C_6)$alkyl]-N—(C=O)—, $(C_1-C_6)$alkyl-(C=O)—O—, $(C_1-C_6)$alkyl-(C=O)—N(R')—, formyl, $(C_1-C_6)$alkyl-(C=O)—, $(C_1-C_6)$alkoxy-(C=O)—, $(C_6-C_{10})$aryl and $(C_2-C_9)$heterocyclic; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$alkoxy, $(C_1-C_6)$alkyl-S—, $(C_1-C_6)$alkyl-S(=O)—, $(C_1-C_6)$alkyl-SO$_2$—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)— and $(C_1-C_6)$alkoxy-(C=O)—; wherein R' is hydrogen or $(C_1-C_6)$alkyl;

(c) phenyl fused to a saturated, partially saturated or aromatic (5- to 6-membered)-heterocyclic ring containing 1 to 2 ring heteroatoms independently selected from the group consisting of —N=, —NR'—, —S— or —O—; wherein either of said phenyl or said fused saturated, partially saturated or aromatic (5- to 6-membered)-heterocyclic ring is optionally substituted with one to two substituents per ring, wherein said substituents are independently selected from the group consisting of halo (preferably chloro, bromo or fluoro), hydroxy, cyano, mercapto, HO—(C=O)—, nitro, $(C_1-C_6)$ alkyl, $(C_2-C_6)$alkenyl, $(C_2-C_6)$alkynyl, $(C_1-C_6)$ alkoxy, —OCF$_3$, $(C_1-C_6)$alkyl-S—, $(C_1-C_6)$alkyl-S(=O)—, $(C_1-C_6)$alkyl-SO$_2$—, amino, $(C_1-C_6)$ alkylamino, di[$(C_1-C_6)$alkyl]amino, H$_2$N—(C=O)—, $(C_1-C_6)$alkyl-NH—(C=O)—, di[$(C_1-C_6)$alkyl]-N—(C=O)—, $(C_1-C_6)$alkyl-(C=O)—O—, $(C_1-C_6)$alkyl-(C=O)—N(R')—, formyl, $(C_1-C_6)$alkyl-(C=O)—, $(C_1-C_6)$alkoxy-(C=O)—, $(C_6-C_{10})$aryl and $(C_2-C_9)$heterocyclic; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$alkoxy, $(C_1-C_6)$alkyl-S—, $(C_1-C_6)$alkyl-S(=O)—, $(C_1-C_6)$alkyl-SO$_2$—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)— and $(C_1-C_6)$alkoxy-(C=O)—; wherein R' is hydrogen or $(C_1-C_6)$alkyl;

(d) (5- to 7-membered)-carbocyclic ring optionally containing one or two double bonds; wherein said (5- to 7-membered)-carbocyclic may also be optionally substituted by 1–3 substituents independently selected from the group consisting of halo (preferably chloro, bromo or fluoro), hydroxy, cyano, mercapto, HO—(C=O)—, nitro, $(C_1-C_6)$ alkyl, $(C_2-C_6)$alkenyl, $(C_2-C_6)$alkynyl, $(C_1-C_6)$ alkoxy, —OCF$_3$, $(C_1-C_6)$alkyl-S—, $(C_1-C_6)$alkyl-S(=O)—, $(C_1-C_6)$alkyl-SO$_2$—, amino, $(C_1-C_6)$ alkylamino, di[$(C_1-C_6)$alkyl]amino, H$_2$N—(C=O)—, $(C_1-C_6)$alkyl-NH—(C=O)—, di[$(C_1-C_6)$alkyl]-N—(C=O)—, $(C_1-C_6)$alkyl-(C=O)—O—, $(C_1-C_6)$alkyl-(C=O)—N(R')—, formyl, $(C_1-C_6)$alkyl-(C=O)—, $(C_1-C_6)$alkoxy-(C=O)—, $(C_6-C_{10})$aryl and $(C_2-C_9)$heterocyclic; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$alkoxy, $(C_1-C_6)$alkyl-S—, $(C_1-C_6)$alkyl-S(=O)—, $(C_1-C_6)$alkyl-SO$_2$—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)— and $(C_1-C_6)$alkoxy-(C=O)—; wherein R' is hydrogen or $(C_1-C_6)$alkyl;

(e) (5- to 7-membered)-carbocyclic ring fused to a saturated, partially saturated or aromatic (5- to 7-membered)-carbocyclic ring; wherein said (5- to 7-membered)-carbocyclic ring may optionally contain one or two double bonds; wherein either of said (5- to 7-membered)-carbocyclic or said fused saturated, partially saturated or aromatic (5- to 7-membered)-carbocyclic ring is optionally substituted by 1 to 2 substituents per ring, wherein said substituents are independently selected from the group consisting of halo (preferably chloro, bromo or fluoro), hydroxy, cyano, mercapto, HO—(C=O)—, nitro, $(C_1-C_6)$alkyl, $(C_2-C_6)$alkenyl, $(C_2-C_6)$alkynyl, $(C_1-C_6)$alkoxy, —OCF$_3$, $(C_1-C_6)$ alkyl-S—, $(C_1-C_6)$alkyl-S(=O)—, $(C_1-C_6)$alkyl-SO$_2$—, amino, $(C_1-C_6)$alkylamino, di[$(C_1-C_6)$alkyl]amino, H$_2$N—(C=O)—, $(C_1-C_6)$alkyl-NH—(C=O)—, di[$(C_1-C_6)$alkyl]-N—(C=O)—, $(C_1-C_6)$alkyl-(C=O)—O—, $(C_1-C_6)$alkyl-(C=O)—N(R')—, formyl, $(C_1-C_6)$alkyl-(C=O)—, $(C_1-C_6)$alkoxy-(C=O)—, $(C_6-C_{10})$aryl and $(C_2-C_9)$heterocyclic; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$alkoxy, $(C_1-C_6)$alkyl-S—, $(C_1-C_6)$alkyl-S(=O)—, $(C_1-C_6)$alkyl-SO$_2$—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)— and $(C_1-C_6)$alkoxy-(C=O)—; wherein R' is hydrogen or $(C_1-C_6)$alkyl;

(f) (5- to 7-membered)-carbocyclic ring fused to a saturated, partially unsaturated or aromatic (5- to 6-membered)-heterocyclic ring containing 1 to 2 ring heteroatoms independently selected from the group consisting of —N=, —NR'—, —S— or —O—; wherein said (5 to 7-membered)-carbocyclic ring may optionally contain one or two double bonds; wherein either of said (5- to 7-membered)-carbocyclic or said fused saturated, partially unsaturated or aromatic (5- to 6-membered)-heterocyclic ring is optionally substituted with one to two substituents per ring, wherein said substituents are independently selected from the group consisting of halo (preferably chloro, bromo or fluoro), hydroxy, cyano, mercapto, HO—(C=O)—, nitro, $(C_1-C_6)$alkyl, $(C_2-C_6)$alkenyl, $(C_2-C_6)$alkynyl, $(C_1-C_6)$alkoxy, —OCF$_3$, $(C_1-C_6)$alkyl-S—, $(C_1-C_6)$alkyl-S(=O)—, $(C_1-C_6)$alkyl-SO$_2$—, amino, $(C_1-C_6)$alkylamino, di[$(C_1-C_6)$alkyl]amino, H$_2$N—(C=O)—, $(C_1-C_6)$alkyl-NH—(C=O)—, di[$(C_1-C_6)$alkyl]-N—(C=O)—, $(C_1-C_6)$alkyl-(C=O)—O—, $(C_1-C_6)$alkyl-(C=O)—N(R'), formyl, $(C_1-C_6)$alkyl-(C=O)—, $(C_1-C_6)$alkoxy-(C=O)—, $(C_6-C_{10})$aryl and $(C_2-C_9)$heterocyclic; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C-C_6)$alkyl, $(C_2-C_6)$alkenyl, $(C_1-C_6)$alkoxy, $(C_1-C_6)$alkyl-S—, $(C_1-C_6)$alkyl-S(=O)—, $(C_1-C_6)$alkyl-SO$_2$—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)— and $(C_1-C_6)$alkoxy-(C=O)—; wherein R' is hydrogen or $(C_1-C_6)$alkyl;

(g) saturated, partially unsaturated or aromatic (5- to 6-membered)heterocyclic ring containing 1 to 4 ring heteroatoms independently selected from —N=, —NR—, —O—, or —S—, wherein said (5- to 6-membered)heterocyclic ring is optionally substituted by 1–3 substituents independently selected from the group consisting of halo (preferably chloro, bromo or fluoro), hydroxy, cyano, mercapto, HO—(C=O)—, nitro, $(C_1-C_6)$alkyl, $(C_2-C_6)$alkenyl, $(C_2-C_6)$alkynyl, $(C_1-C_6)$alkoxy, —OCF$_3$, $(C_1-C_6)$alkyl-S—, $(C_1-C_6)$alkyl-S(=O)—, $(C_1-C_6)$alkyl-SO$_2$—, amino, $(C_1-C_6)$alkylamino, di[$(C_1-C_6)$alkyl]amino, H$_2$N—(C=O)—, $(C_1-C_6)$alkyl-NH—(C=O)—, di[$(C_1-C_6)$alkyl]-N—(C=O)—, $(C_1-C_6)$alkyl-(C=O)—O—, $(C_1-C_6)$alkyl-(C=O)—N(R')—, formyl, $(C_1-C_6)$alkyl-(C=O)—, $(C_1-C_6)$alkoxy-(C=O)—, $(C_6-C_{10})$aryl and $(C_2-C_9)$heterocyclic; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$alkoxy, $(C_1-C_6)$alkyl-S—, $(C_1-C_6)$alkyl-S(=O)—, $(C_1-C_6)$alkyl-SO$_2$—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)— and $(C_1-C_6)$alkoxy-(C=O)—; wherein R' is hydrogen or $(C_1-C_6)$alkyl;

(h) saturated, partially unsaturated or aromatic (5- to 6-membered)heterocyclic ring containing 1 to 2 ring heteroatoms independently selected from the group consisting of —N=, —NR'—, —S— or —O—; wherein said (5- to 6-membered)heterocyclic ring is fused to a saturated, partially saturated or aromatic (5- to 7-membered)-carbocyclic ring; wherein either of said (5- to 6-membered)heterocyclic ring or said fused saturated, partially saturated or aromatic (5- to 7-membered)-carbocyclic ring is optionally substituted by 1 to 2 substituents per ring, wherein said substituents are independently selected from the group consisting of halo (preferably chloro, bromo or fluoro), hydroxy, cyano, mercapto, HO—(C=O)—, nitro, $(C_1-C_6)$alkyl, $(C_2-C_6)$alkenyl, $(C_2-C_6)$alkynyl, $(C_1-C_6)$alkoxy, —OCF$_3$, $(C_1-C_6)$alkyl-S—, $(C_1-C_6)$alkyl-S(=O)—, $(C_1-C_6)$alkyl-SO$_2$—, amino, $(C_1-C_6)$alkylamino, di[$(C_1-C_6)$alkyl]amino, H$_2$N—(C=O)—, $(C_1-C_6)$alkyl-NH—(C=O)—, di[$(C_1-C_6)$alkyl]-N—(C=O)—, $(C_1-C_6)$alkyl-(C=O)—O—, $(C_1-C_6)$alkyl-(C=O)—N(R')—, formyl, $(C_1-C_6)$alkyl-(C=O)—, $(C_1-C_6)$alkoxy-(C=O)—, $(C_6-C_{10})$aryl and $(C_2-C_9)$heterocyclic; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$alkoxy, $(C_1-C_6)$alkyl-S—, $(C_1-C_6)$alkyl-S(=O)—, $(C_1-C_6)$alkyl-SO$_2$—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)— and $(C_1-C_6)$alkoxy-(C=O)—; wherein R' is hydrogen or $(C_1-C_6)$alkyl; and (i) saturated, partially unsaturated or aromatic (5- to 6-membered)heterocyclic ring containing 1 to 2 ring heteroatoms independently selected from the group consisting of —N=, —NR'—, —S—, or —O—; wherein said (5- to 6-membered)heterocyclic ring is fused to a saturated, partially saturated or aromatic (5- to 6-membered)heterocyclic containing 1 to 2 ring heteroatoms independently selected from the group consisting of —N=, —NR'—, —S— or —O—; wherein either of said saturated, partially saturated or aromatic (5 to 6-membered)heterocyclic ring or said fused saturated, partially unsaturated or aromatic (5- to 6-membered)-heterocyclic ring is optionally substituted with one to two substituents per ring, wherein said substituents are independently selected from the group consisting of halo (preferably chloro, bromo or fluoro), hydroxy, cyano, mercapto, HO—(C=O)—, nitro, $(C_1-C_6)$ alkyl, $(C_2-C_6)$alkenyl, $(C_2-C_6)$alkynyl, $(C_1-C_6)$ alkoxy, —OCF$_3$, $(C_1-C_6)$alkyl-S—, $(C_1-C_6)$alkyl-S (=O)—, $(C_1-C_6)$alkyl-SO$_2$—, amino, $(C_1-C_6)$ alkylamino, di[$(C_1-C_6)$alkyl]amino, H$_2$N— (C=O)—, $(C_1-C_6)$alkyl-NH—(C=O)—, di[$(C_1-C_6)$alkyl]-N—(C=O)—, $(C_1-C_6)$alkyl- (C=O)—O—, $(C_1-C_6)$alkyl-(C=O)—N(R'), formyl, $(C_1-C_6)$alkyl-(C=O)—, $(C_1-C_6)$alkoxy- (C=O)—, $(C_6-C_{10})$aryl and $(C_2-C_9)$heterocyclic; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$alkoxy, $(C_1-C_6)$alkyl-S—, $(C_1-C_6)$alkyl-S(=O)—, $(C_1-C_6)$alkyl-SO$_2$—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-(C=O)—O—, $(C_1-C_6)$alkyl- (C=O)—N(R')—, formyl, $(C_1-C_6)$alkyl-(C=O)— and $(C_1-C_6)$alkoxy-(C=O)—; wherein R' is hydrogen or $(C_1-C_6)$alkyl;

$R^7$ is hydrogen or $(C_1-C_6)$alkyl;

$R^8$ is hydrogen; halo (preferably fluoro or chloro); hydroxy; mercapto; $(C_1-C_6)$alkyl; $(C_1-C_6)$alkoxy optionally substituted with one to three halogen atoms (preferably fluoro); $(C_2-C_6)$alkenyl; $(C_2-C_6)$alkynyl; cyano; formyl; $(C_1-C_6)$alkylcarbonyl; $(C_1-C_6)$alkyl-C (=O)—O—; HO—(O=C)—; $(C_1-C_6)$alkoxy-C (=O)—; aminocarbonyl; N—$(C_1-C_6)$ alkylaminocarbonyl; N,N—[$(C_1-C_6)$alkyl]$_2$ aminocarbonyl; nitro; amino; $(C_1-C_6)$alkylamino; [$(C_1-C_6)$alkyl]$_2$amino; or $(C_1-C_6)$alkyl-S—;

wherein said $R^8$ $(C_1-C_6)$alkyl group may optionally be substituted with one to three substitutents independently selected from halo, hydroxy, $(C_1-C_6)$alkoxy, cyano, nitro, HO—(O=C)—, $(C_1-C_6)$alkoxy-C (=O)—, amino, $(C_1-C_6)$alkylamino, di[$(C_1-C_6)$alkyl] amino, aminocarbonyl, N—$(C_1-C_6)$ alkylaminocarbonyl, N,N—[$(C_1-C_6)$alkyl]$_2$ aminocarbonyl, N—$(C_6-C_{10})$arylaminocarbonyl, N,N—[$(C_6-C_{10})$aryl]$_2$aminocarbonyl, N—$(C_1-C_6)$ alkyl-N—$(C_6-C_{10})$arylaminocarbonyl, $(C_6-C_{10})$aryl, $(C_6-C_{10})$aryloxy, $(C_2-C_9)$heteroaryl, $(C_2-C_9)$ heteroaryloxy, morpholino-carbonyl, $(C_1-C_6)$ alkoxyaminocarbonyl or $(C_1-C_6)$alkyl-carbonylamino;

and the pharmaceutically acceptable salts thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds of the invention also exist in different tautomeric forms. This invention relates to all tautomers of formula I.

The compounds of this invention may contain olefin-like double bonds. When such bonds are present, the compounds of the invention exist as cis and trans configurations and as mixtures thereof.

Unless otherwise indicated, the alkyl, referred to herein, as well as the alkyl moieties of other groups referred to herein (e.g., alkoxy), may be linear or branched (such as methyl, ethyl, n-propyl, isopropyl, n-butyl, isobutyl, secondary-butyl, tertiary-butyl), and they may also be cyclic (e.g., cyclopropyl, or cyclobutyl); optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. The phrase "each of said alkyl" as used herein refers to any of the preceding alkyl moieties within a group such alkoxy, alkenyl or alkylamino.

Unless otherwise indicated, halogen includes fluoro, chloro, bromo or iodo, or fluoride, chloride, bromide or iodide.

As used herein, the term "halo-substituted alkyl" refers to an alkyl radical as described above substituted with one or more halogens included, but not limited to, chloromethyl, dichloromethyl, fluoromethyl, difluoromethyl, trifluoromethyl, 2,2,2-trichloroethyl, and the like; optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "alkynyl" is used herein to mean straight or branched hydrocarbon chain radicals of 2 to 6 carbon atoms having one triple bond including, but not limited to, ethynyl, propynyl, butynyl, and the like; optionally substituted by 1 to 3 suitable substituents as defined below such as fluoro, chloro, trifluoromethyl, $(C_1-C_6)$ alkoxy, $(C_6-C_{10})$aryloxy, trifluoromethoxy, difluoromethoxy or $(C_1-C_6)$alkyl.

As used herein, the term "alkoxy" refers to 0-alkyl groups, wherein alkyl is as defined above.

As used herein, the term "alkoxycarbonyl" refers to an alkoxy radical as described above connected to a carbonyl group (>C=O), which, in turn, serves as the point of attachment.

As used herein the term "aryl" means aromatic radicals such as phenyl, naphthyl, tetrahydronaphthyl, indanyl and the like; optionally substituted by 1 to 3 suitable substituents as defined below such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl.

As used herein "heteroaryl" group usually has one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, triazinyl, thienyl, furyl, pyranyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), tetrazole, quinolyl, isoquinolyl, benzothienyl, isobenzofuranyl, benzofuryl, indolyl, quinoxalinyl and the like; optionally substituted by 1 to 3 suitable substituents as defined below such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl.

The term "heterocyclic" as used herein refers to a cyclic group containing 2–9 carbon atoms and 1–4 hetero atoms selected from N, O, S or NR'. Examples of such rings include furyl, thienyl, pyrrolyl, pyrazolyl, imidazolyl, triazolyl, tetrazolyl, isoxazolyl, oxazolyl, thiazolyl, isothiazolyl, oxadiazolyl, oxatriazolyl, pyridyl, pyridazinyl, pyrimidinyl, pyrazinyl, triazinyl, and the like. Examples of said monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholine, 1,2-tetrahydrothiazin-2-yl, 1,3-tetrahydrothiazin-3-yl, tetrahydrothiadiazine, morpholine, 1,2-tetrahydrodiazin-2-yl, 1,3-tetrahydrodiazin-1-yl, 1,4-oxazin-2-yl, 1,2,5-oxathiazin-4-yl and the like; optionally substituted by 1 to 3 suitable substituents as defined below such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl.

The term "phenyl fused to a saturated, partially saturated or aromatic (5 to 7-membered)-carbocyclic ring", as used herein, unless otherwise indicated, means a bicyclic group having a first phenyl ring covalently bound to the pyrazole nucleus and wherein said first ring is fused to a second ring comprising a 5 to 7 membered carbocycle, wherein the 5 to 7 members include the carbon atoms common to both rings. Examples of such rings include tetralin-5-yl, tetralin-6-yl, 2,3-dihydro-inden-4-yl, 2,3-dihydro-inden-5-yl, inden-4-yl, inden-5-yl, 7,8-dihydro-naphthalen-1-yl, 7,8-dihydro-naphthalen-2-yl, 5,6-dihydro-naphthalen-1-yl, 5,6-dihydro-naphthalen-2-yl, 5,8-dihydro-naphthalen-1-yl, 5,8-dihydro-naphthalen-2-yl, naphthalen-1-yl, naphthalen-2-yl, 5-(6,7,8,9-tetrahydro-5H-benzocyclohepten-1-yl)-, 5(8,9-dihydro-7H-benzocyclohepten-1-yl)-, 5-(6,7-dihydro-5H-benzocyclohepten-1-yl)-, 5-(7H-benzocyclohepten-1-yl)-, 5-(5H-benzocyclohepten-1-yl)-, 5-(9H-benzocyclohepten-1-yl)-, 5-(6,7,8,9-tetrahydro-5H-benzocyclohepten-2-yl), 5-(6,7-dihydro-5H-benzocyclohepten-2-yl)-, 5-(8,9-dihydro-7H-benzocyclohepten-2-yl)-, 5-(5H-benzocyclohepten-2-yl)-, 5(9H-benzocyclohepten-2-yl)-, 5-(7H-benzocyclohepten-2-yl)-, and the like; optionally substituted by 1 to 3 suitable substituents as defined below such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl.

The term "phenyl fused to a saturated, partially saturated or aromatic (5 to 6-membered)-heterocyclic ring", as used herein, unless otherwise indicated, means a bicyclic group having a first phenyl ring covalently bound to the pyrazole nucleus and wherein said first ring is fused to a second ring comprising a (5- to 6-membered)-heterocyclic ring, wherein the 5 to 6 members include the carbon atoms common to both rings. Said second ring comprises a saturated, partially saturated or aromatic (5- to 6-membered)heterocyclic ring. Examples of such rings include quinolin-5-yl, quinolin-6-yl, quinolin-7-yl, quinolin-8-yl, isoquinolin-5-yl, isoquinolin-6-yl, isoquinolin-7-yl, isoquinolin-8-yl, quinazolin-5-yl, quinazolin-6-yl, quinazolin-7-yl, quinazolin-8-yl, cinnolin-5-yl, cinnolin-6-yl, cinnolin-7-yl, cinnolin-8-yl, 4H-1,4-benzoxazin-5-yl, 4H-1,4-benzoxazin-6-yl, 4H-1,4-benzoxazin-7-yl, 4H-1,4-benzoxanic-8-yl, 4H-1,4-benzthiazin-5-yl, 4H-1,4-benzthiazin-6-yl, 4H-1,4-benzthiazin-7-yl, 4H-1,4H-benzthiazin-8-yl, 1,4H-1,4-benzdiazin-5-yl, 1,4H-1,4-benzdiazin-6-yl, 1,4H-1,4-benzdiazin-7-yl, 1,4H-1,4-benzdiazin-8-yl, indol4-yl, indol-5-yl, indol-6-yl, indol-7-yl, benzo(b)thiophen-4-yl, benzo(b)thiophen-5-yl, benzo(b)thiophen-6-yl, benzo(b)thiophen-7-yl, benzofuran-4-yl, benzofuran-5-yl, benzofuran-6-yl, benzofuran-7-yl, benzisoxazol-4-yl, benzisoxazol-5-yl, benzisoxazol-6-yl, benzisoxazol-7-yl, benzoxazol4-yl, benzoxazol-4-yl, benzoxazol-5-yl, benzoxazol-6-yl and benzoxazol-7-yl. Preferred fused phenylheteroaryl rings include quinolinyl, isoquinolinyl, indolyl, benzo(b)thiophenyl, benzofuranyl and the like; optionally substituted by 1 to 3 suitable substituents as defined below such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl.

The term "(5- to 7-membered)carbocyclic", as used herein, unless otherwise indicated, means a monocyclic group containing 5 to 7 carbon atoms and optionally containing 1 or 2 double bonds. Examples of such rings include cyclopentyl, cyclohexyl, cycloheptanyl, cyclopentenyl, cyclohexenyl and cycloheptenyl and the like; optionally substituted by 1 to 3 suitable substituents as defined below such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl.

The term "(5- to 7-membered)-carbocyclic fused to a saturated or partially saturated (5- to 7-membered)-carbocyclic ring", as used herein, unless otherwise indicated, means a bicyclic group having a first carbocyclic ring covalently bound to the pyrazole nucleus and wherein said first ring is fused to a second ring comprising a 5 to 7 membered carbocycle, wherein the 5 to 7 members include the carbon atoms common to both rings and wherein said second ring may contain 1, 2 or 3 double bonds. Examples of such rings, wherein the fusion is so called ortho fused, include tetralin-1-yl, tetralin-2-yl, hexahydronaphthalen-1-yl, hexahydronaphthalen-2-yl, octahydronaphthalen-1-yl, octahydronaphthalen-2-yl, decalin-1-yl, decalin-2-yl, 4,5,6,7-tetrahydro-indan-4-yl, 4,5,6,7-tetrahydro-indan-5-yl, 4,5,6,7,8,9-hexahydro-indan-4-yl, 4,5,6,7,8,9-hexahydro-indan-5-yl, 4,5,6,7-tetrahydro-inden-4-yl, 4,5,6,7-tetrahydro-inden-5-yl, 4,5,6,7,8,9-hexahydro-inden-4-yl, 4,5,6,7,8,9- hexahydro-inden-5-yl, pentalan-1-yl, pentalan-2-yl, 4,5 dihydro-pentalan-1-yl, 4,5 dihydro-pentalan-2-yl, 4,5,6,7-tetrahydro-pentalan-1-yl, 4,5,6,7 tetra-pentalan-2-yl, benzocycloheptan-5-yl, benzocycloheptan-6-yl and the like. Examples of such bicyclic rings that are not ortho fused include bicyclo[3.2.1]-octan-2-yl, bicyclo[3.2.1]-octan-3-yl, bicyclo[5.2.0]nonan-2-yl, bicyclo[5.2.0]nonan-3-yl, bicyclo[5.2.0]nonan-4-yl, bicyclo[4.3.2]undecan-7-yl, bicyclo[4.3.2]undecan-8-yl, bicyclo[4.3.2]undecan-9-yl, bicyclo[2.2.2]-octan-2-yl, bicyclo[2.2.2]-octan-3-yl, bicyclo[2.2.1]-heptan-2-yl, bicyclo[3.1.1]-heptan-2-yl, borneol-2-yl and the like optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

The term "(5- to 7-membered)carbocyclic fused to a saturated, partially saturated or aromatic (5 to 6-membered)-heterocyclic", as used herein, unless otherwise indicated, means a bicyclic group having a first carbocyclic ring covalently bound to the pyrazole nucleus and wherein said first ring is fused to a second ring comprising a 5 to 6 membered heterocyclic ring, wherein said second 5 to 6 members include the atoms common to both rings. Said second ring comprises a saturated, partially saturated or aromatic (5- to 6-membered)-heterocyclic ring. Examples of said bicyclic ring systems are 5,6,7,8 tetrahydro-quinolin-5-yl, 5,6,7,8 tetrahydro-quinolin-6-yl, 5,6,7,8 tetrahydro-quinolin-7-yl, 5,6,7,8 tetrahydro-quinolin-8-yl, 5,6,7,8 tetrahydro-isoquinolin-5-yl, 5,6,7,8 tetrahydro-isoquinolin-6-yl, 5,6,7,8 tetrahydro-isoquinolin-7-yl, 5,6,7,8 tetrahydro-isoquinolin-8-yl, 5,6,7,8 tetrahydro-quinazolin-5-yl, 5,6,7,8 tetrahydro-quinazolin-6-yl, 5,6,7,8 tetrahydro-quinazolin-7-yl, 5,6,7,8 tetrahydro-quinazolin-8-yl, 5,6,7,8 tetrahydro-4H-1,4-benzoxazin-5-yl, 5,6,7,8 tetrahydro-4H-1,4-benzoxazin-6-yl, 5,6,7,8 tetrahydro-4H-1,4-benzoxazin-7-yl, 5,6,7,8 tetrahydro-4H-1,4-benzoxazin-8-yl, 5,67,8 tetrahydro-4H-1,4-benzthiazin-5-yl, 5,6,7,8 tetrahydro-4H-1,4-benzthiazin-6-yl, 5,6,7,8 tetrahydro-4H-1,4-benzthiazin-7-yl, 5,6,7,8 tetrahydro-4H-1,4-benzthiazin-8-yl, 5,6,7,8 tetrahydro-1,4H-1,4-benzdiazin-5-yl, 5,6,7,8 tetrahydro-1,4H-1,4-benzdiazin-6-yl, 5,6,7,8 tetrahydro-1,4H-1,4-benzdiazin-7-yl, 5,6,7,8 tetrahydro-1,4H-1,4-benzdiazin-8-yl, 4,5,6,7 tetrahydro-indol4-yl, 4,5,6,7 tetrahydro indol-5-yl, 4,5,6,7 tetrahydro-indol-6-yl, 4,5,6,7 tetrahydro-indol-7-yl, 4,5,6,7 tetrahydro-benzo(b)thiophen-4-yl, 4,5,6,7 tetrahydro-benzo(b)thiophen-5-yl, 4,5,6,7 tetrahydro-benzo(b)thiophen-6-yl, 4,5,6,7 tetrahydro-benzo(b)thiophen-7-yl, 4,5,6,7 tetrahydro-benzofuran-4-yl, 4,5,6,7 tetrahydro-benzofuran-5-yl, 4,5,6,7 tetrahydro-benzofuran-6-yl, 4,5,6,7 tetrahydro-benzofuran-7-yl, 4,5,6,7 tetrahydro-benzisoxazol4-yl, 4,5,6,7 tetrahydro-benzisoxazol-5-yl, 4,5,6,7 tetrahydro-benzisoxazol-6-yl, 4,5,6,7 tetrahydro-benzisoxazol-7-yl, 4,5,6,7 tetrahydro-benzoxazol4-y), 4,5,6,7 tetrahydro-benzoxazol-4-yl, 4,5,6,7 tetrahydro-benzoxazol-5-yl, 4,5,6,7 tetrahydro-benzoxazol-6-yl, 4,5,6,7 tetrahydro-benzoxazol-7-yl and the like; optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

The term "saturated, partially saturated or aromatic (5- to 6-membered)heterocyclic containing 1 to 4 ring heteroatoms independently selected from —N═, —NR—, —O—, or —S—", as used herein, unless otherwise indicated, means a monocyclic (5- to 6-membered)heterocyclic ring covalently bound to the pyrazole nucleus. Said ring may contain optional double bonds so as to include saturated, partially saturated or aromatic (5- to 6-membered)-heterocyclic rings. Examples of the monocyclic aromatic ring systems are furyl, thienyl, pyrrolyl, pyrazolyl, imidazolyl, triazolyl, tetrazolyl, isoxazolyl, oxazolyl, thiazolyl, isothiazolyl, oxadiazolyl, oxatriazolyl, pyridyl, pyridazinyl, pyrimidinyl, pyrazinyl, triazinyl, and the like. Examples of said monocyclic saturated or partially saturated ring systems are piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholine, 1,2-tetrahydrothiazin-2-yl, 1,3-tetrahydrothiazin-3-yl, tetrahydrothiadiazine, morpholine, 1,2-tetrahydrodiazin-2-yl, 1,3-tetrahydrodiazin-1-yl, 1,4-oxazin-2-yl, 1,2,5-oxathiazin-4-yl and the like; optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

The term "saturated, partially saturated or aromatic (5- to 6-membered)heterocyclic fused to a saturated, partially saturated or aromatic (5- to 7-membered)-carbocyclic ring", as used herein, unless otherwise indicated, means a bicyclic group having a first (5- to 6-membered)heterocyclic ring covalently bound to the pyrazole nucleus and wherein said first ring is fused to a second ring comprising a 5 to 6 membered heterocyclic ring, wherein said second 5 to 6 members include the atoms common to both rings. Said first and second rings comprise saturated, partially saturated or aromatic (5- to 6-membered)-heterocyclic rings. Examples of said bicyclic ring systems are indolidin-4-yl, indolidin-5-yl, quinolidin-5-yl, quinolidin-6-yl, quinolidin-7-yl, quinolidin-8-yl, isoquinolidin-5-yl, isoquinolidin-6-yl, isoquinolidin-7-yl, isoquinolidin-8-yl, quinazolidin-5-yl, quinazolidin-6-yl, quinazolidin-7-yl, quinazolidin-8-yl, benzofuran-2-yl, benzofuran-3-yl, isobenzofuran-1-yl, isobenzofuran-3-yl, benzothiophen-2-yl, benzothiophen-3-yl, indol-2-yl, indol-3-yl, isoindol-1-yl, isoindol-3-yl, cyclopentapyrid-2-yl, cyclopentapyrid-3-yl, benzoxazol-2-yl, cinnolin-4-yl and the like; optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

The term "saturated, partially saturated or aromatic (5- to 6-membered)heterocyclic fused to a saturated, partially saturated or aromatic (5- to 6-membered)-heterocyclic" as used herein, unless otherwise indicated, means a bicyclic heterocyclic group having a first ring covalently bound to the pyrazole nucleus and containing five to six ring atoms comprising one to two heteroatoms each independently selected from —N═, —NH—, —[N—$(C_1-C_4)$alkyl]-, —O— and —S—; wherein said first ring is fused to a second ring comprising a 5 to 6 membered heterocyclic ring, wherein said second 5 to 6 members include the atoms common to both rings. Said second ring comprises a saturated, partially saturated or aromatic (5- to 6-membered)-heterocyclic ring. Examples of said bicyclic ring systems are pyrano[3,4b]pyrrolyl, pyrano[3,2b]pyrrolyl, pyrano[4,3b]pyrrolyl, purin-2-yl, purin-6-yl, purin-7-yl, purin-8-yl, pteridin-2-yl, pyrido[3,4b]pyridyl, pyrido[3,2b]pyridyl, pyrido[4,3b]pyridyl, naphthyridinyl and the like; optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

"A suitable substituent" is intended to mean a chemically and pharmaceutically acceptable functional group i.e., a moiety that does not negate the inhibitory activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, carboxy groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, arylsulfonyl groups and the like; optionally substituted by 1 to 3 suitable substituents as defined below such as fluoro, chloro, trifluoromethyl, $(C_1-C_6)$alkoxy, $(C_1-C_{10})$aryloxy, trifluoromethoxy, difluoromethoxy or $(C_1-C_6)$alkyl.

An embodiment and a preferred group of compounds of the present invention includes compounds of formula I, referred to as the IA(1) Group of compounds, wherein said compounds have the formula

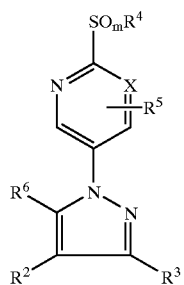

IA1 wherein X is $CR^8$ or N.

Another embodiment and a preferred group of compounds of the present invention includes compounds of formula I, referred to as the IA(2) Group of compounds, wherein said compounds have the formula

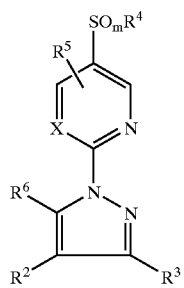

IA2 wherein X is $CR^8$ or N.

An embodiment of the present invention includes compounds of formula I, referred to as the IA(3) Group of compounds, wherein said compounds have the formula

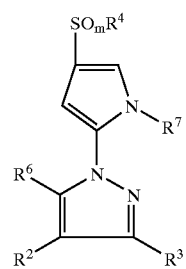

IA3 wherein $R^2$, $R^3$, $R^4$, $R^6$ and $R^7$ are as defined above.

An embodiment of the present invention includes compounds of formula I, referred to as the IA(4) Group of compounds, wherein said compounds have the formula

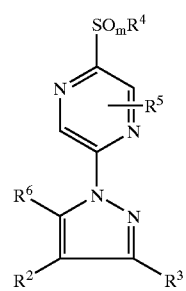

IA4 wherein $R^2$, $R^3$, $R^4$, $R^6$ and $R^7$ are as defined above.

An embodiment of the present invention includes compounds of formula I, referred to as the IA(5) Group of compounds, wherein said compounds have the formula

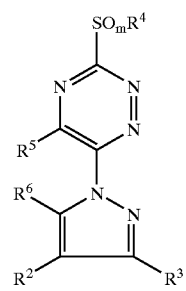

IA5 wherein $R^2$, $R^3$, $R^4$, $R^6$ and $R^7$ are as defined above.

An embodiment of the present invention includes compounds of formula I, referred to as the IA(6) Group of compounds, wherein said compounds have the formula

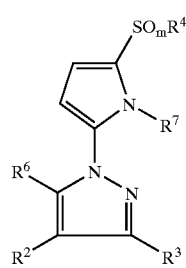

IA6 wherein $R^2$, $R^3$, $R^4$, $R^6$ and $R^7$ are as defined above.

An embodiment of the present invention includes compounds of formula I, referred to as the IA(7) Group of compounds, wherein said compounds have the formula

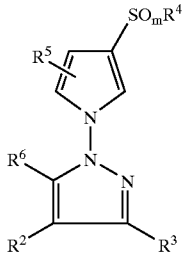

IA7 wherein $R^2$, $R^3$, $R^4$, $R^6$ and $R^7$ are as defined above.

An embodiment of the present invention includes compounds of formula I, referred to as the IA(8) Group of compounds, wherein said compounds have the formula

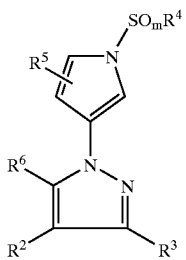

IA8 wherein $R^2$, $R^3$, $R^4$, $R^6$ and $R^7$ are as defined above.

An embodiment of the present invention includes compounds of formula I, referred to as the A(9) Group of compounds, wherein said compounds have the formula

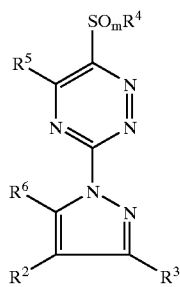

IA9 wherein $R^2$, $R^3$, $R^4$, $R^6$ and $R^7$ are as defined above.

An embodiment of the present invention includes compounds of formula I, referred to as the A(10) Group of compounds, wherein said compounds have the formula

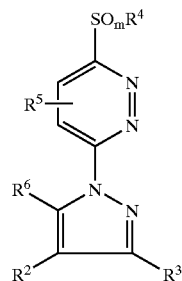

IA10 wherein $R^2$, $R^3$, $R^4$, $R^6$ and $R^7$ are as defined above.

An embodiment and a particularly preferred group of compounds of the present invention includes compounds of formula I, referred to as the $R^6$(a) Group of compounds, wherein $R^6$ is phenyl optionally substituted by 1–3 substituents independently selected from the group consisting of halo (preferably chloro, bromo or fluoro), hydroxy, cyano, mercapto, HO—(C=O)—, nitro, ($C_1$–$C_6$)alkyl, ($C_2$–$C_6$) alkenyl, ($C_1$–$C_6$)alkoxy, —OCF$_3$, ($C_1$–$C_6$)alkyl-S—, ($C_1$–$C_6$)alkyl-S(=O)—, ($C_{C6}$)alkyl-SO$_2$—, amino, ($C_1$–$C_6$) alkylamino, di[($C_1$–$C_6$)alkyl]amino, H$_2$N—(C=O)—, ($C_1$–$C_6$)alkyl-NH—(C=O)—, di[($C_1$–$C_6$)alkyl]-N—(C=O)—, ($C_1$–$C_6$)alkyl-(C=O)—O—, ($C_1$–$C_6$)alkyl-(C=O)—N(R')—, formyl, ($C_1$–$C_6$)alkyl-(C=O)—, ($C_1$–$C_6$)alkoxy-(C=O)—, ($C_6$–$C_{10}$)aryl and ($C_2$–$C_9$) heterocyclic; wherein R' is hydrogen or ($C_1$–$C_6$)alkyl; wherein each of said ($C_1$–$C_6$)alkyl is optionally substituted with 1 to 3 substituents independently selected from the group consisting of halo, hydroxy, cyano, mercapto, HO—(C=O)—, nitro, ($C_1$–$C_6$)alkyl, ($C_2$–$C_6$)alkenyl, ($C_1$–$C_6$) alkoxy, ($C_1$–$C_6$)alkyl-S—, amino, ($C_1$–$C_6$)alkylamino, di[($C_1$–$C_6$)alkyl]amino, amido, ($C_1$–$C_6$)alkylamido, di[($C_1$–$C_6$)alkyl]amido, ($C_1$–$C_6$)alkyl-(C=O)—O—, ($C_1$–$C_6$)alkyl-(C=O)—N(R')—, formyl, ($C_1$–$C_6$)alkyl-(C=O)— and ($C_1$–$C_6$)alkoxy-(C=O)—.

An embodiment of the present invention and a moderately preferred group of compounds of the present invention includes compounds of formula I, referred to as the $R^6$(b) Group of compounds, wherein $R^6$ is phenyl fused to a saturated, partially saturated or aromatic (5- to 7-membered)-carbocyclic ring; wherein either of said phenyl or said fused saturated, partially saturated or aromatic (5- to 7-membered)-carbocyclic ring is optionally substituted by 1 to 2 substituents per ring, wherein said substituents are independently selected from the group consisting of halo (preferably chloro, bromo or fluoro), hydroxy, cyano, mercapto, HO—(C=O)—, nitro, ($C_1$–$C_6$)alkyl, ($C_2$–$C_6$) alkenyl, ($C_2$–$C_6$)alkynyl, ($C_1$–$C_6$)alkoxy, —OCF$_3$, ($C_1$–$C_6$) alkyl-S—, ($C_1$–$C_6$)alkyl-S(=O)—, ($C_1$–$C_6$)alkyl-SO$_2$—, amino, ($C_1$–$C_6$)alkylamino, di[($C_1$–$C_6$)alkyl]amino, H$_2$N—(C=O)—, ($C_1$–$C_6$)alkyl-NH—(C=O)—, di[($C_1$–$C_6$) alkyl]-N—(C=O)—, ($C_1$–$C_6$)alkyl-(C=O)—O—, ($C_1$–$C_6$)alkyl-(C=O)—N(R')—, formyl, ($C_1$–$C_6$)alkyl-(C=O)—, ($C_1$–$C_6$)alkoxy-(C=O)—, ($C_6$–$C_{10}$)aryl and ($C_2$–$C_9$)heterocyclic; wherein R' is hydrogen or ($C_1$–$C_6$) alkyl; wherein each of said ($C_1$–$C_6$)alkyl is optionally substituted with 1 to 3 substituents independently selected from the group consisting of halo, hydroxy, cyano, mercapto, HO—(C=O)—, nitro, ($C_1$–$C_6$)alkyl, ($C_2$–$C_6$)alkenyl, ($C_1$–$C_6$)alkoxy, ($C_1$–$C_6$)alkyl-S—, amino, ($C_1$–$C_6$) alkylamino, di[($C_1$–$C_6$)alkyl]amino, amido, ($C_1$–$C_6$) alkylamido, di[($C_1$–$C_6$)alkyl]amido, ($C_1$–$C_6$)alkyl-(C=O)—O—, ($C_1$–$C_6$)alkyl-(C=O)—N(R')—, formyl, ($C_1$–$C_6$)alkyl-(C=O)— and ($C_1$–$C_6$)alkoxy-(C=O)—.

An embodiment and a preferred group of compounds of the present invention includes compounds of formula I, referred to as the $R^6(c)$ Group of compounds, wherein $R^6$ is phenyl fused to a saturated, partially saturated or aromatic (5- to 6-membered)heterocyclic ring containing 1 to 2 ring heteroatoms independently selected from the group consisting of —N=, —NR'—, —S— or —O—; wherein either of said phenyl or said fused saturated, partially saturated or aromatic (5- to 6-membered)-heterocyclic ring is optionally substituted with one to two substituents per ring, wherein said substituents are independently selected from the group consisting of halo (preferably chloro, bromo or fluoro), hydroxy, cyano, mercapto, HO—(C=O)—, nitro, $(C_1-C_6)$alkyl, $(C_2-C_6)$alkenyl, $(C_2-C_6)$alkynyl, $(C_1-C_6)$alkoxy, —$OCF_3$, $(C_1-C_6)$alkyl-S—, $(C_1-C_6)$alkyl-S(=O), $(C_1-C_6)$alkyl-$SO_2$—, amino, $(C_1-C_6)$alkylamino, di[$(C_1-C_6)$alkyl]amino, $H_2N$—(C=O)—, $(C_1-C_6)$alkyl-NH—(C=O)—, di[$(C_1-C_6)$alkyl]-N—(C=O)—, $(C_1-C_6)$alkyl-(C=O)—O—, $(C_1-C_6)$alkyl-(C=O)—N(R')—, formyl, $(C_1-C_6)$alkyl-(C=O)—, $(C_1-C_6)$alkoxy-(C=O)—, $(C_6-C_{10})$aryl and $(C_2-C_9)$heterocyclic; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$alkoxy, $(C_1-C_6)$alkyl-S—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)— and $(C_1-C_6)$alkoxy-(C=O)—.

An embodiment of the present invention and a preferred group of compounds includes compounds of formula I, referred to as the $R^6(d)$ Group of compounds, wherein $R^6$ is (5- to 7-membered)-carbocyclic optionally containing one or two double bonds; wherein said (5- to 7-membered)-carbocyclic may also be optionally substituted by 1–3 substituents independently selected from the group consisting of halo (preferably chloro, bromo or fluoro), hydroxy, cyano, mercapto, HO—(C=O)—, nitro, $(C_1-C_6)$alkyl, $(C_2-C_6)$alkenyl, $(C_2-C_6)$alkynyl, $(C_1-C_6)$alkoxy, —$OCF_3$, $(C_1-C_6)$alkyl-S—, $(C_1-C_6)$alkyl-S(=O)—, $(C_1-C_6)$alkyl-$SO_2$—, amino, $(C_1-C_6)$alkylamino, di[$(C_1-C_6)$alkyl]amino, $H_2N$—(C=O)—, $(C_1-C_6)$alkyl-NH—(C=O)—, di[$(C_1-C_6)$alkyl]-N—(C=O)—, $(C_1-C_6)$alkyl-(C=O)—O—, $(C_1-C_6)$alkyl-(C=O)—N(R')—, formyl, $(C_1-C_6)$alkyl-(C=O)—, $(C_1-C_6)$alkoxy-(C=O)—, $(C_6-C_{10})$aryl and $(C_2-C_9)$heterocyclic; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$alkoxy, $(C_1-C_6)$alkyl-S—, amino, $(C_1-C_6)$alkylamino, di[$(C_1-C_6)$alkyl]amino, amido, $(C_1\ C_6)$alkylamido, di[$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)— and $(C_1-C_6)$alkoxy-(C=O)—.

An embodiment of the present invention includes compounds of formula I, referred to as the $R^6(e)$ Group of compounds, wherein $R^6$ is (5- to 7-membered)-carbocyclic fused to a saturated, partially saturated or aromatic (5- to 7-membered)-carbocyclic ring; wherein said (5 to 7-membered)-carbocyclic may optionally contain one or two double bonds; wherein either of said (5- to 7-membered)-carbocyclic or said fused saturated, partially saturated or aromatic (5- to 7-membered)-carbocyclic ring is optionally substituted by 1 to 2 substituents per ring, wherein said substituents are independently selected from the group consisting of halo (preferably chloro, bromo or fluoro), hydroxy, cyano, mercapto, HO—(C=O)—, nitro, $(C_1-C_6)$alkyl, $(C_2-C_6)$alkenyl, $(C_2-C_6)$alkynyl, $(C_1-C_6)$alkoxy, —$OCF_3$, $(C_1-C_6)$alkyl-S—, $(C_1-C_6)$alkyl-S(=O)—, $(C_1-C_6)$alkyl-$SO_2$—, amino, $(C_1-C_6)$alkylamino, di[$(C_1-C_6)$alkyl]amino, $H_2N$—(C=O)—, $(C_1-C_6)$alkyl-NH—(C=O)—, di[$(C_1-C_6)$alkyl]N—(C=O)—, $(C_1-C_6)$alkyl-(C=O)—O—, $(C_1-C_6)$alkyl-(C=O)—N(R')—, formyl, $(C_1-C_6)$alkyl-(C=O)—, $(C_1-C_6)$alkoxy-(C=O)—, $(C_6-C_{10})$aryl and $(C_2-C_9)$heterocyclic; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$alkoxy, $(C_1-C_6)$alkyl-S—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)— and $(C_1-C_6)$alkoxy-(C=O)—.

An embodiment of the present invention includes compounds of formula I, referred to as the $R^6(f)$ Group of compounds, wherein $R^6$ is (5- to 7-membered)-carbocyclic fused to a saturated, partially saturated or aromatic (5- to 6-membered)-heterocyclic containing 1 to 2 ring heteroatoms independently selected from the group consisting of —N=, —NR'—, —S— or —O—; wherein said (5- to 7-membered)-carbocyclic may optionally contain one or two double bonds; wherein either of said (5- to 7-membered)-carbocyclic or said fused saturated, partially saturated or aromatic (5- to 6-membered)-heterocyclic is optionally substituted with one to two substituents per ring, wherein said substituents are independently selected from the group consisting of halo, hydroxy, cyano, mercapto, HO—(C=O)—, nitro, $(C_1-C_6)$alkyl, $(C_2-C_6)$alkenyl, $(C_2-C_6)$alkynyl, $(C_1-C_6)$alkoxy, $(C_1-C_6)$alkyl-S—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)— and $(C_1-C_6)$alkoxy-(C=O)—; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$alkoxy, $(C_1-C_6)$alkyl-S—, amino, $(C_1-C_6)$alkylamino, di[$(C_1-C_6)$alkyl]amino, amido, $(C_1-C_6)$alkylamido, di]$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)— and $(C_1-C_6)$alkoxy-(C=O)—.

An embodiment of the present invention includes compounds of formula I, referred to as the $R^6(g)$ Group of compounds, wherein $R^6$ is saturated, partially saturated or aromatic (5- to 6-membered)heterocyclic containing 1 to 4 ring heteroatoms independently selected from N=, —NR—, —O—, or —S—, wherein said saturated, partially saturated or aromatic (5- to 6-membered)heterocyclic is optionally substituted by 1–3 substituents independently selected from the group consisting of halo (preferably chloro, bromo or fluoro), hydroxy, cyano, mercapto, HO—(C=O)—, nitro, $(C_1-C_6)$alkyl, $(C_2-C_6)$alkenyl, $(C_2-C_6)$alkynyl, $(C_1-C_6)$alkoxy, —$OCF_3$, $(C_1-C_6)$alkyl-S—, $(C_1-C_6)$alkyl-S(=O)—, $(C_1-C_6)$alkyl-$SO_2$—, amino, $(C_1-C_6)$alkylamino di[$(C_1-C_6)$alkyl]amino, $H_2N$—(C=O)—, $(C_1-C_6)$alkyl-NH—(C=O)—, di[$(C_1-C_6)$alkyl]N—(C=O)—, $(C_1-C_6)$alkyl-(C=O)—O—, $(C_1-C_6)$alkyl-(C=O)—N(R')—, formyl, $(C_1-C_6)$alkyl-(C=O)—, $(C_1-C_6)$alkoxy-(C=O)—, $(C_6-C_{10})$aryl and $(C_2-C_9)$ heterocyclic; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$ alkoxy, $(C_1-C_6)$alkyl-S—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)—O— and $(C_1-C_8)$alkoxy-(C=O)—.

An embodiment of the present invention includes compounds of formula I, referred to as the $R^6$(h) Group of compounds, wherein $R^6$ is saturated, partially saturated or aromatic (5- to 6-membered)heterocyclic containing 1 to 4 ring heteroatoms independently selected from the group consisting of —N=, —NR'—, —S— or —O—, wherein said saturated, partially saturated or aromatic (5- to 6-membered)heterocyclic is fused to a saturated, partially saturated or aromatic (5- to 7-membered)-carbocyclic ring; wherein either of said saturated, partially saturated or aromatic (5- to 6-membered)heterocyclic ring or said fused saturated, partially saturated or aromatic (5 to 7-membered)-carbocyclic ring is optionally substituted by 1 to 2 substituents per ring, wherein said substituents are independently selected from the group consisting of halo (preferably chloro, bromo or fluoro), hydroxy, cyano, mercapto, HO—(C=O)—, nitro, $(C_1-C_6)$alkyl, $(C_2-C_6)$alkenyl, $(C_2-C_6)$ alkynyl, $(C_1-C_6)$alkoxy, —OCF$_3$, $(C_1-C_6)$alkyl-S—, $(C_1-C_6)$alkyl-S(=O)—, $(C_1-C_6)$alkyl-SO$_2$—, amino, $(C_1-C_6)$alkylamino, di[$(C_1-C_6)$alkyl]amino, H$_2$N—(C=O)—, $(C_1-C_6)$alkyl-NH—(C=O)—, di[$(C_1-C_6)$ alkyl]-N—(C=O)—, $(C_1-C_6)$alkyl-(C=O)—O—, $(C_1-C_6)$alkyl-(C=O)—N(R')—, formyl, $(C_1-C_6)$alkyl-(C=O)—, $(C_1-C_6)$alkoxy-(C=O)—, $(C_6-C_{10})$aryl and $(C_2-C_9)$heterocyclic; wherein R' is hydrogen or $(C_1-C_6)$ alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$alkoxy, $(C_1-C_6)$alkyl-S—, amino, $(C_1-C_6)$ alkylamino, di[$(C_1-C_6)$alkyl]amino, amido, $(C_1-C_6)$ alkylamido, di[$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)— and $(C_1-C_6)$alkoxy-(C=O)—.

An embodiment of the present invention includes compounds of formula I, referred to as the $R^6$(i) Group of compounds, wherein $R^6$ is saturated, partially saturated or aromatic (5- to 6-membered)heterocyclic containing 1 to 2 ring heteroatoms independently selected from the group consisting of —N=, —NR'—, —S—, or —O—; wherein said saturated, partially saturated or aromatic (5- to 6-membered)heterocyclic is fused to a saturated, partially saturated or aromatic (5- to 6-membered)-heterocyclic containing 1 to 2 ring heteroatoms independently selected from the group consisting of —N=, —NR'—, —S— or —O—; wherein either of said saturated, partially saturated or aromatic (5- to 6-membered)heterocyclic or said fused saturated, partially saturated or aromatic (5- to 6-membered)-heterocyclic is optionally substituted with one to two substituents per ring, wherein said substituents are independently selected from the group consisting of halo (preferably chloro, bromo or fluoro), hydroxy, cyano, mercapto, HO—(C=O)—, nitro, $(C_1-C_6)$alkyl, $(C_2-C_6)$ alkenyl, $(C_2-C_6)$alkynyl, $(C_1-C_6)$alkoxy, —OCF$_3$, $(C_1-C_6)$ alkyl-S—, $(C_1-C_6)$alkyl-S(=O)—, $(C_1-C_6)$alkyl-SO$_2$—, amino, $(C_1 C_6)$alkylamino, di[$(C_1-C_6)$alkyl]amino, H$_2$N—(C=O)—, $(C_1-C_6)$alkyl-NH—(C=O)—, di[$(C_1-C_6)$ alkyl]-N—(C=O)—, $(C^1-C_6)$alkyl-(C=)—O—, $(C_1-C_6)$ alkyl-(C=O)—N(R')—, formyl, $(C_1-C_6)$alkyl-(C=O)—, $(C_1-C_6)$alkoxy-(C=O)—, $(C_6-C_{10})$aryl and $(C_2-C_9)$ heterocyclic; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$ alkoxy, $(C_1-C_6)$alkyl-S—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-(C=O)—O—, $(C_1-C_6)$alkyl-(C=O)—N(R')—, formyl, $(C_1-C_6)$alkyl-(C=O)— and $(C_1-C_6)$alkoxy-(C=O)—.

Subgeneric embodiments of the present invention of the "A" (i.e. A1, A2, A3, A4, A5, A6, A7, A8 and A9) and $R^6$ (i.e. $R^6$(a), $R^6$(b), $R^6$(c), $R^6$(d), $R^6$(e), $R^6$(f), $R^6$(g), $R^6$(h), $R^6$(i)). Groups of compounds are expressly contemplated by the present invention. Such subgeneric embodiments within the A1 Group of compounds include the A1 group in combination with each of the $R^6$ groups (i.e. A1-$R^6$(a), A1-$R^6$(b), A1-$R^6$(c), A1-$R^6$(d), A1-$R^6$(e), A1-$R^6$(f), A1-$R^6$(g), A1-$R^6$(h) and A1-$R^6$(i)). Such subgeneric embodiments within the A2 Group of compounds include the A2 group in combination with each of the $R^6$ groups (i.e. A2-$R^6$(a), A2-$R^6$(b), A2-$R^6$(c), A2-$R^6$(d), A2-$R^6$(e), A2-$R^6$(f), A2-$R^6$(g), A2(g), A2-$R^6$(h) and A2-$R^6$(i)). Such subgeneric embodiments within the A3 Group of compounds include the A3 group in combination with each of the $R^6$ groups (i.e. A3-$R^6$(a), A3-$R^6$(b), A3-$R^6$(c), A3-$R^6$(d), A3-$R^6$(f), A3-$R^6$(g), A3-$R^6$(h) and A3-$R^6$(i)). Such subgeneric embodiments within the A4 Group of compounds include the A4 group in combination with each of the $R^6$ groups (i.e. A4-$R^6$(a), A4-$R^6$(b), A4-$R^6$(c), A4-$R^6$(d), A4-$R^6$(e), A4-$R^6$(f), A4-$R^6$(g), A4-$R^6$(h), and A4-$R^6$(i)). Such subgeneric embodiments within the A5 Group of compounds include the A5 group in combination with each of the $R^6$ groups (i.e. A5-$R^6$(a), A5-$R^6$(b), A5-$R^6$(c), A5-$R^6$(d), A5-$R^6$(e), A5-$R^6$(f), A5-$R^6$(g), A5-$R^6$(h) and A5-$R^6$(i)). Such subgeneric embodiments within the A6 Group of compounds include the A6 group in combination with each of the $R^6$ groups (i.e. A6-$R^6$(a), A6-$R^6$(b), A6-$R^6$(c), A6-$R^6$(d), A6-$R^6$(e), A6-R-$^6$(f), A6-$R^6$(g), A6-$R^6$(h) and A6-$R^6$(i)). Such subgeneric embodiments within the A7 Group of compounds include the A7 group in combination with each of the R6 groups (i.e. A7-$R^6$(a), A7-$R^6$(b), A7-$R^6$(c), A7-$R^6$(d), A7-$R^6$(e), A7-$R^6$(f), A7-$R^6$(g), A7-$R^6$(h) and A7-$R^6$(i)). Such subgeneric embodiments within the A8 Group of compounds include the A8 group in combination with each of the $R^6$ groups (i.e. A8-$R^6$(a), A8-$R^6$(b), A8-$R^6$(c), A8-$R^6$(d), A8-$R^6$(e), A8-$R^6$(f), A8-$R^6$(g), A8-$R^6$(h) and A8-$R^6$(i)). Such subgeneric embodiments within the A9 Group of compounds include the A9 group in combination with each of the R6 groups (i.e. A9-$R^6$(a), A9-$R^6$(b), A9-$R^6$(c), A9-R6(d), A9-$R^6$(e), A9-$R^6$(f), A9-$R^6$(g), A9-$R^6$(h) and A9-$R^6$(i)). Such subgeneric embodiments within the A10 Group of compounds include the A10 group in combination with each of the $R^6$ groups (i.e. A10-$R^6$(a), A10-$R^6$(b), A10-$R^6$(c), A10-$R^6$(d), A10-$R^6$(e), A10-$R^6$(f), A10-$R^6$(g), A10-$R^6$(h) and A10-$R^6$(i)).

Preferred compounds of formula 1 are those compounds wherein the "A" ring is optionally substituted pyridin-2-yl or pyridin-3-yl; more preferably wherein m is 2.

Other preferred compounds of this invention are those of the formula (I) wherein $R^6$ is phenyl optionally substituted by 1–3 substituents independently selected from the group consisting of halo, hydroxy, cyano, mercapto, HO—(C=O)—, nitro, $(C_1-C_6)$alkyl, $(C_2-C_6)$alkenyl, $(C_1-C_6)$ alkoxy, $(C_1-C_6)$alkyl-S—, amino, $(C_1-C_6)$alkylamino, di[(C$_1$–C$_6$)alkyl]amino, amido, (C$_1$–C$_6$)alkylamido, di[(C$_1$–C$_6$)alkyl]amido, (C$_1$–C$_6$)alkyl-(C=O)—O—, (C$_1$–C$_6$)alkyl-(C=O)—N(R')—, formyl, (C$_1$–C$_6$)alkyl-(C=O)— and (C$_1$–C$_6$)alkoxy-(C=O)—; wherein R' is hydrogen or (C$_1$–C$_6$)alkyl; wherein each of said (C$_1$–C$_6$) alkyl is optionally substituted with 1 to 3 substituents independently selected from the group consisting of halo, hydroxy, cyano, mercapto, HO—(C=O)—, nitro, (C$_1$–C$_6$) alkyl, (C$_2$–C$_6$)alkenyl, (C$_1$–C$_6$)alkoxy, (C$_1$–C$_6$)alkyl-S—, amino, (C$_1$–C$_6$)alkylamino, di[(C$_1$–C$_6$)alkyl]amino, amido, (C$_1$–C$_6$)alkylamido, di[(C$_1$–C$_6$)alkyl]amido, (C$_1$–C$_6$)alkyl-(C=O)—O—, (C$_1$–C$_6$)alkyl-(C=O)—N(R')—, formyl, (C$_1$–C$_6$)alkyl-(C=O)— and (C$_1$–C$_6$)alkoxy-(C=O)—.

Other preferred compounds of this invention are those of the formula (I) wherein R$^6$ is cyclohexyl optionally substituted by 1 substituent independently selected from the group consisting of halo, hydroxy, cyano, mercapto, HO—(C=O)—, nitro, (C$_1$–C$_6$)alkyl, (C$_2$–C$_6$)alkenyl, (C$_1$–C$_6$) alkoxy, (C$_1$–C$_6$)alkyl-S—, amino, (C$_1$–C$_6$)alkylamino, di[(C$_1$–C$_6$)alkyl]amino, amido, (C$_1$–C$_6$)alkylamido, di[(C$_1$–C$_6$)alkyl]amido, (C$_1$–C$_6$)alkyl-(C=O)—O—, (C$_1$–C$_6$)alkyl-(C=O)—N(R')—, formyl, (C$_1$–C$_6$)alkyl-(C=O)— and (C$_1$–C$_6$)alkoxy-(C=O)—; wherein R' is hydrogen or (C$_1$–C$_6$)alkyl; wherein each of said (C$_1$–C$_6$) alkyl is optionally substituted with 1 to 3 substituents independently selected from the group consisting of halo, hydroxy, cyano, mercapto, HO—(C=O)—, nitro, (C$_1$–C$_6$) alkyl, (C$_2$–C$_6$)alkenyl, (C$_1$–C$_6$)alkoxy, (C$_1$–C$_6$)alkyl-S—, amino, (C$_1$–C$_6$)alkylamino, di[(C$_1$–C$_6$)alkyl]amino, amido, (C$_1$–C$_6$)alkylamido, di[(C$_1$–C$_6$)alkyl]amido, (C$_1$–C$_6$)alkyl-(C=O)—O—, (C$_1$–C$_6$)alkyl-(C=O)—N(R')—, formyl, (C$_1$–C$_6$)alkyl-(C=O)— and (C$_1$–C$_6$)alkoxy-(C=O)—.

Other preferred compounds of this invention are those of the formula (I) wherein R$^2$ is hydrogen, halo (more preferably chloro or fluoro, most preferably fluoro) or (C$_1$–C$_6$) alkyl, more preferably wherein R$^2$ is methyl or hydrogen.

Other preferred compounds of this invention are those of the formula (I) wherein R$^3$ is cyano or (C$_1$–C$_6$)alkyl optionally substituted with one to three halo atoms, more preferably wherein R$^3$ is —CF$_3$ or —CF$_2$H.

Other preferred compounds of this invention are those of the formula (I) wherein R$^4$ is methyl.

Examples of specific preferred compounds of the formula I are the following:

2-[5-(4-Bromo-phenyl)-3-trifluoromethyl-pyrazol-1-yl]-5-methanesulfonyl-pyridine;
{4-[2-(6-Methanesulfonyl-pyridin-3-yl)-5-trifluoromethyl-2H-pyrazol-3-yl]-phenyl}-dimethyl-amine;
{4-[2-(5-Methanesulfonyl-pyridin-2-yl)-5-trifluoromethyl-2H-pyrazol-3-yl]-phenyl}-dimethyl-amine;
2-[3-Difluoromethyl-5-(3-fluoro-4-methoxy-phenyl)-pyrazol-1-yl]-5-methanesulfonyl-pyridine;
2-[5-(3-Bromo-4-methoxy-phenyl)-3-trifluoromethyl-pyrazol-1-yl]-5-methanesulfonyl-pyridine;
2-[5-(3-Chloro-4-methoxy-phenyl)-3-trifluoromethyl-pyrazol-1-yl]-5-methanesulfonyl-pyridine;
2-(3-Difluoromethyl-5-p-tolyl-pyrazol-1-yl)-5-methanesulfonyl-pyridine;
5-Methanesulfonyl-2-(5-o-tolyl-3-trifluoromethyl-pyrazol-1-yl)-pyridine;
5-Methanesulfonyl-2-(5-phenyl-3-trifluoromethyl-pyrazol-1-yl)-pyridine;
2-[5-(3-Chloro4-methoxy-phenyl)-3-difluoromethyl-pyrazol-1-yl]-5-methanesulfonyl-pyridine;
2-(5-(3-Fluoro-4-methoxy-phenyl)-3-trifluoromethyl-pyrazol-1-yl]-5-methanesulfonyl-pyridine;
5-Methanesulfonyl-2-[5-(4-methoxy-3-methyl-phenyl)-3-trifluoromethyl-pyrazol-1-yl]-pyridine;
2-[3-Difluoromethyl-5-(4-methoxy-3-methyl-phenyl)-pyrazol-1-yl]-5-methanesulfonyl-pyridine;
2-[5-(2,3-Dihydro-benzo[1,4]dioxin-6-yl)-3-trifluoromethyl-pyrazol-1-yl]-5-methanesulfonyl-pyridine;
2-(5-Benzo[1,3]dioxol-5-yl-3-trifluoromethyl-pyrazol-1-yl-5-methanesulfonyl-pyridine;
2-[5-(2-Fluoro-4-methoxy-phenyl)-3-trifluoromethyl-pyrazol-1-yl]-5-methanesulfonyl-pyridine;
2-[3-Difluoromethyl-5-(2-fluoro-4-methoxy-phenyl)-pyrazol-1-yl]-5-methanesulfonyl-pyridine;
2-[3-Difluoromethyl-5(3,4-dimethyl-phenyl)-pyrazol-1-yl]-5-methanesulfonyl-pyridine;
2-(5-(4-Chloro-phenyl-3-trifluoromethyl-pyrazol-1-yl]-5-methanesulfonyl-pyridine;
2-[5-(4-Fluoro-phenyl)-3-trifluoromethyl-pyrazol-1-yl]-5-methanesulfonyl-pyridine;
2-[5-(4-Chloro-3-methyl-phenyl)-3-trifluoromethyl-pyrazol-1-yl]-5-methanesulfonyl-pyridine;
2-(3-Difluoromethyl-5-phenyl-pyrazol-1-yl)-5-methanesulfonylpyridine;
2-[3-Difluoromethyl-5-(4-fluoro-phenyl)-pyrazol-1-yl]-5-methanesulfonyl-pyridine;
5-Methanesulfonyl-2-[5-(6-methyl-naphthalen-2-yl)-3-trifluoromethyl-pyrazol-1-yl]-pyridine;
2-(5-Cyclohexyl-3-difluoromethyl-pyrazol-1-yl )-5-methanesulfonyl-pyridine;
2-[3-Difluoromethyl-5-(2-fluoro-phenyl)-pyrazol-1-yl]-5-methanesulfonyl-pyridine;
2-(4-Chloro-5-phenyl-3-trifluoromethyl-pyrazol-1-yl)-5-methanesulfonyl-pyridine; and
2-(5-Cyclohexyl-3-trifluoromethyl-pyrazol-1-yl)-5-methanesulfonyl-pyridine.

Other compounds of formula I include the following:
5-[3-Difluoromethyl-5-(3-fluoro-4-methoxy-phenyl)-pyrazol-1-yl]-2-methanesulfonyl-pyridine;
2-(5-(4-Bromo-phenyl)-3-trifluoromethyl-pyrazol-1-yl]-5-methanesulfonyl-pyridine;
4-[2-(5-Methanesulfonyl-pyridin-2-yl)-5-trifluoromethyl-2H-pyrazol-3-yl)-N-methyl-benzamide;
{4-[2-(6-Methanesulfonyl-pyridin-3-yl)-5-trifluoromethyl-2H-pyrazol-3-yl]-phenyl}-dimethyl-amine;
2-Methanesulfonyl-5-(5-p-tolyl-3-trifluoromethyl-pyrazol-1-yl)-pyridine;
{4-[2-(5-Methanesulfonyl-pyridin-2-yl)-5-trifluoromethyl-2H-pyrazol-3-yl]-phenyl}-dimethyl-amine;
2-[3-Difluoromethyl-5-(3-fluoro-4-methoxy-phenyl)-pyrazol-1-yl]-5-methanesulfonyl-pyridine;
2-[5-(3-Bromo-4-methoxy-phenyl)-3-trifluoromethyl-pyrazol-1-yl]-5-methanesulfonyl-pyridine;
2-[5-(3-Chloro4-methoxy-phenyl)-3-trifluoromethyl-pyrazol-1-yl]-5-methanesulfonyl-pyridine;
5-Methanesulfonyl-2-(5-(4-methoxy-phenyl)-3-trifluoromethyl-pyrazol-1-yl]-pyridine;
2-(3-Difluoromethyl-5-p-tolyl-pyrazol-1-yl)-5-methanesulfonyl-pyridine;
2-[5-(4-Bromo-phenyl)3-difluoromethyl-pyrazol-1-yl]-5-methanesulfonyl-pyridine;
5-Methanesulfonyl-2-(5-o-tolyl-3-trifluoromethyl-pyrazol-1-yl)-pyridine;
5-Methanesulfonyl-2-(5-phenyl-3-trifluoromethyl-pyrazol-1-yl)-pyridine;
5-[5-(3-Chloro-4-methoxy-phenyl)-3-trifluoromethyl-pyrazol-1-yl]-2-methanesulfonyl-pyridine;
5-[5-(3-Fluoro-4-methoxy-phenyl)-3-trifluoromethyl-pyrazol-1-yl]-2-methanesulfonyl-pyridine;
5-[5-(4-Chloro-phenyl)-3-trifluoromethyl-pyrazol-1-yl]-2-methanesulfonyl-pyridine;

5-[5-(4-Fluoro-phenyl)-3-trifluoromethyl-pyrazol-1-yl]-2-methanesulfonyl-pyridine;
5-[5-(4-Chloro-phenyl)-3-difluoromethyl-pyrazol-1-yl]-2-methanesulfonyl-pyridine;
2-[5-(3-Chloro-4-methoxy-phenyl)-3-difluoromethyl-pyrazol-1-yl]-5-methanesulfonyl-pyridine;
2-[5-(3-Fluoro-4-methoxy-phenyl)-3-trifluoromethyl-pyrazol-1-yl]-5-methanesulfonyl-pyridine;
5-Methanesulfonyl-2-[5-(4-methoxy-3-methyl-phenyl)-3-trifluoromethyl-pyrazol-1-yl]-pyridine;
2-[3-Difluoromethyl-5-(4-methoxy-3-methyl-phenyl)-pyrazol-1-yl]-5-methanesulfonyl-pyridine;
2-Methanesulfonyl-5-(5-o-tolyl-3-trifluoromethyl-pyrazol-1-yl)-pyridine;
2-Methanesulfonyl-5-(5-phenyl-3-trifluoromethyl-pyrazol-1-yl)-pyridine;
5-[5-(2-Chloro-phenyl)-3-trifluoromethyl-pyrazol-1-yl]-2-methanesulfonyl-pyridine;
2-Methanesulfonyl-5-[5-(4-methylsulfanyl-phenyl)-3-trifluoromethyl-pyrazol-1-yl]-pyridine;
2-[5-(4-Chloro-phenyl)-3-difluoromethyl-pyrazol-1-yl]-5-methanesulfonyl-pyridine;
2-[5-(2,4-Dimethyl-phenyl)-3-trifluoromethyl-pyrazol-1-yl]-5-methanesulfonyl-pyridine;
5-Methanesulfonyl-2-(5-naphthalen-2-yl-3-trifluoromethyl-pyrazol-1-yl)-pyridine;
2-[5-(2,3-Dihydro-benzo[1,4]dioxin-6-yl)-3-trifluoromethyl-pyrazol-1-yl]-5-methanesulfonyl-pyridine;
5-Methanesulfonyl-2-[3-trifluoromethyl-5-(3,4,5-trimethoxy-phenyl)-pyrazol-1-yl]-pyridine;
3-[2-(5-Methanesulfonyl-pyridin-2-yl)-5-trifluoromethyl-2H-pyrazol-3-yl]-benzonitrile;
2-(5-Biphenyl-4-yl-3-trifluoromethyl-pyrazol-1-yl)-5-methanesulfonyl-pyridine;
2-Methanesulfonyl-5-[5-(4-methoxy-3-methyl-phenyl)-3-trifluoromethyl-pyrazol-1-yl]-pyridine;
5-[3-Difluoromethyl-5-(4-methoxy-3-methyl-phenyl)-pyrazol-1-yl]-2-methanesulfonyl-pyridine;
2-(5-Benzo[1,3]dioxol-5-yl-3-trifluoromethyl-pyrazol-1-yl)-5-methanesulfonyl-pyridine;
2-(5-Benzo[1,3]dioxol-5-yl-3-difluoromethyl-pyrazol-1-yl)-5-methanesulfonyl-pyridine;
2-[5-(2-Fluoro-4-methoxy-phenyl)-3-trifluoromethyl-pyrazol-1-yl]-5-methanesulfonyl-pyridine;
2-[3-Difluoromethyl-5-(2-fluoro-4-methoxy-phenyl)-pyrazol-1-yl]-5-methanesulfonyl-pyridine;
2-[5-(3,4-Dimethyl-phenyl)-3-trifluoromethyl-pyrazol-1-yl]-5-methanesulfonyl-pyridine;
2-[3-Difluoromethyl-5-(3,4-dimethyl-phenyl)pyrazol-1-yl]-5-methanesulfonyl-pyridine;
2-[5-(2,3-Dihydro-benzofuran-6-yl)-3-trifluoromethyl-pyrazol-1-yl]-5-methanesulfonyl-pyridine;
2-[5-(3,5-Difluoro-phenyl)-3-trifluoromethyl-pyrazol-1-yl]-5-methanesulfonyl-pyridine;
2-[5-(4-tert-Butyl-phenyl)-3-trifluoromethyl-pyrazol-1-yl]-5-methanesulfonyl-pyridine;
2-(3,5-Diphenyl-pyrazol-1-yl)-5-methanesulfonyl-pyridine;
4-[2-(5-Methanesulfonyl-pyridin-2-yl)-5-trifluoromethyl-2H-pyrazol-3-yl]-benzonitrile;
1-(5-Methanesulfonyl-pyridin-2-yl)-5-methyl-3-trifluoromethyl-4,5-dihydro-1H-benzo[g]indazole;
1-(5-Methanesulfonyl-pyridin-2-yl)-8-methoxy-3-trifluoromethyl-4,5-dihydro-1H-benzo[g]indazole;
1-(5-Methanesulfonyl-pyridin-2-yl)-3-trifluoromethyl-4,5-dihydro-1H-benzo[g]indazole;
2-[2-(5-Methanesulfonyl-pyridin-2-yl)-5-trifluoromethyl-2H-pyrazol-3-yl]-pyrazine;
2-(3-Difluoromethyl-5-naphthalen-2-yl-pyrazol-1-yl)-5-methanesulfonyl-pyridine;
5-Methanesulfonyl-2-[5-(1-methanesulfonyl-piperidin-4-yl)-3-trifluoromethyl-pyrazol-1-yl]-pyridine;
2-[5-(3-Chloro-phenyl-3-trifluoromethyl-pyrazol-1-yl]-5-methanesulfonyl-pyridine;
2-{4-[2-(5-Methanesulfonyl-pyridin-2-yl)-5-trifluoromethyl-2H-pyrazol-3-yl]-piperidin-1-yl-}-benzothiazole;
3-Difluoromethyl-1-(5-methanesulfonyl-pyridin-2-yl)-7-methoxy-4,5-dihydro-1H-benzo[g]indazole;
5-[2-(5-Methanesulfonyl-pyridin-2-yl)-5trifluoromethyl-2H-pyrazol-3-yl]-pyrimidine;
2-(5-Cyclohexyl-3-difluoromethyl-pyrazol-1-yl)-5-methanesulfonyl-pyridine;
2-(5-Cyclohexyl-3-trifluoromethyl-pyrazol-1-yl)-5-methanesulfonyl-pyridine;
5-Methanesulfonyl-2-[4-methyl-3-trifluoromethyl-5-(2-trifluoromethyl-phenyl)-pyrazol-1-yl]-pyridine;
2-(5-Difluoromethyl-3-phenyl-pyrazol-1-yl)-5-methanesulfonyl-pyridine;
5-Methanesulfonyl-2-(4-methyl-5-phenyl-3-trifluoromethyl-pyrazol-1-yl)-pyridine;
5-Methanesulfonyl-2-(5-naphthalen-1-yl-3-trifluoromethyl-pyrazol-1-yl)pyridine;
5-[5-(4-Bromo-phenyl)-3-trifluoromethyl-pyrazol-1-yl]-2-methanesulfonyl-pyridine;
1-(6-Methanesulfonyl-pyridin-3-yl)-3-trifluoromethyl-4,5-dihydro-1H-benzo[g]indazole;
1-(5-Methanesulfonyl-pyridin-2-yl)-6-methoxy-3-trifluoromethyl-1,4-dihydro-indeno[1,2-c]pyrazole;
2-[3-Difluoromethyl-5-(2-fluoro-phenyl)-pyrazol-1-yl]-5-methanesulfonyl-pyridine;
2-[5-(2-Chloro-phenyl)-3-difluoromethyl-pyrazol-1-yl)-5-methanesulfonyl-pyridine;
2-(4-Chloro-5-phenyl-3-trifluoromethyl-pyrazol-1-yl)-5-methanesulfonyl-pyridine;
2-(4-Chloro-5-phenyl-pyrazol-1-yl)-5-methanesulfonyl-pyridine;
1-(5-Methanesulfonyl-pyridin-2-yl)-5-phenyl-1H-pyrazole-3-carboxylic acid;
4-Chloro-1-(5-methanesulfonyl-pyridin-2-yl)-5-phenyl-1H-pyrazole-3-carboxylic acid;
5-(5-Benzo[1,3]dioxol-5-yl-3-difluoromethyl-pyrazol-1-yl)-2-methanesulfonyl-pyridine;
5-[3-Difluoromethyl-5-(2-fluoro-4-methoxy-phenyl)-pyrazol-1-yl]-2-methanesulfonyl-pyridine;
5-[5-(3,4-Dimethyl-phenyl)-3-trifluoromethyl-pyrazol-1-yl]-2-methanesulfonyl-pyridine;
5-[3-Difluoromethyl-5-(3,4-dimethyl-phenyl)-pyrazol-1-yl]-2-methanesulfonyl-pyridine;
5-(5-Benzo[1,3]dioxol-5-yl-3-trifluoromethyl-pyrazol-1-yl)-2-methanesulfonyl-pyridine;
5-[5-(2-Fluoro-4-methoxy-phenyl)-3-trifluoromethyl-pyrazol-1-yl]-2-methanesulfonyl-pyridine;
2-Methanesulfonyl-5-(5-naphthalen-2-yl-3-trifluoromethyl-pyrazol-1-yl)-pyridine;
2-[5-(4-Chloro-phenyl)-3-trifluoromethyl-pyrazol-1-yl]-5-methanesulfonyl-pyridine;
2-[5-(4-Fluoro-phenyl)-3-trifluoromethyl-pyrazol-1-yl]-5-methanesulfonyl-pyridine;
2-[5-(2,5-Dichloro-phenyl)-3-trifluoromethyl-pyrazol-1-yl]-5-methanesulfonyl-pyridine;
2-[5-(4-Chloro-3-methyl-phenyl)-3-trifluoromethyl-pyrazol-1-yl]-5-methanesulfonyl-pyridine;
2-[5-(2,4-Dichloro-phenyl)-3-trifluoromethyl-pyrazol-1-yl]-5-methanesulfonyl-pyridine;

2-[3-(Chloro-difluoro-methyl)-5-(4-chloro-phenyl)-pyrazol-1-yl]-5-methanesulfonyl-pyridine;

5-Methanesulfonyl-2-[5-(4-methoxy-2-methyl-phenyl)-3-trifluoromethyl-pyrazol-1-yl]-pyridine;

2-[5-(3-Bromo-phenyl)-3-trifluoromethyl-pyrazol-1-yl]-5-methanesulfonyl-pyridine;

2-[5-(2-Fluoro-phenyl)-3-trifluoromethyl-pyrazol-1-yl]-5-methanesulfonyl-pyridine;

2-(5-(3,4-Dichloro-phenyl)-3-trifluoromethyl-pyrazol-1-yl]-5-methanesulfonyl-pyridine;

5-Methanesulfonyl-2-(5-phenyl-pyrazol-1-yl)-pyridine;

5-Methanesulfonyl-2-[5-(2-methyl-2,3-dihydro-benzofuran-6-yl)-3-trifluoromethyl-pyrazol-1-yl]-pyridine;

5-Methanesulfonyl-2-[5-(4-piperidin-1-yl-phenyl)-3-trifluoromethyl-pyrazol-1-yl]-pyridine;

2-[5-(4-Isobutyl-phenyl)-3-trifluoromethyl-pyrazol-1-yl]-5-methanesulfonyl-pyridine;

1-Ethyl-5-(2-(5-methanesulfonyl-pyridin-2-yl)5-trifluoromethyl-2H-pyrazol-3-yl]-2-methyl-1H-benzoimidazole;

5-Methanesulfonyl-2-[5-(5,6,7,8-tetrahydro-naphthalen-2-yl)-3-trifluoromethyl-pyrazol-1-yl]-pyridine;

5-Methanesulfonyl-2-[5-(4-trifluoromethoxy-phenyl)-3-trifluoromethyl-pyrazol-1-yl]-pyridine;

2-(3-Difluoromethyl-5-phenyl-pyrazol-1-yl)-5-methanesulfonylpyridine;

2-[3-Difluoromethyl-5-(4-fluoro-phenyl)-pyrazol-1-yl]-5-methanesulfonyl-pyridine;

5-Methanesulfonyl-2-[5-(6-methoxy-naphthalen-2-yl)-3-trifluoromethyl-pyrazol-1-yl]-pyridine;

5-Methanesulfonyl-2-[5-(6-methyl-naphthalen-2-yl)-3-trifluoromethyl-pyrazol-1-yl]-pyridine;

1-(5-Methanesulfonyl-pyridin-2-yl)-5-phenyl-1H-pyrazole-3-carboxylic acid methyl ester;

5-Methanesulfonyl-2-(5-p-tolyl-3-trifluoromethyl-pyrazol-1-yl)-pyridine;

4-[2-(5-Methanesulfonyl-pyridin-2-yl)-5-trifluoromethyl-2H-pyrazol-3-yl]-2-methyl-benzonitrile;

2-[5-(4-Bromo-3-methyl-phenyl)-4-ethyl-3-trifluoromethyl-pyrazol-1-yl]-5-methanesulfonyl-pyridine;

2-Chloro-4-[2-(6-methanesulfonyl-pyridin-3-yl)5-trifluoromethyl-2H-pyrazol-3-yl]-phenol;

5-[5-(4-Chloro-phenyl)-3-trifluoromethyl-pyrazol-1-yl]-2-methanesulfonyl-pyridine;

5-Methanesulfonyl-2-(5-phenyl-3-trifluoromethyl-pyrazol-1-yl)-pyrimidine;

2-[5-(2,3-Dihydro-benzofuran-5-yl)-3-trifluoromethyl-pyrazol-1-yl]-5-methanesulfonyl-pyrimidine;

5-Methanesulfonyl-2-(5-naphthalen-2-yl-3-trifluoromethyl-pyrazol-1-yl)-pyrimidine;

5-Methanesulfonyl-2-[5-(5,6,7,8-tetrahydro-naphthalen-2-yl)-3-trifluoromethyl-pyrazol-1-yl]-pyrimidine;

6-Methanesulfonyl-3-(5-phenyl-3-trifluoromethyl-pyrazol-1-yl)-[1,2,4]triazine;

3-[5-(2,3-Dihydro-benzofuran-5-yl)-3-trifluoromethyl-pyrazol-1-yl]-6-methanesulfonyl-[1,2,4]triazine;

6-Methanesulfonyl-3-(5-naphthalen-2-yl-3-trifluoromethyl-pyrazol-1-yl)-[1,2,4]triazine; and 6-Methanesulfonyl-3-[5-(5,6,7,8-tetrahydro-naphthalen-2-yl)-3-trifluoromethyl-pyrazol-1-yl]-[1,2,4]triazine.

The present invention also relates to a pharmaceutical composition for the treatment of a condition selected from the group consisting of arthritis (including osteoarthritis, degenerative joint disease, spondyloarthropathies, gouty arthritis, systemic lupus erythematosus, juvenile arthritis and rheumatoid arthritis), fever (including rheumatic fever and fever associated with influenza and other viral infections), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neuro-degenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, bums, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in cats), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock), and septic shock in a mammal, preferably a human, cat livestock or a dog, comprising an amount of a compound of formula I or a pharmaceutically acceptable salt thereof effective in such treatment and a pharmaceutically acceptable carrier.

The present invention also relates to a pharmaceutical composition for the treatment of a disorder or condition that can be treated by selectively inhibiting COX-2 in a mammal, preferably a human, cat, livestock or dog, comprising a COX-2 selective inhibiting effective amount of a compound of formula I or a pharmaceutically acceptable salt thereof and a pharmaceutically acceptable carrier.

The present invention also relates to a method for treating a condition selected from the group consisting of arthritis (including osteoarthritis, degenerative joint disease, spondyloarthropathies, gouty arthritis, systemic lupus erythematosus, juvenile arthritis and rheumatoid arthritis), fever (including rheumatic fever and fever associated with influenza and other viral infections), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neuro-degenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in cats), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock) and septic shock in a mammal, preferably a human, cat livestock or a dog, comprising administering to said mammal an amount of a compound of formula I or a pharmaceutically acceptable salt thereof effective in treating such a condition.

The present invention also relates to a method for treating a disorder or condition that can be treated or prevented by selectively inhibiting COX-2 in a mammal, preferably a human, cat livestock or a dog, comprising administering to a mammal requiring such treatment a COX-2 selective inhibiting effective amount of a compound of formula I or a pharmaceutically acceptable salt thereof.

This invention also relates to a method of or a pharmaceutical composition for treating inflammatory processes and diseases comprising administering a compound of formula I of this invention or its salt to a mammal including a human, cat, livestock or dog, wherein said inflammatory processes and diseases are defined as above, and said inhibitory compound is used in combination with one or more other therapeutically active agents under the following conditions:

A.) where a joint has become seriously inflamed as well as infected at the same time by bacteria, fungi, protozoa, and/or virus, said inhibitory compound is administered in combination with one or more antibiotic, antifungal, antiprotozoal, and/or antiviral therapeutic agents;

B.) where a multi-fold treatment of pain and inflammation is desired, said inhibitory compound is administered in combination with inhibitors of other mediators of inflammation, comprising one or more members independently selected from the group consisting essentially of:
(1) NSAIDs;
(2) $H_1$-receptor antagonists;
(3) kinin-$B_1$- and $B_2$-receptor antagonists;
(4) prostaglandin inhibitors selected from the group consisting of PGD-, PGF-$PGI_2$-, and PGE-receptor antagonists;
(5) thromboxane $A_2$ ($TXA_2$-) inhibitors;
(6) 5-, 12- and 15-lipoxygenase inhibitors;
(7) leukotriene $LTC_4$-, $LTD_4$/$LTE_4$-, and $LTB_4$- inhibitors;
(8) PAF-receptor antagonists;
(9) gold in the form of an aurothio group together with one or more hydrophilic groups;
(10) immunosuppressive agents selected from the group consisting of cyclosporine, azathioprine, and methotrexate;
(11) anti-inflammatory glucocorticoids;
(12) penicillamine;
(13) hydroxychloroquine;
(14) anti-gout agents including colchicine; xanthine oxidase inhibitors including allopurinol; and uricosuric agents selected from probenecid, sulfinpyrazone, and benzbromarone;

C. where older mammals are being treated for disease conditions, syndromes and symptoms found in geriatric mammals, said inhibitory compound is administered in combination with one or more members independently selected from the group consisting essentially of:
(1) cognitive therapeutics to counteract memory loss and impairment;
(2) anti-hypertensives and other cardiovascular drugs intended to offset the consequences of atherosclerosis, hypertension, myocardial ischemia, angina, congestive heart failure, and myocardial infarction, selected from the group consisting of:
  a. diuretics;
  b. vasodilators;
  c. β-adrenergic receptor antagonists;
  d. angiotensin-II converting enzyme inhibitors (ACE-inhibitors), alone or optionally together with neutral endopeptidase inhibitors;
  e. angiotensin II receptor antagonists;
  f. renin inhibitors;
  g. calcium channel blockers;
  h. sympatholytic agents;
  i. $\alpha_2$-adrenergic agonists;
  j. (α-adrenergic receptor antagonists; and
  k. HMG-CoA-reductase inhibitors (anti-hypercholesterolemics);
(3) antineoplastic agents selected from:
  a. antimitotic drugs selected from:
    i. vinca alkaloids selected from:
      [1] vinblastine, and
      [2] vincristine;
(4) growth hormone secretagogues;
(5) strong analgesics;
(6) local and systemic anesthetics; and
(7) $H_2$-receptor antagonists, proton pump inhibitors, and other gastroprotective agents.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "livestock animals" as used herein refers to domesticated quadrupeds, which includes those being raised for meat and various byproducts, e.g., a bovine animal including cattle and other members of the genus Bos, a porcine animal including domestic swine and other members of the genus Sus, an ovine animal including sheep and other members of the genus Ovis, domestic goats and other members of the genus Capra; domesticated quadrupeds being raised for specialized tasks such as use as a beast of burden, e.g., an equine animal including domestic horses and other members of the family Equidae, genus Equus, or for searching and sentinel duty, e.g., a canine animal including domestic dogs and other members of the genus Canis; and domesticated quadrupeds being raised primarily for recreational purposes, e.g., members of Equus and Canis, as well as a feline animal including domestic cats and other members of the family Felidae, genus Felis.

"Companion animals" as used herein refers to cats and dogs. As used herein, the term "dog(s)" denotes any member of the species *Canis familiaris*, of which there are a large number of different breeds. While laboratory determinations of biological activity may have been carried out using a particular breed, it is contemplated that the inhibitory compounds of the present invention will be found to be useful for treating pain and inflammation in any of these numerous breeds. Dogs represent a particularly preferred class of patients in that they are well known as being very susceptible to chronic inflammatory processes such as osteoarthritis and degenerative joint disease, which in dogs often results from a variety of developmental diseases, e.g., hip dysplasia and osteochondrosis, as well as from traumatic injuries to joints. Conventional NSAIDs, if used in canine therapy, have the potential for serious adverse gastrointestinal reactions and other adverse reactions including kidney and liver toxicity. Gastrointestinal effects such as single or multiple ulcerations, including perforation and hemorrhage of the esophagus, stomach, duodenum or small and large intestine, are usually debilitating, but can often be severe or even fatal.

The term "treating reproductive disorders (preferably in livestock)" as used herein refers to the use of the COX-2 inhibitors of the invention in mammals, preferably livestock animals (cattle, pigs, sheep, goats or horses), during the estrus cycle to control the time of onset of estrus by blocking the uterine signal for lysis of the corpus luteum, i.e. F-series prostaglandins, then removing the inhibition when the onset of estrus is desired. There are settings where it is useful to control or synchronize the time of estrus, especially when artificial insemination or embryo transfer are to be performed. Such use also includes enhancing the rate of embryo survival in pregnant livestock animals. Blocking F-series prostaglandin release can have several beneficial actions including reducing uterine contractions, enhancing uteroplacental bloodflow, supporting recognition of pregnancy, and postponing lysis of the corpus luteum at the time when estrus would have occurred had the animal not become pregnant (around Day 21 of pregnancy). Such treatment also abrogates the effects of stress on reproduction. For example reductions in fertility caused by excessive heat, negative energy balance and other stresses which have a COX-2 mediated component, as does abortion induced by stress such as heat, transportation, co-mingling, palpation, infection, etc. Such treatment is also useful to control the time of parturition, which is accompanied by release of F-series prostaglandins that lead to lysis of the corpus luteum. Inhibition of COX-2 would block the onset of premature labor in livestock animals, allowing the offspring time to mature before birth. Also there are settings where controlling the time of parturition is a useful tool for management of pregnant animals.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing prodrugs of compounds of the formula I. This invention also encompasses methods of treating or preventing disorders that can be treated or prevented by the selective inhibition of COX-2 comprising administering prodrugs of compounds of the formula I. Compounds of formula I having free amino, amido, hydroxy, carboxylic acid ester, sulfonamide or carboxylic groups (especially alkyl-S— and alkyl-(S=O)—) can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters are covalently bonded to the above substituents of formula I through the carbonyl carbon prodrug sidechain. Prodrugs also include metabolically labile groups such as ethers, acetates, mercaptans and sulfoxides.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies and TNF receptor immunoglobulin molecules (such as Enbrel®), low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The active ingredient of the present invention may be administered in combination with inhibitors of other mediators of inflammation, comprising one or more members selected from the group consisting essentially of the classes of such inhibitors and examples thereof which include, matrix metalloproteinase inhibitors, aggrecanase inhibitors, TACE inhibitors, leucotriene receptor antagonists, IL-1 processing and release inhibitors, ILra, $H_1$-receptor antagonists; kinin-$B_1$- and $B_2$-receptor antagonists; prostaglandin inhibitors such as PGD-, PGF-$PGI_2$-, and PGE-receptor antagonists; thromboxane $A_2$ (TXA2-) inhibitors; 5- and 12-lipoxygenase inhibitors; leukotriene $LTC_4$-, $LTD_4$/$LTE_4$-, and $LTB_4$-inhibitors; PAF-receptor antagonists; gold in the form of an aurothio group together with various hydrophilic groups; immunosuppressive agents, e.g., cyclosporine, azathioprine, and methotrexate; anti-inflammatory glucocorticoids; penicillamine; hydroxychloroquine; anti-gout agents, e.g., colchicine, xanthine oxidase inhibitors, e.g., allopurinol, and uricosuric agents, e.g., probenecid, sulfinpyrazone, and benzbromarone.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with anti-hypertensives and other cardiovascular drugs intended to offset the consequences of atherosclerosis, including hypertension, myocardial ischemia including angina, congestive heart failure, and myocardial infarction, selected from vasodilators such as hydralazine, β-adrenergic receptor antagonists such as propranolol, calcium channel blockers such as nifedipine, $α_2$-adrenergic agonists such as clonidine, α-adrenergic receptor antagonists such as prazosin, and HMG-CoA-reductase inhibitors (anti-hypercholesterolemics) such as lovastatin or atorvastatin.

The active ingredient of the present invention may also be administered in combination with one or more antibiotic, antifungal, antiprotozoal, antiviral or similar therapeutic agents.

The compounds of the present invention may also be used in combination with CNS agents such as antidepressants (such as sertraline), anti-Parkinsonian drugs (such as L-dopa, requip, mirapex, MAOB inhibitors such as selegine and rasagiline, comP inhibitors such as Tasmar, A-2 inhibitors, dopamine reuptake inhibitors, NMDA antagonists, nicotine agonists, dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, lasofoxifene, droloxifene or fosomax and immunosuppressant agents such as FK-506 and rapamycin.

The present invention also relates to the formulation of the active agents of the present invention alone or with one or more other therapeutic agents which are to form the intended combination, including wherein said different drugs have varying half-lives, by creating controlled-release forms of said drugs with different release times which achieves relatively uniform dosing; or, in the case of non-human patients, a medicated feed dosage form in which said drugs used in the combination are present together in admixture in said feed composition. There is further provided in accordance with the present invention co-administration in which the combination of drugs is achieved by the simultaneous administration of said drugs to be given in combination; including co-administration by means of different dosage forms and routes of administration; the use of combinations in accordance with different but regular and continuous dosing schedules whereby desired plasma levels of said drugs involved are maintained in the patient being treated, even though the individual rugs making up said combination are not being administered to said patient simultaneously.

DETAILED DESCRIPTION OF THE INVENTION

Compounds of the formula I may be prepared according to the following reaction schemes and discussion. Unless otherwise indicated, $R^2$ through $R^8$, A, X and m in the reaction schemes and discussion that follow are as defined above.

SCHEME 1

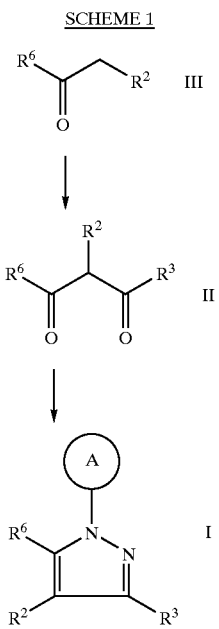

SCHEME 2
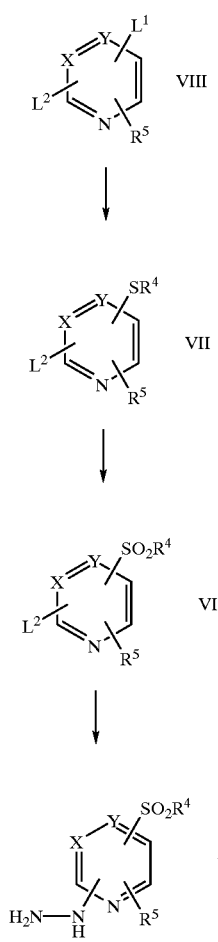
SCHEME 3
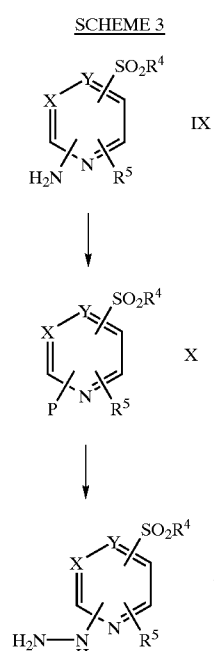
SCHEME 4
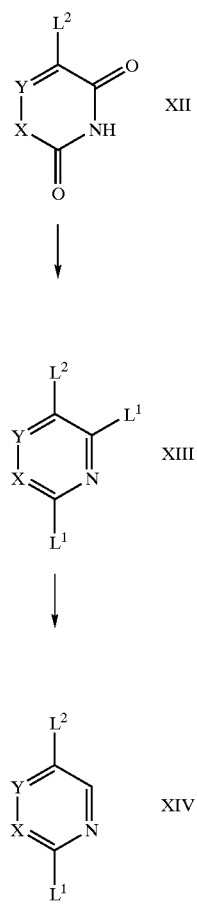
SCHEME 5
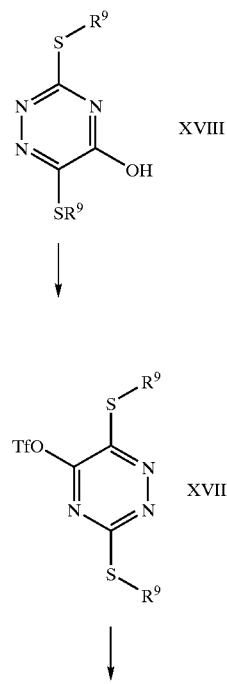

-continued

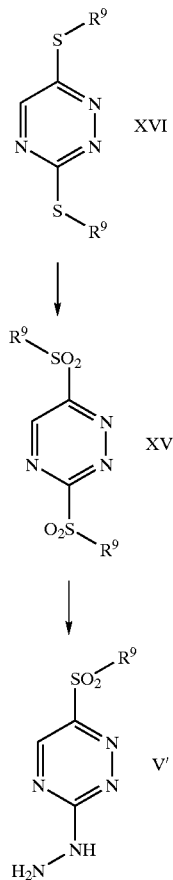

Scheme 1 illustrates a method of synthesizing compounds of the formula I. Referring to Scheme 1, a compound of the formula I is prepared from a compound of formula II by reaction with a compound of the formula

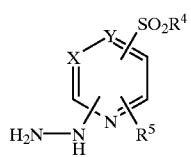

under acidic, neutral or basic conditions, preferably in the presence of acid or the acid salt of the compound of formula V in a suitable solvent or solvent mixture. Suitable solvents include alcohols, such as ethanol, trifluoroethanol, methanol, propanol, isopropanol or butanol; dimethyl sulfoxide (DMSO), N,N-dimethylformamide (DMF), N,N-dimethylacetamide (DMA), N-methyl-2-pyrrolidinone (NMP), benzene, toluene or chloroform, preferably an alcohol, most preferably ethanol or isopropanol. Preferred acids are hydrochloric acid, acetic acid, trifluoroacetic acid, p-toluenesulfonic acid and sulfuric acid. This reaction is generally carried out at a temperature from about 0° C. to about 140° C., preferably at about the reflux temperature of the polar solvent.

The compound of formula II is prepared from a compound of the formula III by reaction with a compound of the formula

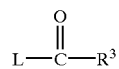

wherein L is a leaving group, in the presence of a base and a solvent. Suitable reagents of formula IV include ester or ester equivalents such as acylimidazole, dialkylamide, dialkylacetal, halides and thioesters, preferably acylimidazole. Suitable bases include potassium carbonate ($K_2CO_3$), sodium carbonate ($Na_2CO_3$), sodium hydride (NaH), sodium methoxide, potassium-tert.-butoxide, lithium diisopropylamide, pyrrolidine and piperidine, preferably sodium methoxide. These reactions can be carried out in a solvent such as di-(alkyl)ether (preferably dimethoxyethane), tetrahydrofuran (THF), methanol, dichloromethane, methyl tert-butyl ether, dimethylformamide (DMF), dimethylacetamide (DMA) or DMSO, preferably dimethoxyethane. Reaction temperatures can range from about 0° C. to about 150° C., preferably from about 20° C. to about 25° C.

Compounds of formula III are commercially available or can be made by methods well known to those of ordinary skill in the art. Compounds of formula III can be prepared by the methods described in *Aust. J. Chem.*, 1977, 30 , 229 and *Heterocycles*, 1990, 31, 1951 and methods which are incorporated by reference. The regio isomeric pyrazole (Ia') can be also prepared from the corresponding 1,3-diketone and an appropriate heteroaryl hydrazine according to other methods well known in the art.

Scheme 2 refers to the preparation of compounds of the formula V in a multi-step process from compounds of the formula VIII, wherein $L^1$ and $L^2$ are leaving groups such as halo. Referring to Scheme 2, compounds of the formula V are prepared from compounds of the formula VI by reaction with hydrazine (preferably anhydrous) in the presence of a polar solvent. Suitable solvents include alcohols, such as ethanol, methanol, propanol or butanol; dimethyl sulfoxide (DMSO), N,N-dimethylformamide (DMF), N,N-dimethylacetamide (DMA) or N-methyl-2-pyrrolidinone (NMP), preferably an alcohol, most preferably ethanol. This reaction is generally carried out at a temperature from about 0° C. to about 140° C., preferably at about the reflux temperature of the polar solvent. Preferably the product is isolated as a salt, such as a hydrobromide or hydrochoride salt. The hydrochloride salt is preferred.

The compound of formula VI is prepared from a compound of the formula VII by reaction with an oxidizing reagent in the presence of a solvent. Suitable oxidants include meta-chloroperbenzoic acid, hydrogen peroxide, sodium perborate, or Oxone®. Suitable solvents or solvent mixtures include methanol-water, dioxane-water, tetrahydrofuran-water, methylene chloride, or chloroform, preferably methanol-water. Suitable temperatures for the aforesaid reaction range from about 0° C. to about 60° C., preferably the temperature may range from about 20° C. to about 25° C. (i.e. room temperature). The reaction is complete within about 0.5 hours to about 24 hours, preferably about 16 hours.

The compound of the formula VII is prepared from a compound of formula VIII by nucleophilic substitution reaction using a sulfur nucleophilic reagent such as alkylthiols, dialkyldisulfide, alkylsulfonate, sodium thioalkoxide or potassium thioalkoxide, in the presence or absence of a base in a polar solvent. Suitable bases include sodium hydroxide, triethylamine; alkyllithiums such as n-butyllithium, sec-butyllithium, and tert-butyllithium; and lithium diisopropylamide, and suitable solvents include ethers such as dimethylether; alkanols such as methanol, ethanol and tert-butanol; a mixture of an alkanol and water; THF; benzene; toluene; xylene; DMF; DMSO; dioxane; and 1,2-dimethoxyethane. This reaction is generally carried out at a temperature from about −78° C. to 200° C. for from about 1 minute to 1 day.

Alternatively, compounds of the formula V may also be prepared from a compound of the formula IX by nitrosation followed by reduction as illustrated in Scheme 3. Referring to Scheme 3, a compound of the formula V is prepared by reacting a compound of formula X, wherein P is —NH—NO or —N≡N$^+$, with a reducing agent or catalytic hydrogenation in an inert solvent. Suitable reducing agents include metal halides such as $TiCl_3$, $SnCl_2$, zinc powder-acetic acid, sodium-ethanol, sodium-aqueous ammonia, lithium aluminum hydride and the like. Catalytic hydrogenation may be carried out using a catalyst such as palladium on carbon (Pd/C), palladium on barium sulfate (Pd/$BaSO_4$), platinum on carbon (Pt/C), or tris(triphenylphosphine) rhodium chloride (Wilkinson's catalyst), in an appropriate solvent such as methanol, ethanol, THF, dioxane or ethyl acetate, at a pressure from about 1 to about 5 atmospheres and a temperature from about 10° C. to about 60° C. The following conditions are preferred: Pd on carbon, methanol at 25° C. and 50 psi of hydrogen gas pressure. This method also provides for introduction of hydrogen isotopes (i.e., deuterium, or tritium) by replacing $^1H_2$ with $^2H_2$ or $^3H_2$ in the above procedure. Compounds of formula V thus obtained may be isolated as an acid addition salt such as hydrochloride.

A compound of the formula X, wherein P is —NH—NO or —N≡N$^+$, can be prepared by reaction of a compound of the formula IX with a suitable reagent. Typical reagents include sodium nitrite in an aqueous medium (e.g., hydrochloric acid in water); others include nitrosyl chloride, nitrogen oxides and nitrite ethers. This reaction is typically carried out at about 0° C. for about 1 minute to 10 hours.

Compounds of formula IX are commercially available or can be prepared by methods well known to those of ordinary skill in the art (e.g., F. Walker et al., J. Chem. Soc. 1939, 1948).

Compounds of the formula V may be also prepared according to known methods disclosed in *Collection Czechoslov. Chem. Common. Vol.* 37, p. 1721, 1972 by J. Vavrina et al.

Scheme 4 illustrates preparation methods for synthesizing compounds of formula XIV (i.e., pyrimidine compounds of formula VIII which can be used in Scheme 2) wherein X and Y are independently NH or $CR^8$; and both $L^1$ and $L^2$ are leaving groups. Referring to Scheme 4, a diketone compound of formula XII may be subjected to substitution reaction to introduce $L^1$ to give the compound of formula XIII followed by reduction to give the compound of formula XIV. A typical leaving group is halo, which can be introduced by halogenation according to methods known in the art. For example, chlorination of a compound of formula XII can be carried out using a chlorinating reagent such as an excess amount of phosphoryl chloride in the presence or absence of a base such as N,N-diethylaniline. This reaction can typically be carried out under reflux for from about 30 minutes to about 10 hours. The subsequent reduction may be carried out using a reducing reagent such as a metal catalyst in the presence of a base in a reaction inert solvent according to known methods in the art. For example, this reaction can typically be carried out using zinc powder in the presence of ammonia in a reaction inert solvent such as benzene at about room temperature for from about 1 hour to about 1 day. Compounds of formula XIV thus obtained can be subjected to the reactions illustrated in Scheme 2.

Compounds of the formula XII are commercially available or can be made by methods well known to those of ordinary skill in the art. See for example *Pharmazie*, 17, 135 (1961), *Pharmazie*, 17, 209 (1962) and *J.O.C.*, 63, 6329 (1998).

Scheme 5 illustrates the methods for preparing compounds of formula V', wherein $R^9$ is alkyl, which can be converted to compounds of the formula I according to Scheme 1. Referring to Scheme 5, a compound of formula V' is prepared from a compound of formula XV by reaction with hydrazine in a polar solvent. Suitable solvents include alcohols, such as ethanol, methanol, propanol or butanol; dimethyl sulfoxide (DMSO), N,N-dimethylformamide (DMF), N,N-dimethylacetamide (DMA) or N-methyl-2-pyrrolidinone (NMP), preferably an alcohol, most preferably ethanol. This reaction is generally carried out at a temperature from about 0° C. to about 140° C., preferably at about the reflux temperature of the polar solvent. Preferably the product is isolated as a salt, such as a hydrobromide or hydrochoride salt. The hydrochloride salt is preferred.

The compound of formula XV can be prepared from a compound of formula XVI by reaction with an oxidizing reagent in the presence of a solvent. Suitable solvents or solvent mixtures include methanol-water, dioxane-water, tetrahydrofuran-water, methylene chloride, or chloroform, preferably methanol-water. Suitable temperatures for the aforesaid reaction range from about 0° C. to about 60° C., preferably the temperature may range from about 20° C. to about 25° C. (i.e. room temperature). The reaction is complete within about 0.5 hours to about 24 hours, preferably about 16 hours.

The compound of formula XVI is prepared from a compound of formula XVII by reaction with a hydride reagent in a solvent. Suitable hydride reagents include sodiumborohydride or lithiumaluminumhydride. Suitable solvents include ether, THF, dimethylformamid, preferably ether. The aforementioned reaction is run at a temperature of about 0° C. to about 25° C., preferably about 0° C. The reaction is run for a period from about 5 minutes to about 2 hours.

The compound of formula XVII, wherein Tf is a leaving group such as $CF_3$—$SO_2$, is prepared from a compound of formula XVIII by reaction with an activating reagent in the presence of a base. Suitable activating agents include triflic anhydride or phosphorous oxychloride. Suitable solvents include pyridine. The aforementioned reaction is run at a temperature of about −20° C. to about 0° C. for a period from about 5 minutes to about 2 hours.

The compound of formula XVIII can be prepared by methods well known to those of ordinary skill in the art such as those described in *J. Org. Chem., Vol.* 63, p. 6329 (1998).

Other methods of preparing the compounds of Formula I are well known to those skilled in the art such as those described in *Heterocycles*, 31,1041 (1990). The compounds of formula (I) can also be synthesized by using the method of Kharash, Negishi, Stille, or Suzuki et. al., which are well known in the art. In general, aryl/heteroaryl compounds are synthesized by a number of catalytic cross-coupling reactions from aryl/heteroaryl halides or triflates and aryl/heteroaryl metal reagents, [for example, Grignard reagent (the so-called Kharasch reaction), aryl/heteroaryl zinc reagent (the so-called Negishi reaction), aryl/heteroaryl tin reagent (the so-called Stille reaction), arylboron reagent (the so-called Suzuki reaction), aryl/heteroaryl silyl reagent, etc. (see for example S. P. Stanforth, *Tetrahedron*, 1998, 54, 263–303].

Unless indicated otherwise, the pressure of each of the above reactions is not critical. Generally, the reactions will be conducted at a pressure of about one to about three atmospheres, preferably at ambient pressure (about one atmosphere).

Those skilled in the art will appreciate that the above schemes describe general methods for preparing the compounds of the invention. Specific compounds of formula I may possess sensitive functional groups that require protecting groups when prepared with the intermediates described. Examples of suitable protecting groups may be found in T. W. Greene and P. Wuts, *Protecting Groups in Organic Synthesis*, John Wiley & Sons, 2nd Edition, New York, 1991.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)-] salts.

Those compounds of the formula I which are also acidic in nature, e.g., wherein A or $R^6$ include a COOH or tetrazole or other acidic moiety, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

METHOD FOR ASSESSING BIOLOGICAL ACTIVITIES

The activity of the compounds of the formula (I) of the present invention was demonstrated by the following assays.

Human In vitro Assays

Human Cell-based COX-1 Assay

Human peripheral blood obtained from healthy volunteers was diluted to 1/10 volume with 3.8% sodium citrate solution. The platelet-rich plasma immediately obtained was washed with 0.14 M sodium chloride containing 12 mM Tris-HCl (pH 7.4) and 1.2 mM EDTA. Platelets were then washed with platelet buffer (Hanks buffer (Ca free) containing 0.2% BSA and 20 mM Hepes). Finally, the human washed platelets (HWP) were suspended in platelet buffer at the concentration of $2.85 \times 10^8$ cells/ml and stored at room temperature until use. The HWP suspension (70 µl aliquots, final $2.0 \times 10^7$ cells/ml) was placed in a 96-well U bottom plate and 10 µl aliquots of 12.6 mM calcium chloride added. Platelets were incubated with A23187 (final 10 µM, Sigma) with test compound (0.1–100 µM) dissolved in DMSO (final concentration; less than 0.01%) at 37° C. for 15 minutes. The reaction was stopped by addition of EDTA (final 7.7 mM) and TxB2 in the supernatant quantitated by using a radioimmunoassay kit (Amersham) according to the manufacturer's procedure.

Human Cell-based COX-2 Assay

The human cell based COX-2 assay was carried out as previously described (Moore et al., *Inflam. Res.*, 45, 54, 1996). Confluent human umbilical vein endothelial cells (HUVECs, Morinaga) in a 96-well flat bottom plate were washed with 80 ml of RPMI1640 containing 2% FBS and incubated with hIL-1β (final concentration 300 U/ml, R & D Systems) at 37° C. for 24 hours. After washing, the activated HUVECs were incubateed with test compound (final concentration; 0.1 nM–1 µM) dissolved in DMSO (final concentration; less than 0.01%) at 37° C. for 20 minutes and stimulated with A23187 (final concentration 30 mM) in Hanks buffer containing 0.2% BSA, 20 mM Hepes at 37° C. for 15 minutes. 6-Keto-PGF$_{1\alpha}$, stable metabolite of PGI2, in the supernatant was quantitated by using a radioimmunoassay method (antibody; Preseptive Diagnostics, SPA; Amersham).

Canine In vitro Assays

The following canine cell based COX 1 and COX-2 assays have been reported in Ricketts et al., *Evaluation of Selective Inhibition of Canine Cyclooxygenase 1 and 2 by Carprofen and Other Nonsteroidal Anti-inflammatory Drugs*, American Journal of Veterinary Research, 59 (11), 1441–1446.

Protocol for Evaluation of Canine COX-1 Activity

Test drug compounds were solubilized and diluted the day before the assay was to be conducted with 0.1 mL of DMSO/9.9 mL of Hank's balanced salts solution (HBSS), and stored overnight at 4° C. On the day that the assay was carried out, citrated blood was drawn from a donor dog, centrifuged at 190×g for 25 minutes at room temperature, and the resulting platelet-rich plasma was then transferred to a new tube for further procedures. The platelets were washed by centrifuging at 1500×g for 10 minutes at room temperature. The platelets were washed with platelet buffer comprising Hank's buffer (Ca free) with 0.2% bovine serum albumin (BSA) and 20 mM HEPES. The platelet samples were then adjusted to $1.5 \times 10^7$/mL, after which 50 µl of calcium ionophore (A23187) together with a calcium chloride solution were added to 50 µl of test drug compound dilution in plates to produce final concentrations of 1.7 µM A23187 and 1.26 mM Ca. Then, 100 µl of canine washed platelets were added and the samples were incubated at 37° C. for 15 minutes, after which the reaction was stopped by adding 20 µl of 77 mM EDTA. The plates were then centrifuged at 2000×g for 10 minutes at 4° C., after which 50 µl of supernatant was assayed for thromboxane B$_2$ (TXB$_2$) by enzyme-immunoassay (EIA). The pg/mL of TXB$_2$ was calculated from the standard line included on each plate, from which it was possible to calculate the percent inhibition of COX-1 and the $IC_{50}$ values for the test drug compounds.

Protocol for Evaluation of Canine COX-2 Activity

A canine histocytoma (macrophage-like) cell line from the American Type Culture Collection designated as DH82, was used in setting up the protocol for evaluating the COX-2 inhibition activity of various test drug compounds. There was added to flasks of these cells 10 μg/mL of LPS, after which the flask cultures were incubated overnight. The same test drug compound dilutions as described above for the COX-1 protocol were used for the COX-2 assay and were prepared the day before the assay was carried out. The cells were harvested from the culture flasks by scraping, and were then washed with minimal Eagle's media (MEM) combined with 1% fetal bovine serum, centrifuged at 1500 rpm for 2 minutes, and adjusted to a concentration of $3.2 \times 10^5$ cells/mL. To 50 μl of test drug dilution there was added 50 μl of arachidonic acid in MEM to give a 10 μM final concentration, and there was added as well 100 μl of cell suspension to give a final concentration of $1.6 \times 10^5$ cells/mL. The test sample suspensions were incubated for 1 hour and then centrifuged at 1000 rpm for 10 minutes at 4° C., after which 50 μl aliquots of each test drug sample were delivered to EIA plates. The EIA was performed for prostaglandin $E_2$ ($PGE_2$), and the pg/mL concentration of $PGE_2$ was calculated from the standard line included on each plate. From this data it was possible to calculate the percent inhibition of COX-2 and the $IC_{50}$ values for the test drug compounds. Repeated investigations of COX-1 and COX-2 inhibition were conducted over the course of several months. The results are averaged, and a single COX-1: COX-2 ratio is calculated.

Whole blood assays for COX-1 and COX-2 are known in the art such as the methods described in C. Brideau, et al., *A Human Whole Blood Assay for Clinical Evaluation of Biochemical Efficacy of Cyclooxygenase Inhibitors, Inflammation Research*, Vol. 45, pp. 68–74 (1996). These methods may be applied with feline, canine or human blood as needed.

In vivo Assays

Carrageenan Induced Foot Edema in Rats

Male Sprague-Dawley rats (5 weeks old, Charles River Japan) were fasted overnight. A line was drawn using a marker above the ankle on the right hind paw and the paw volume (V0) was measured by water displacement using a plethysmometer (Muromachi). Animals were given orally either vehicle (0.1% methyl cellulose or 5% Tween 80) or a test compound (2.5 ml per 100 g body weight). One hour later, the animals were then injected intradermally with λ-carrageenan (0.1 ml of 1% w/v suspension in saline, Zushikagaku) into right hind paw (Winter et al., *Proc. Soc. Exp. Biol. Med.*, 111, 544, 1962; Lombardino et al., *Arzneim. Forsch.*, 25, 1629, 1975) and three hours later, the paw volume (V3) was measured and the increase in volume (V3–V0) calculated. Since maximum inhibition attainable with classical NSAIDs is 60–70%, $ED_{30}$ values were calculated.

Gastric Ulceration in Rats

The gastric ulcerogenicity of test compound was assessed by a modification of the conventional method (Ezer et al., *J. Pharm. Pharmacol.*, 28, 655, 1976; Cashin et al., *J. Pharm. Pharmacol.*, 29, 330–336, 1977). Male Sprague-Dawley rats (5 weeks old, Charles River Japan), fasted overnight, were given orally either vehicle (0.1% methyl cellulose or 5% Tween 80) or a test compound (1 ml per 100 g body weight). Six hours after, the animals were sacrificed by cervical dislocation. The stomachs were removed and inflated with 1% formalin solution (10 ml). Stomachs were opened by cutting along the greater curvature. From the number of rats that showed at least one gastric ulcer or haemorrhaging erosion (including ecchymosis), the incidence of ulceration was calculated. Animals did not have access to either food or water during the experiment.

Canine Whole Blood Ex vivo Determinations of COX-1 and COX-2 Activity Inhibition The in vivo inhibitory potency of a test compound against COX-1 and COX-2 activity may be evaluated using an ex vivo procedure on canine whole blood. Three dogs were dosed with 5 mg/kg of the test compound administered by oral gavage in 0.5% methylcellulose vehicle and three dogs were untreated. A zero-hour blood sample was collected from all dogs in the study prior to dosing, followed by 2- and 8-hour post-dose blood sample collections. Test tubes were prepared containing 2 μL of either (A) calcium ionophore A23187 giving a 50 μM final concentration, which stimulates the production of thromboxane $B_2$ ($TXB_2$) for COX-1 activity determination; or of (B) lipopolysaccharide (LPS) to give a 10 μg/mL final concentration, which stimulates the production of prostaglandin $E_2$ ($PGE_2$) for COX-2 activity determination. Test tubes with unstimulated vehicle were used as controls. A 500 μL sample of blood was added to each of the above-described test tubes, after which they were incubated at 37° C. for one hour in the case of the calcium ionophore-containing test tubes, and overnight in the case of the LPS-containing test tubes. After incubation, 10 μL of EDTA was added to give a final concentration of 0.3%, in order to prevent coagulation of the plasma which sometimes occurs after thawing frozen plasma samples. The incubated samples were centrifuged at 4° C. and the resulting plasma sample of ~200 μL was collected and stored at −20° C. in polypropylene 96-well plates. In order to determine endpoints for this study, enzyme immunoassay (EIA) kits available from Cayman were used to measure production of $TXB_2$ and $PGE_2$, utilizing the principle of competitive binding of tracer to antibody and endpoint determination by colorimetry. Plasma samples were diluted to approximate the range of standard amounts which would be supplied in a diagnostic or research tools kit, i.e., 1/500 for $TXB_2$ and 1/750 for $PGE_2$.

The data set out in Table 2 below show how the percent inhibition of COX-1 and COX-2 activity is calculated based on their zero hour values. The data is expressed as treatment group averages in pg/ml of $TXB_2$ and $PGE_2$ produced per sample. Plasma dilution was not factored in said data values.

The data in Table 2 show that, in this illustration, at the 5 mg/kg dose there was significant COX-2 inhibition at both timepoints. The data in Table 2 also show that at the 5 mg/kg dose there was no significant inhibition of COX-1 activity at the timepoints involved. Accordingly, the data in Table 2 clearly demonstrates that at the 5 mg/kg dosage concentration this compound possesses good COX-2 selectivity.

TABLE 2

| | COX-1 ACTIVITY INHIBITION-Group Averages | | | | |
| --- | --- | --- | --- | --- | --- |
| | $TXB_2$ Pg/mL/Well | | | Percent Inhibition | |
| Hour | 0-hour | 2-hour | 8-hour | 2-hour | 8-hour |
| Untreated | 46 | 45 | 140 | 2% | 0% |
| 5 mg/kg | 41 | 38 | 104 | 7% | 0% |
| | COX-2 ACTIVITY INHIBITION-Group Averages | | | | |
| | $PGE_2$ Pg/mL/Well | | | Percent Inhibtion | |
| Hour | 0-hour | 2-hour | 8-hour | 2-hour | 8-hour |
| Untreated | 420 | 486 | 501 | 0% | 0% |
| 5 mg/kg | 711 | 165 | 350 | 77% | 51% |

COX inhibition is observed when the measured percent inhibition is greater than that measured for untreated controls. The percent inhibition in the above table is calculated in a straightforward manner in accordance with the following equation:

$$\% \text{ Inhibition (2-hour)} = \frac{(PGE_2 \text{ at } t = 0) - (PGE_2 \text{ at } t = 2)}{(PGE_2 \text{ at } t = 0)}$$

Data Analysis

Statistical program packages, SYSTAT (SYSTAT, INC.) and StatView (Abacus Cencepts, Inc.) for Macintosh were used. Differences between test compound treated group and control group were tested for using ANOVA. The $IC_{50}$ ($ED_{30}$) values were calculated from the equation for the log-linear regression line of concentration (dose) versus percent inhibition.

Most compounds prepared in the Working Examples as described hereinafter were tested by at least one of the methods described above, and showed $IC_{50}$ values of 0.001 $\mu$M to 3 $\mu$M with respect to inhibition of COX-2 in either the canine or human assays.

COX-2 selectivity can be determined by ratio in terms of $IC_{50}$ value of COX-1 inhibition to COX-2 inhibition. In general, it can be said that a compound showing a COX-2/COX-1 inhibition ratio of more than 5 has good COX-2 selectivity.

The compounds of the formula (I) of this invention can be administered via oral, parenteral, anal, buccal or topical routes to mammals (including humans, dogs, cats, horses and livestock).

In general, these compounds are most desirably administered to humans in doses ranging from 0.01 mg to 100 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of abovementioned diseases.

These compounds are most desirably administered to said non-human mammals, e.g. dogs, cats, horses or livestock in an amount, expressed as mg per kg of body weight of said member per day, ranging from about 0.01 mg/kg to about 20.0 mg/kg/day, preferably from about 0.1 mg/kg to about 12.0 mg/kg/day, more preferably from about 0.5 mg/kg to about 10.0 mg/kg/day, and most preferably from about 0.5 mg/kg to about 8.0 mg/kg/day.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various combinations thereof.

A preferred composition for dogs comprises an ingestible liquid peroral dosage form selected from the group consisting of a solution, suspension, emulsion, inverse emulsion, elixir, extract, tincture, and concentrate, optionally to be added to the drinking water of the dog being treated. Any of these liquid dosage forms, when formulated in accordance with methods well known in the art, can either be administered directly to the dog being treated, or may be added to the drinking water of the dog being treated. The concentrate liquid form, on the other hand, is formulated to be added first to a given amount of water, from which an aliquot amount may be withdrawn for administration directly to the dog or addition to the drinking water of the dog.

A preferred composition provides delayed-, sustained-, and/or controlled-release of said anti-inflammatory selective COX-2 inhibitor. Such preferred compositions include all such dosage forms which produce $\geq 80\%$ inhibition of COX-2 isozyme activity and result in a plasma concentration of said inhibitor of at least 3 fold the COX-2 $IC_{50}$ for at least 4 hours; preferably for at least 8 hours; more preferably for at least 12 hours; more preferably still for at least 16 hours; even more preferably still for at least 20 hours; and most preferably for at least 24 hours. Preferably, there is included within the above-described dosage forms those which produce $\geq 80\%$ inhibition of COX-2 isozyme activity and result in a plasma concentration of said inhibitor of at least 5 fold the COX-2 $IC_{50}$ for at least 4 hours, preferably for at least 8 hours, more preferably for at least 12 hours, still more preferably for at least 20 hours, and most preferably for at least 24 hours. More preferably, there is included the above-described dosage forms which produce $\geq 90\%$ inhibition of COX-2 isozyme activity and result in a plasma concentration of said inhibitor of at least 5 fold the COX-2 $IC_{50}$ for at least 4 hours, preferably for at least 8 hours, more preferably for at least 12 hours, still more preferably for at least 20 hours, and most preferably for at least 24 hours.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The compounds of formula (I) may also be administered in the form of suppositories for rectal or vaginal administration of the active ingredient. These compositions can be prepared by mixing the active ingredient with a suitable non-irritating excipient which is solid at room temperature (for example, 10° C. to 32° C.) but liquid at the rectal temperature and will melt in the rectum or vagina to release the active ingredient. Such materials are polyethylene glycols, cocoa butter, suppository and wax.

For buccal administration, the composition may take the form of tablets or lozenges formulated in conventional manner.

For transdermal administration, transdermal patches prepared in accordance with well known drug delivery technology may be prepared and applied to the skin of a mammal, preferably a human or a dog, to be treated, whereafter the active agent by reason of its formulated solubility characteristics migrates across the epidermis and into the dermal layers of the skin where it is taken up as part of the general circulation, ultimately providing systemic distribution of the active ingredient over a desired, extended period of time. Also included are implants which are placed beneath the epidermal layer of the skin, i.e. between the epidermis and the dermis of the skin of the patient being treated. Such an implant will be formulated in accordance with well known principles and materials commonly used in this delivery technology, and may be prepared in such a way as to provide controlled-, sustained-, and/or delayed-release of the active ingredient into the systemic circulation of the patient. Such subepidermal (subcuticular) implants provide the same facility of installation and delivery efficiency as transdermal patches, but without the limitation of being subject to degradation, damage or accidental removal as a consequence of being exposed on the top layer of the patient's skin.

EXAMPLES

The following examples contain detailed descriptions of the methods of the preparation of compounds of formula (I). These detailed descriptions fall within the scope of the invention and serve to exemplify the above described general synthetic procedures which form part of the invention. These detailed descriptions are presented for illustrative purposes only and are not intended to restrict the scope of the present invention.

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath of up to 60° C.; reactions were monitored by thin layer chromatography (tlc) and reaction times are given for illustration only; melting points (m.p.) given are uncorrected (polymorphism may result in different melting points); structure and purity of all isolated compounds were assured by at least one of the following techniques: tlc (Merck silica gel 60 F-254 precoated plates), mass spectrometry, nuclear magnetic resonance (NMR) or infrared spectroscopy (IR). IR data were obtained on a FTIR 8200 (SHIMAZU Spectrometer). Yields are given for illustrative purposes only. Flash column chromatography was carried out using Merck silica gel 60 (230–400 mesh ASTM). Low-resolution mass spectral data (EI) were obtained on a Automass 120 (JEOL) mass spectrometer. Liquid Chromatography data was collected on a Hewlett Packard 1100 Liquid Chromatography/Mass Selective Detector (LC/MSD). Analysis was performed on a Luna C-18 column with dimensions of 3.0×150 mm. The flow rate was 0.425 ml/minute running a gradient of 50% 0.1% aqueous formic acid and 50% acetonitrile to 100% acetonitrile in 15 minutes. The ionization type for the mass detector of the Mass Spectrophotometer was atmospheric pressure electrospray in the positive ion mode with a fragmentor voltage of 50 volts. NMR data was determined at 270 MHz (JEOL JNM-LA 270 spectrometer) using deuterated chloroform (99.8% D), methanol (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc.

The following abbrevation are used:

THF: tetrahydrofuran $CH_2Cl_2$: dichloromethane $NaHCO_3$: sodium bicarbonate

HCl: hydrogen chloride $MgSO_4$: magnesium sulfate $Na_2SO_4$: sodium sulfate

DME: dimethoxyethane n-BuLi: n-butyllithium

DMF: dimethylformamide

Example 1

2-[5-(2,3-DIHYDRO-BENZOFURAN-6-YL)-3-TRIFLUOROMETHYL-PYRAZOL-1-YL]-5-METHANESULFONYL-PYRIDINE

5-Hydrazino-2-(methylsulfonyl)pyridine hydrochloride (66 mg, 0.30 mmol) was added to a solution of 4,4,4-Trifluoro-1-[4-(benzodihydrofur-4-yl)butane-1,3-dione from Preparation 4 (0.91 mg, 0.35 mmol) in ethanol (3.5 mL). The mixture was heated at reflux temperature for 18 hours and cooled down to room temperature. The reaction mixture was concentrated in vacuo and the crude mixture was subjected to preparative thin layer chromatographic (TLC) (1000 um plate) purification with dichloromethane as eluant. The desired product was isolated after the band containing the product was washed with ethyl acetate and concentrated in vacuo to provide 40.7 mg of a white solid.

Example 2

5-METHANESULFONYL-2-(5-PHENYL-PYRAZOL-1-YL)-PYRIDINE

5-Hydrazino-2-(methylsulfonyl)pyridine hydrochloride (105.5 mg, 0.47 mmol) was added to a solution of 3-phenyl-2-propynal (commercially available)(73.3 mg, 0.56 mmol) in trifluoroethanol (3.5 mL). The mixture was heated at reflux temperature for 18 hours and cooled down to room temperature. The reaction mixture was concentrated in vacuo and the crude mixture was subjected to preparative thin layer chromatographic (TLC) (1000 um plate) purification with dichloromethane as eluant. The desired product was isolated after the band containing the product was washed with ethyl acetate and concentrated in vacuo to provide 28 mg of a pale white solid.

Example 3

2-[5-(2,4-Dichloro-phenyl)-3-trifluoromethyl-pyrazol-1-yl]-5-methanesulfonyl-pyridine To a mixture of the 2-hydrazino-5-(methylsulfonyl) pyridine (106 mg, 4.05 mmol) and 4,4,4-trifluoro-1-(2,4- dichlorophenyl)-1,3-butanedione (105 mg, 3.68 mmol) in dry trifluoroethanol (6 ml) was added a catalytic amount of concentrated sulfuric acid (about 0.25 ml) and the mixture was refluxed overnight. The reaction mixture was cooled to room temperature, concentrated, and diluted with water (25 ml) and neutralized with saturated NaHCO$_3$ to pH about 7 and then extracted with EtOAc (50ml×3). The organic layer was washed with brine (100 ml), dried (MgSO$_4$) and concentrated to give the crude solid. The solid was purified by flash chromatography eluting with ethyl acetate/hexane (1/4) to give the desired product as a white solid (134 mg, 83% yield).

Liquid chromatography yielded product eluting at 12.022 minutes with major mass spectra fragment peaks at 438.2, 436.2 and 400.2 AMU.

Example 4

4,4,4-TRIFLUORO-1-CYCLOHEXYL-1,3-BUTANEDIONE (STEP 1)

To a stirred solution of cyclohexylmethylketone (2.75 g, 21.8 mmol) in DME (200 mL) was added ethyl trifluoroacetate (7.79 ml, 65.4 mmol) and sodium methoxide (7.71 g, 131 mmol), and the resulting reaction mixture was stirred at room temperature overnight. EtOAc (500 ml) and water (50 ml) were added, and the pH of the aqueous layer was adjusted to 6 by addition of 1 N HCl solution. The organic layer was washed with brine (50 ml), dried over MgSO$_4$, and concentrated in vacuo to give the title compound in quantitative yield. This was used for the next coupling step without further purification.

2-(5-Cyclohexyl-3-trifluoromethyl-pyrazol-1-yl)-5-methanesulfonyl-pyridine (Step 2)

2-Hydrazino-5-(methylsulfonyl)pyridine hydrochloride (425.2 mg, 1.9 mmol) and TFA (0.44 mL, 5.7 mmol) were mixed in trifluoroethanol (15 mL) and heated at reflux temperature for 15 minutes 4,4,4-trifluoro-1-cyclohexyl-1,3-butanedione (422 mg, 1.9 mmol) in trifluoroethanol (5 ml) was added. The resulting reaction mixture was heated at reflux temperature for 3 hours. The solvent was then removed in vacuo, and the residue was partitioned between EtOAc and water. The organic layer was washed with brine and concentrated in vacuo. The product was purified by flash chromatography using 7:2:0.5 of hexane:diethylamine:methanol to give the title compound (305 mg, 43%).

Example 5

4,4-DIFLUORO-1-CYCLOHEXYL-1,3-BUTANEDIONE (STEP 1)

To a stirred solution of cyclohexylmethylketone (2.52 g, 20 mmol) in DME (50 mL) at −20° C. was added ethyl difluoroacetate (7.44 g, 60 mmol) and sodium methoxide (6.48 g, 120 mmol), and the resulting reaction mixture was then stirred at room temperature for 1 hour. EtOAc (500 ml) and water (50 ml) were added, and the pH of the aqueous layer was adjusted to 6 by addition of 1 N HCl solution. The organic layer was washed with brine (50 ml), dried over Na$_2$SO$_4$, and concentrated in vacuo to give the title (3.8 g, 93%). This was used for the next coupling step without further purification.

2-(5-Cyclohexyl-3-difluoromethyl-pyrazol-1-yl)-5-methanesulfonyl-pyridine (Step 2)

2-Hydrazino-5-(methylsulfonyl)pyridine hydrochloride (448 mg, 2 mmol) and TFA (1.38 mL, 18 mmol) were mixed in trifluoroethanol (10 mL) and stirred for 5 minutes 4,4-Difluoro-1-cyclohexyl-1,3-butanedione (408 mg, 2 mmol) was added. The resulting reaction mixture was heated at reflux temperature for 60 hours. The solvent was then removed in vacuo, and the residue was partitioned between EtOAc and water. The organic layer was washed with brine and concentrated in vacuo. The product was purified by recrystallization from 3:1 of isooctane:methylene chloride to give the title compound (346 mg, 49%).

Example 6

1-(3-CHLORO-4-METHOXYPHENYL) ETHANONE (STEP 1)

To a stirred solution of 1-(3-chloro-4-hydroxylphenyl) ethanone (1.7 g, 10 mmol) in DMF was added K$_2$CO$_3$ (1.52 g, 11 mmol), 2 N NaOH solution (5 ml), and MeI (0.68 ml). The reaction mixture was stirred at room temperature for 2 hours. Another 1.24 ml of MeI was added, and the reaction mixture was stirred for an additional 30 minutes. Water (50 ml) was added, and the product was extracted with 200 ml of EtOAc and 100 ml of benzene. The organic layer was washed with brine (50 ml), and dried with MgSO$_4$, and the solvent was removed in vacuo to give the title compound in quantitative yield.

4,4,4-Trifluoro-1-(3-chloro-4-methoxylphenyl)-1,3-butanedione (Step 2)

To stirred solution of 1-(3-chloro-4-methoxyphenyl) ethanone (2.2 g, 12 mmol) in DME was added ethyl trifluoroacetate (4.28 ml, 36 mmol) and sodium methoxide (4.25 g, 72 mmol), and the resulting reaction mixture was stirred at room temperature for 1 hour. EtOAc (200 ml) and water (50 ml) were added, and the pH of the aqueous layer was adjusted to 6 by addition of 1 N HCl solution. The organic layer was washed with brine (50 ml), dried over MgSO$_4$, and concentrated in vacuo to give the title compound in quantitative yield. This was used for the next coupling step without further purification.

2-[5(3-Chloro-4-methoxy-phenyl)-3-trifluoromethyl-pyrazol-1-yl]5-methanesulfonylpyridine (Step 3)

4,4,4-Trifluoro-1-(3-chloro-4-methoxylphenyl)-1,3-butanedione (1.2 g, 4.29 mmol) and 2-hydrazino-5-(methylsulfonyl)pyridine hydrochloride (1.00 g, 4.46 mmol) were mixed in ethanol (60 ml), and the resulting reaction mixture was heated at reflux temperature overnight. The reaction mixture was then cooled to room temperature, and the solvent was removed in vacuo. The residue was dissolved in EtOAc (250 ml), and the organic layer was washed with saturated NaHCO$_3$ solution, brine, dried (MgSO$_4$), and concentrated in vacuo. The residue was purified by flash chromatography first using 7:3:1 of hexane:diethylamine:methanol and then 20% hexane in methylene chloride to give the title compound (570 mg, 31%).

Example 7

1-(3-METHYL-4-METHOXYPHENYL) ETHANONE (STEP 1)

To a stirred solution of 1-(3-methyl-4-hydroxylphenyl) ethanone (15.02 g, 100 mmol) in MeOH was added K$_2$CO$_3$ (41.5 g, 300 mmol), and MeI (28.4 g, 200 mmol). The reaction mixture was stirred at room temperature for 2 hours. Another 56.7 g of MeI was added, and the reaction mixture was stirred for an additional 2 hours. Water (50 ml) was added, and the product was extracted with 600 ml of EtOAc. The organic layer was washed with brine (250 ml), and dried with Na$_2$SO$_4$, and the solvent was removed in vacuo to give the title compound (10.2 g, 62%).

4,4,4-Trifluoro-1-(3-methyl-4-methoxylphenyl)-1,3-butanedione (Step 2)

To stirred solution of 1-(3-methyl-4-methoxyphenyl) ethanone (3.29 g, 20 mmol) in DME was added ethyl trifluoroacetate (5.68 g, 40 mmol) and sodium methoxide (4.32 g, 80 mmol), and the resulting reaction mixture was stirred at room temperature overnight. EtOAc (200 ml) and water (50 ml) were added, and the pH of the aqueous layer was adjusted to 6 by addition of 1 N HCl solution. The organic layer was washed with brine (50 ml), dried over Na$_2$SO$_4$, and concentrated in vacuo to give the crude product which was recrystallized from isooctane to give the title compound (3.2 g, 62%).

2-[5-(3-Methyl-4-methoxy-phenyl)-3-trifluoromethyl-pyrazol-1-yl]5-methanesulfonylpyridine (Step 3)

4,4,4-Trifluoro-1-(3-methyl-4-methoxylphenyl)-1,3-butanedione (0.78 g, 3 mmol) and 2-hydrazino-5-(methylsulfonyl)pyridine hydrochloride (0.671 g, 3 mmol) were mixed in ethanol (60 ml), and the resulting reaction mixture was heated at reflux temperature for 72 hours. The reaction mixture was then cooled to room temperature, and the solvent was removed in vacuo. The residue was dissolved in EtOAc (250 ml), and the organic layer was washed with saturated NaHCO$_3$ solution, brine, dried (MgSO$_4$), and concentrated in vacuo. The residue was purified first by flash chromatography using 40% hexane in methylene chloride to and then by recrystallization from 3:1 of isooctane:methylene chloride to give the title compound (535 mg, 43%).

Example 8

4,4,4-TRIFLUORO-1-(1-CYCLOHEXENYL)-1,3-BUTANEDIONE (STEP 1)

To a stirred solution of 1-cyclohexenylmethylketone (1 ml, 7.8 mmol) in DME (60 ml) was added ethyl trifluoroacetate (2.8 ml, 23.4 mmol) and sodium methoxide (2.2 g, 39 mmol), and the resulting reaction mixture was stirred at room temperature overnight. EtOAc (200 ml) and water (50 ml) were added, and the pH of the aqueous layer was adjusted to 6 by addition of 2 N HCl solution. The organic layer was washed with brine (50 ml), dried over MgSO$_4$, and concentrated in vacuo to give the title compound in quantitative yield. This was used for the next coupling step without further purification.

2-[5-(1-Cyclohexenyl)-3-trifluoromethyl-pyrazol-1-yl]-5-methanesulfonyl-pyridine (Step 2)

2-Hydrazino-5-(methylsulfonyl)pyridine hydrochloride (128 mg, 0.54 mmol) and 4,4,4-trifluoro-1-(1-cyclohexenyl)-1,3-butanedione (100 mg, 0.45 mmol) were mixed in ethanol (8 ml). The resulting reaction mixture was heated at reflux temperature for 35 hours. The solvent was then removed in vacuo, and the residue was partitioned between EtOAc and water. The organic layer was washed with brine and concentrated in vacuo. The product was purified by flash chromatography using methylene chloride to give the title compound (30.6 mg, 18%).

Example 9

5-METHYLSULFONYL-2-[5-PHENYL-3-TRIFLUOROMETHYL-1H-PYRAZOL-1-YL] PYRIDINE

To a mixture of the 2-hydrazino-5-(methylsulfonyl) pyridine (456 mg, 2.04 mmol) and 4,4,4-trifluoro-1-phenyl-1,3-butanedione (441 mg, 2.04 mmol) in dry trifluoroethanol (30 ml) was added a catalytic amount of concentrated sulfuric acid (~0.5 ml) and the mixture was refluxed overnight. The reaction mixture was cooled to room temperature and diluted with water 50 ml and neutralized with saturated NaHCO$_3$ to PH~7 and then extracted with EtOAc (50 ml×3). The organic layer was washed with brine (25 ml), dried (MgSO$_4$) and concentrated to give the crude solid. The crude solid was recrystallized in ethanol to provide a desired product as a crystalline white solid (337 mg, 45% yield).

The following examples were prepared by an analogous procedure to that of Example 1, except where indicated. LC refers to liquid chromatography elution time (minutes) and MS refers to mass spectral peaks (AMU). The particular apparatus and data acquisition parameters are as defined above.

TABLE 1

| Example | Structure | LC | HRMS |
|---------|-----------|-----|------|
| 10 | 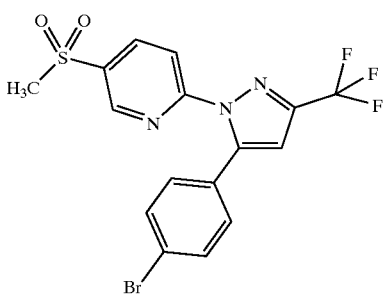 | 10.846 | 446.2, 448.2 |

TABLE 1-continued

| Example | Structure | LC | HRMS |
|---------|-----------|-----|------|
| 11 | 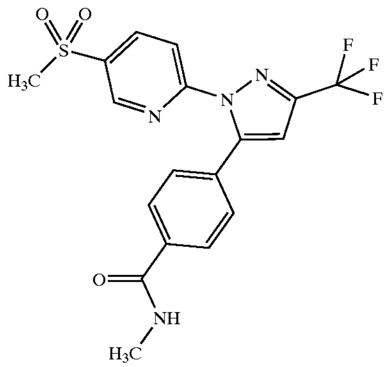 | 4.407 | 425.3 |
| 12 | 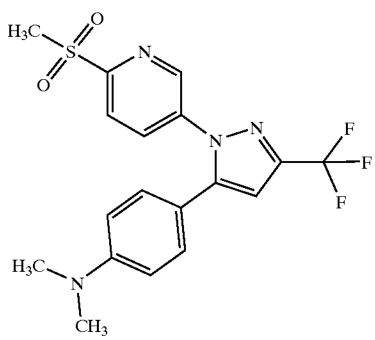 | 9.871 | 411.3 |
| 13 | 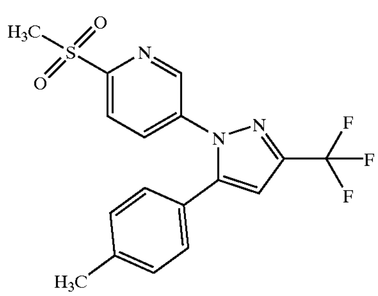 | 9.617 | 382.3 |
| 14 | 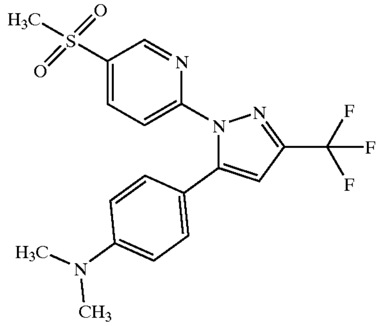 | 9.565 | 411.3 |

TABLE 1-continued

| Example | Structure | LC | HRMS |
|---|---|---|---|
| 15 | 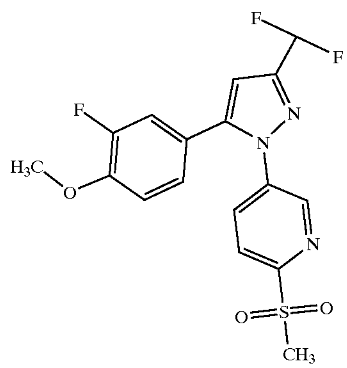 | 6.888 | 398.3 |
| 16 | 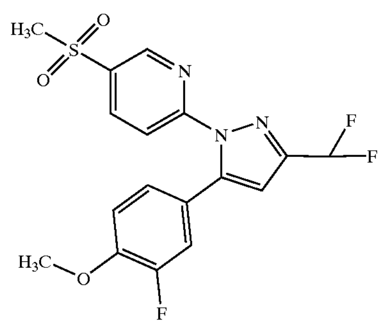 | 7.030 | 398.3 |
| 17 | 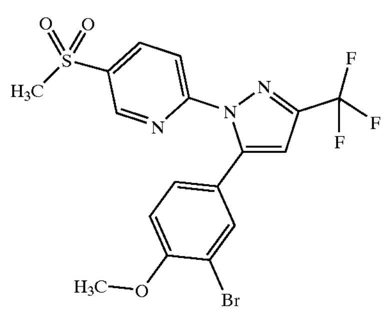 | 10.344 | 476.2, 478.2 |
| 18 | 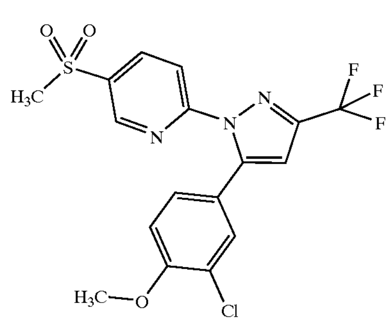 | 9.979 | 432.3 |

TABLE 1-continued

| Example | Structure | LC | HRMS |
|---|---|---|---|
| 19 | 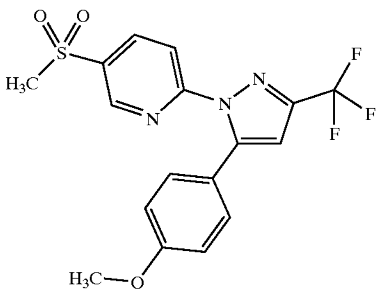 | 8.779 | 398.3 |
| 20 | 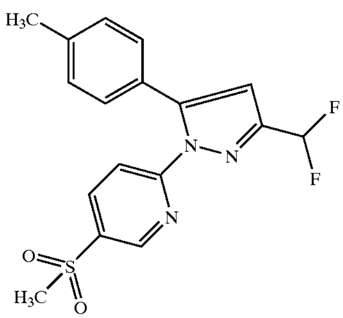 | 8.161 | 364.3 |
| 21 | 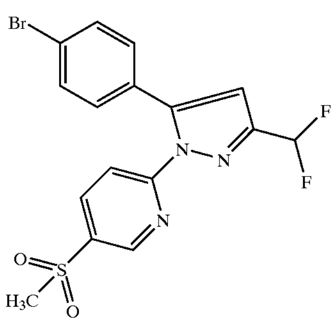 | 9.226 | 428.2, 430.2 |
| 22 | 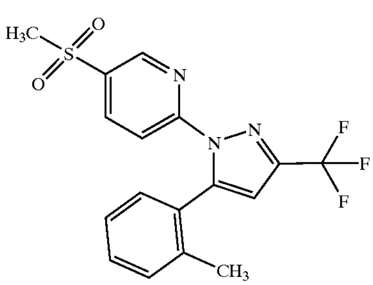 | 10.021 | 382.3 |
| 23 | 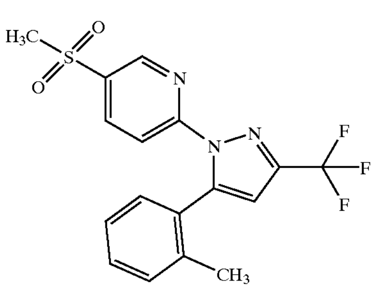 | 8.650 | 368.2 |

TABLE 1-continued

| Example | Structure | LC | HRMS |
|---|---|---|---|
| 24 | 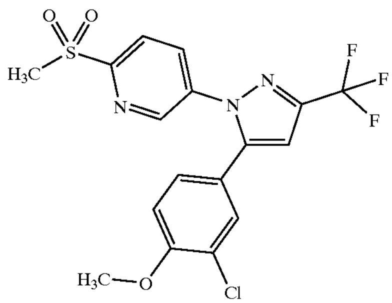 | 9.458 | 432.3 |
| 25 | 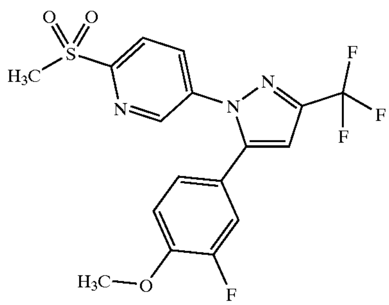 | 8.581 | 416.3 |
| 26 | 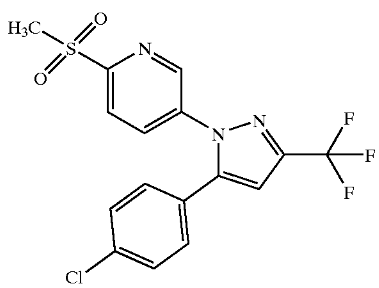 | 9.605 | 402.2, 404.2 |
| 27 | 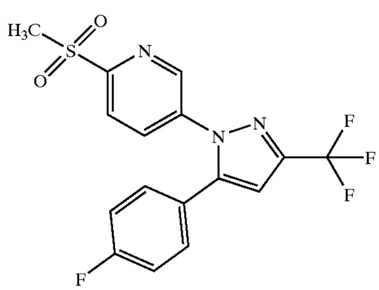 | 8.413 | 386.2 |
| 28 | 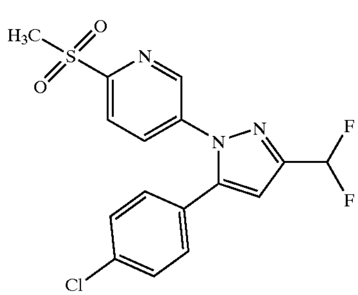 | 8.081 | 384.2, 386.2 |

TABLE 1-continued
| Example | Structure | LC | HRMS |
|---|---|---|---|
| 29 | 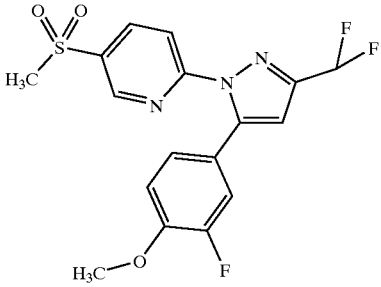 | 8.061 | 414.2, 416.2 |
| 30 | 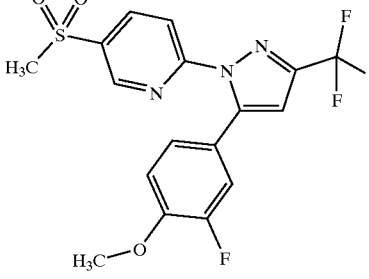 | 8.881 | 416.3 |
| 31 | 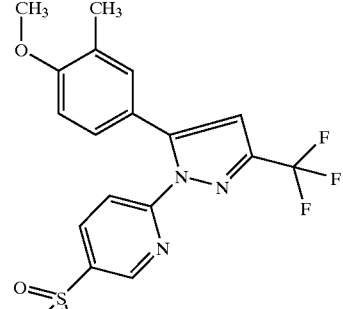 | 10.271 | 412.3 |
| 32 | 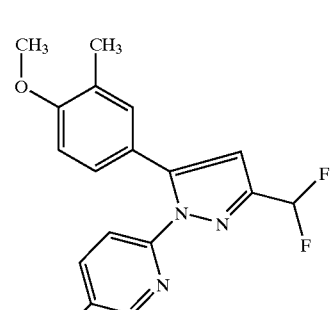 | 8.435 | 394.3 |

TABLE 1-continued

| Example | Structure | LC | HRMS |
|---|---|---|---|
| 33 | 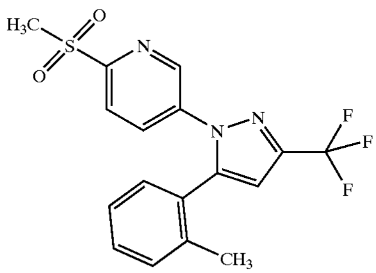 | 9.233 | 382.3 |
| 34 | 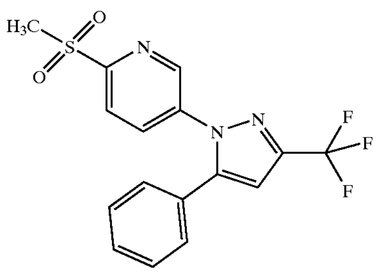 | 8.247 | 368.2 |
| 35 | 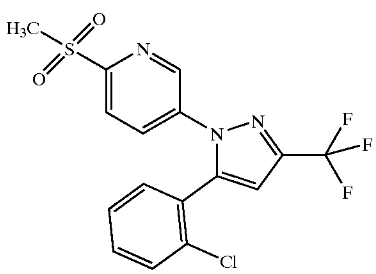 | 9.103 | 402.2, 404.2 |
| 36 | 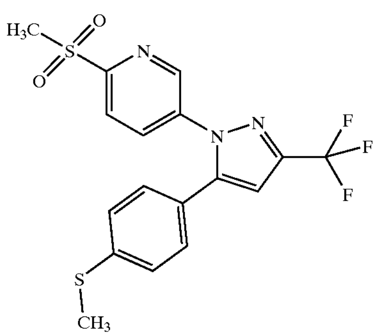 | 9.689 | 414.3 |
| 37 | 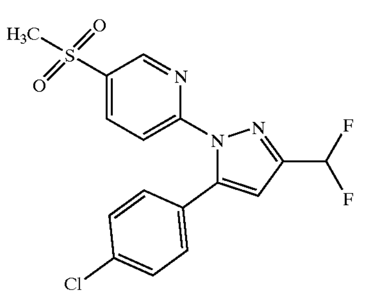 | 8.685 | 384.2 |

TABLE 1-continued

| Example | Structure | LC | HRMS |
|---------|-----------|------|-------|
| 38 | 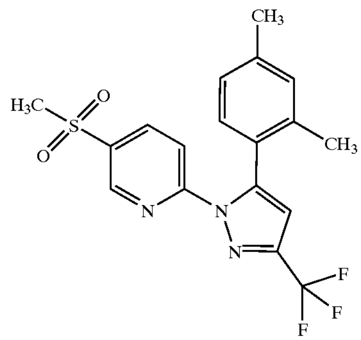 | 11.405 | 396.3 |
| 39 | 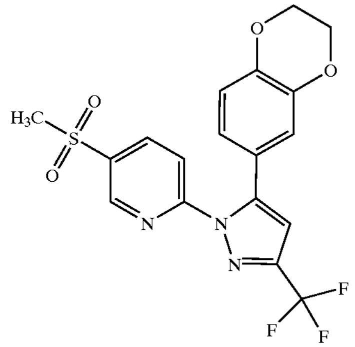 | 8.389 | 426.3 |
| 40 | 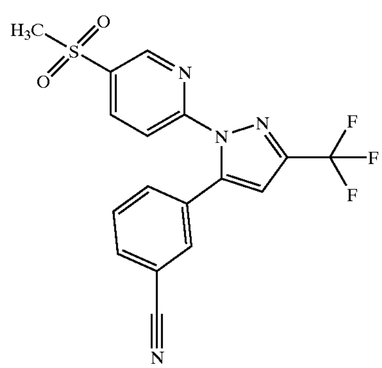 | 8.063 | 393.2 |
| 41 | 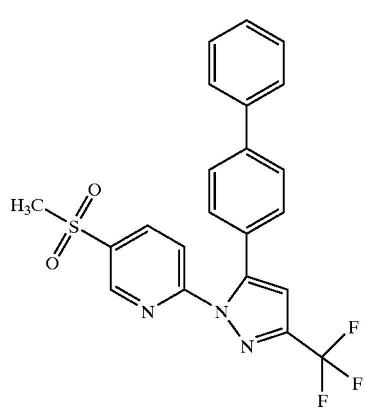 | | |

TABLE 1-continued

| Example | Structure | LC | HRMS |
|---|---|---|---|
| 42 | (3-methyl-4-methoxyphenyl)-pyrazole with CF3 and N-pyridyl-SO2CH3 | 10.234 | 412.3 |
| 43 | (3-methyl-4-methoxyphenyl)-pyrazole with CHF2 and N-pyridyl-SO2CH3 | 8.398 | 394.3 |
| 44 | (benzo[1,3]dioxol-5-yl)-pyrazole with CF3 and N-pyridyl-SO2CH3 | 8.364 | 412.3 |
| 45 | (2-fluoro-4-methoxyphenyl)-pyrazole with CF3 and N-pyridyl-SO2CH3 | 9.556 | 416.3 |

TABLE 1-continued

| Example | Structure | LC | HRMS |
|---|---|---|---|
| 46 | 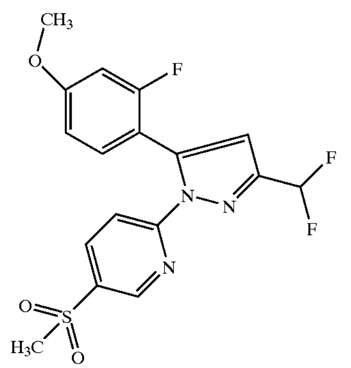 | 7.688 | 398.3 |
| 47 | 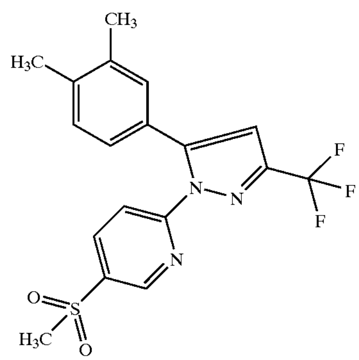 | 10.993 | 396.3 |
| 48 | 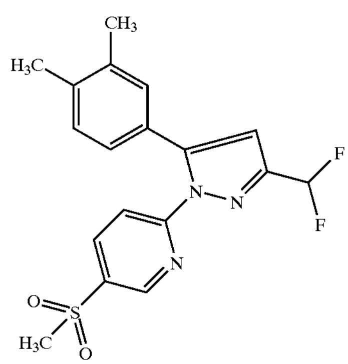 | 9.110 | 378.3 |
| 49 | 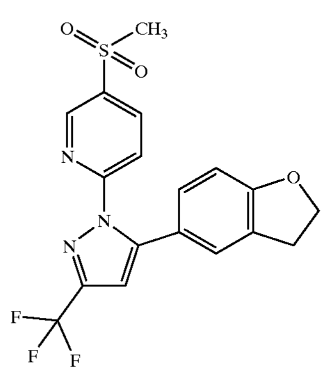 | 8.740 | 410.3 |

TABLE 1-continued

| Example | Structure | LC | HRMS |
|---------|-----------|------|-------|
| 50 | 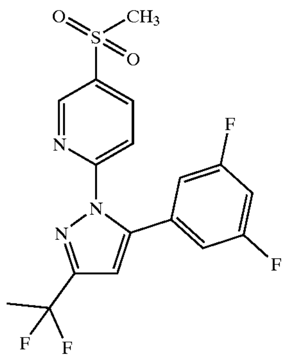 | | |
| 51 | 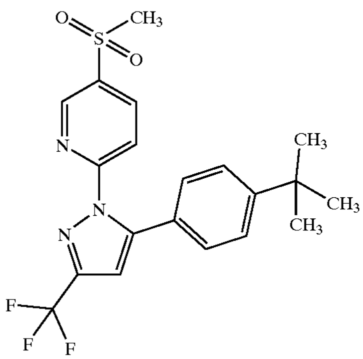 | 12.989 | 424.3 |
| 52 | 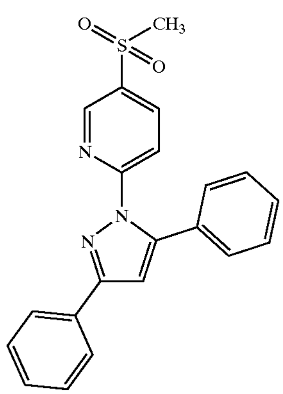 | 10.178 | 376.3 |
| 53 | 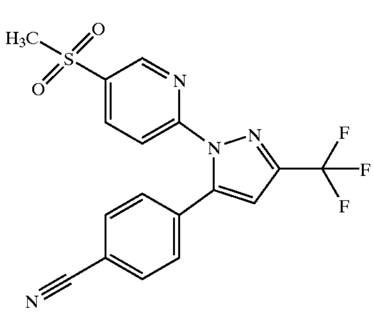 | 8.164 | 393.2 |

TABLE 1-continued
| Example | Structure | LC | HRMS |
|---|---|---|---|
| 54 | 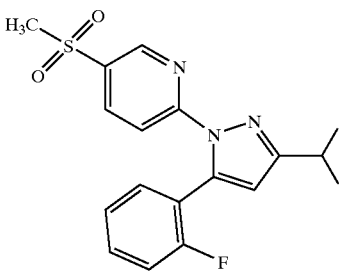 | | |
| 55 | 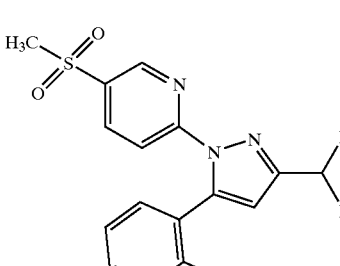 | | |
| 56 | 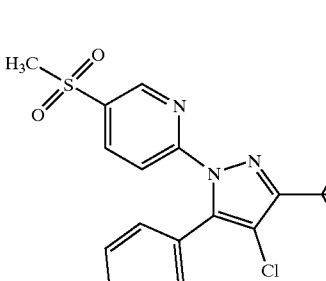 | | |
| 57 | 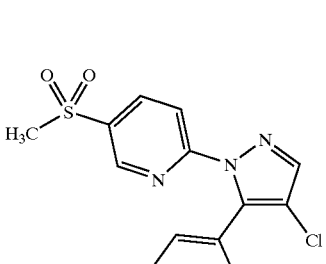 | 7.082 | 334.2 |
| 58 | 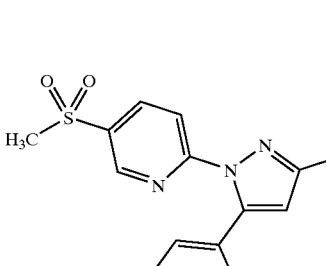 | 2.934 | 344.2 |

TABLE 1-continued

| Example | Structure | LC | HRMS |
|---|---|---|---|
| 59 | 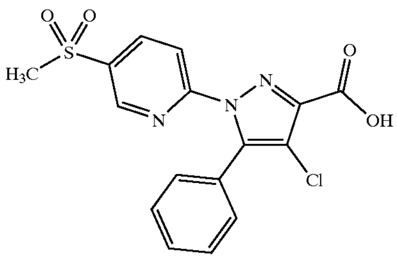 | 3.960 | 378.2 |
| 60 | 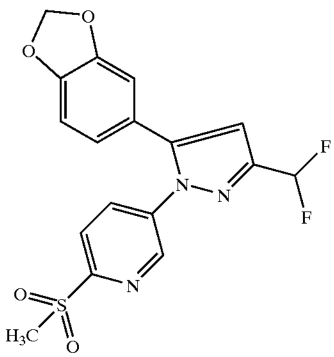 | 6.413 | 394.3 |
| 61 | 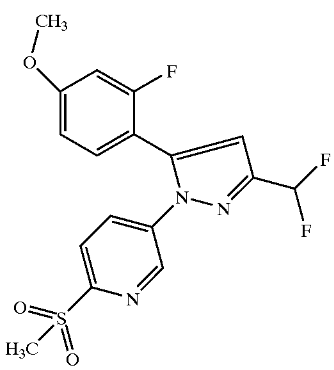 | 7.262 | 398.3 |
| 62 | 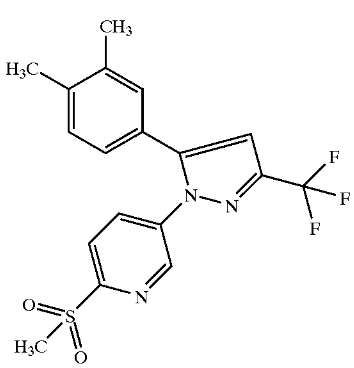 | 10.745 | 396.3 |

TABLE 1-continued

| Example | Structure | LC | HRMS |
|---|---|---|---|
| 63 | 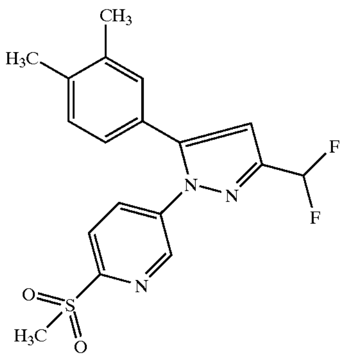 | 8.998 | 378.3 |
| 64 | 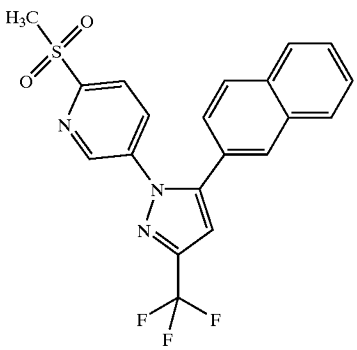 | 10.625 | 418.3 |
| 65 | 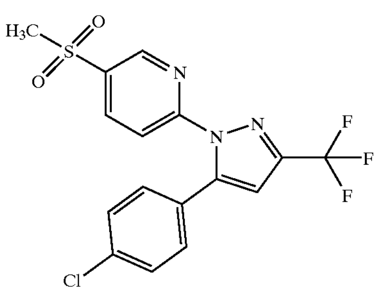 | 10.399 | 402.2, 404.2 |
| 66 | 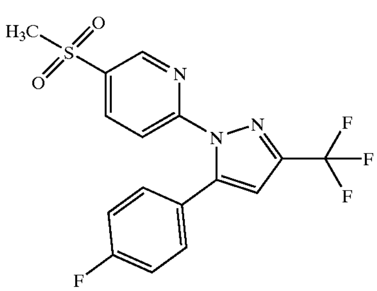 | 9.049 | 386.2 |
| 67 | 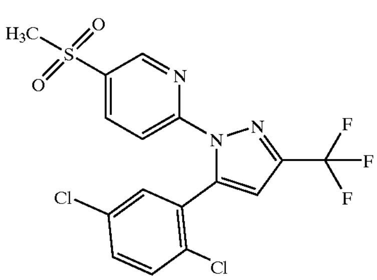 | 11.880 | 436.6, 400.3 |

TABLE 1-continued

| Example | Structure | LC | HRMS |
|---------|-----------|-----|------|
| 68 | 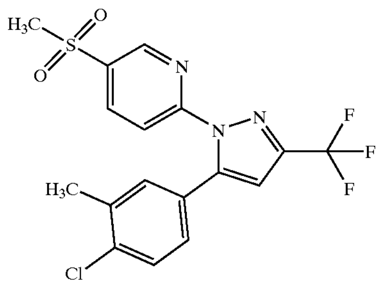 | 11.703 | 416.3 |
| 69 | 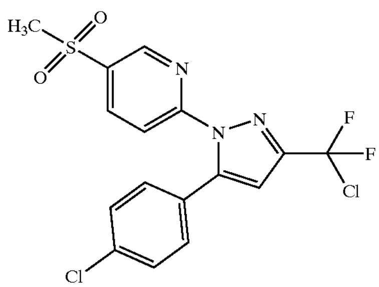 | 11.167 | 418.2, 420.2 |
| 70 | 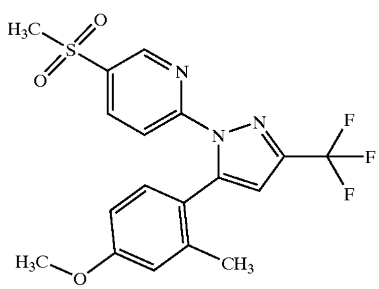 | 9.852 | 412.3 |
| 71 | 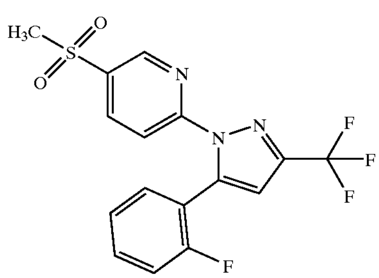 | 9.131 | 386.2, 366.2 |
| 72 | 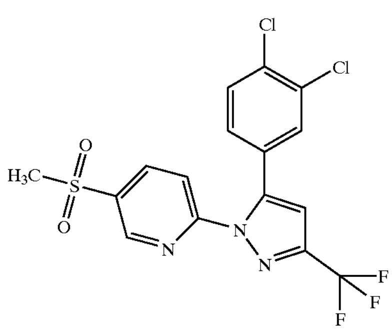 | 11.945 | 436.2, 438.2 |

TABLE 1-continued

| Example | Structure | LC | HRMS |
|---|---|---|---|
| 73 | 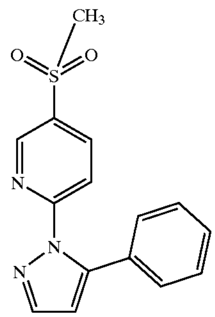 | 4.744 | 300.2 |
| 74 | 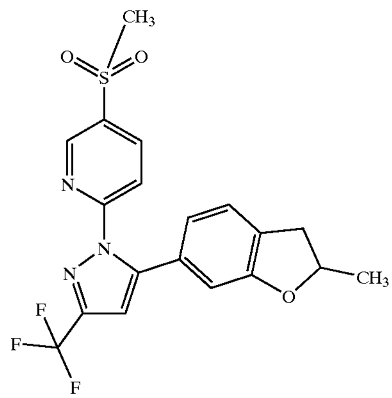 | 9.857 | 424.3 |
| 75 | 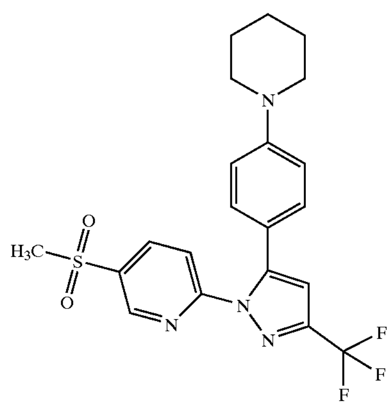 | 10.339 | 451.4 |
| 76 | 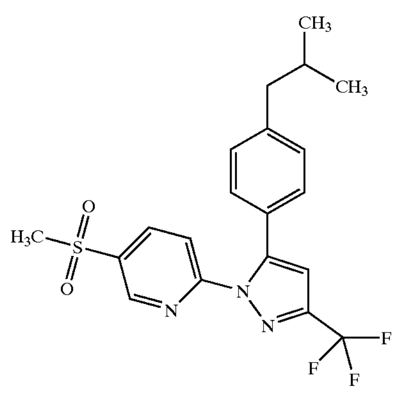 | 13.616 | 424.3 |

TABLE 1-continued
| Example | Structure | LC | HRMS |
|---|---|---|---|
| 77 | 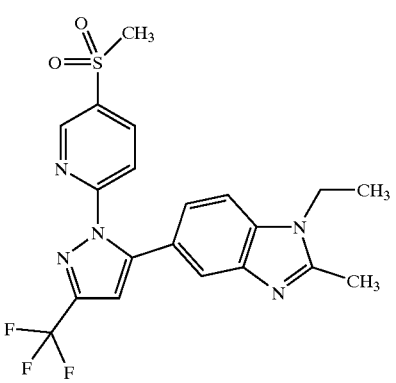 | 1.139 | 450.3 |
| 78 | 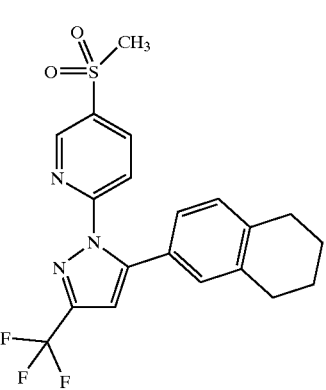 | 12.790 | 422.3 |
| 79 | 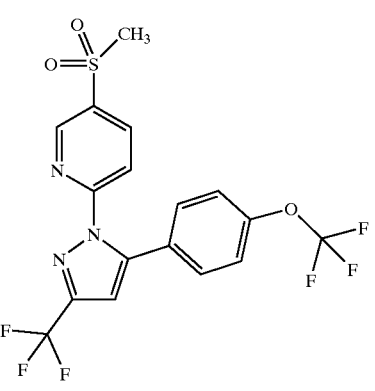 | 11.297 | 452.3 |
| 80 | 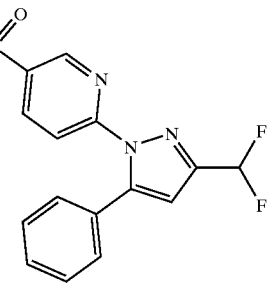 | 6.837 | 350.2 |

TABLE 1-continued

| Example | Structure | LC | HRMS |
|---|---|---|---|
| 81 | 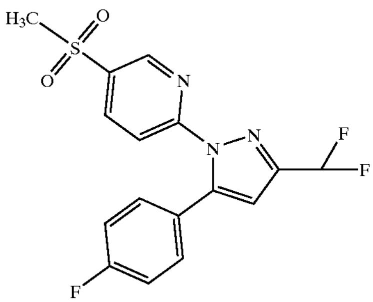 | 7.260 | 368.2 |
| 82 | 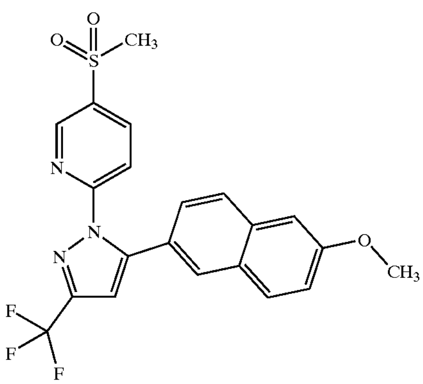 | 11.190 | 448.3 |
| 83 | 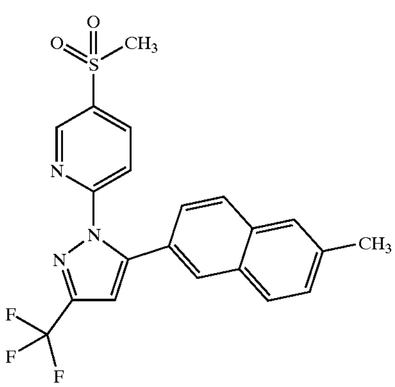 | 12.607 | 432.3 |
| 84 | 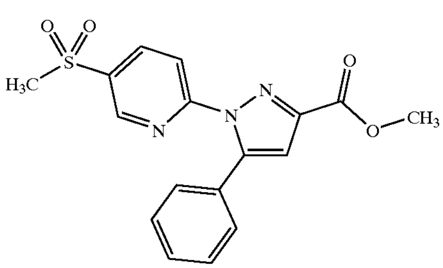 | 5.198 | 358.3 |

TABLE 1-continued

| Example | Structure | LC | HRMS |
|---|---|---|---|
| 85 | 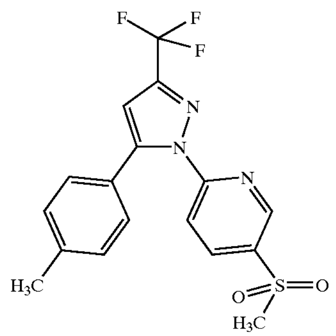 | 10.042 | 382.3 |
| 86 | 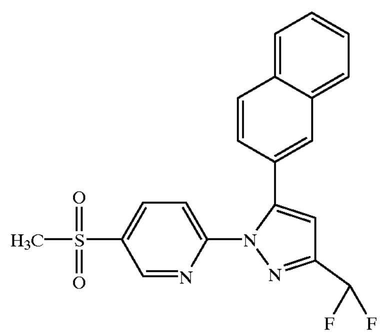 | 9.356 | 400.3 |
| 87 | 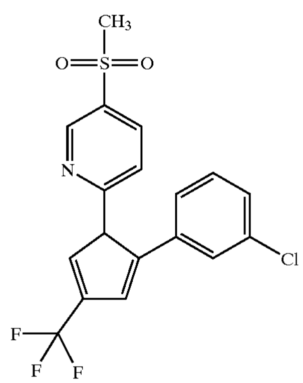 | 10.370 | 402.2, 404.2 |
| 88 | 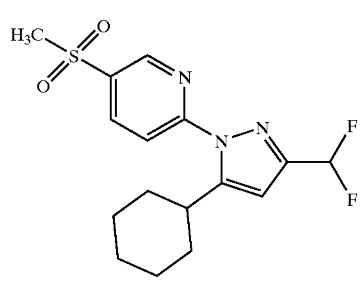 | 11.184 | 356.3 |
| 89 | 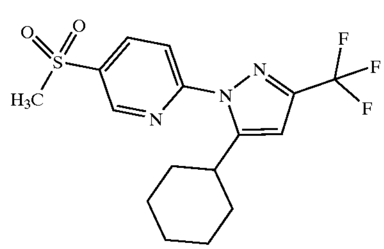 | 13.025 | 374.3 |

TABLE 1-continued

| Example | Structure | LC | HRMS |
|---|---|---|---|
| 90 | 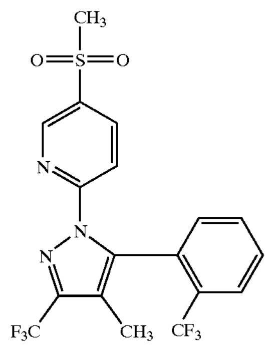 | 11.951 | 450.3 |
| 91 | 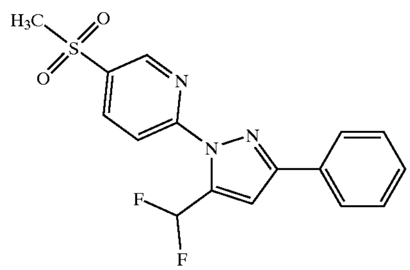 | 9.615 | 350.2 |
| 92 | 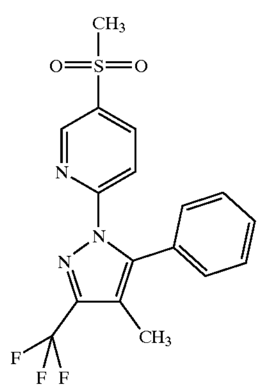 | 10.100 | 382.3 |
| 93 | 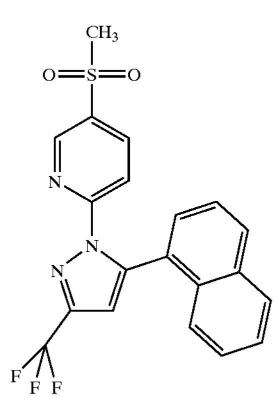 | 11.052 | 418.3 |

TABLE 1-continued

| Example | Structure | LC | HRMS |
|---------|-----------|-----|------|
| 94 | 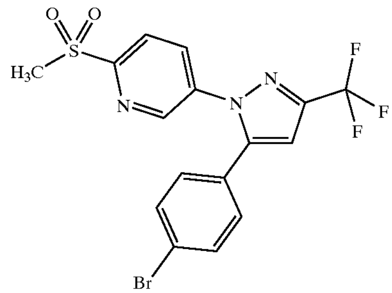 | 9.961 | 446.2, 448.2 |
| 95 | 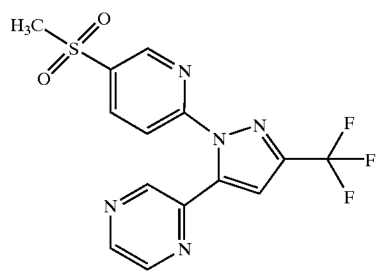 | 5.651 | 370.2 |
| 96 | 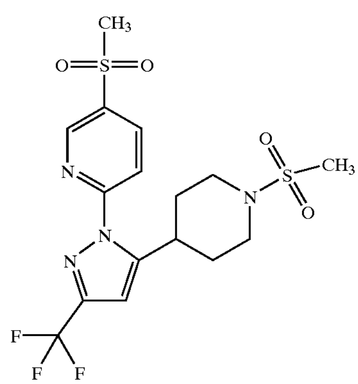 | 6.517 | 453.3 |
| 97 | 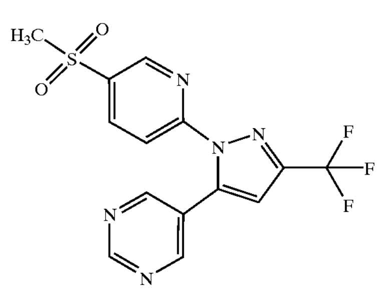 | | |

TABLE 1-continued

| Example | Structure | LC | HRMS |
|---------|-----------|----|----|
| 98 | 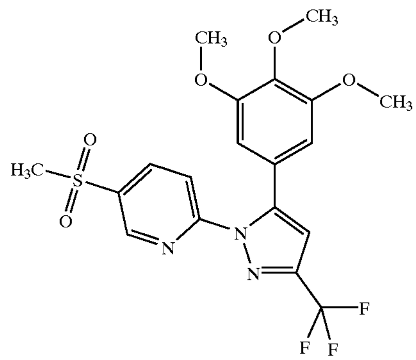 | | |
| 99 | 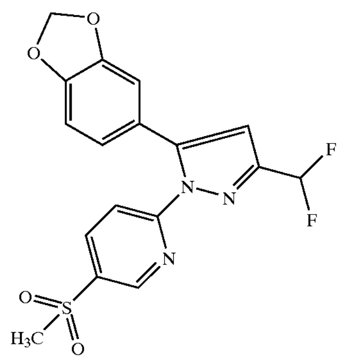 | | |
| 100 | 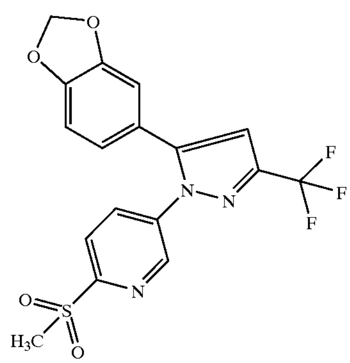 | | |
| 101 | 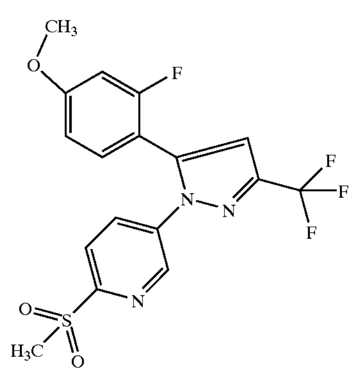 | | |

TABLE 1-continued

| Example | Structure | LC | HRMS |
|---|---|---|---|
| 102 | 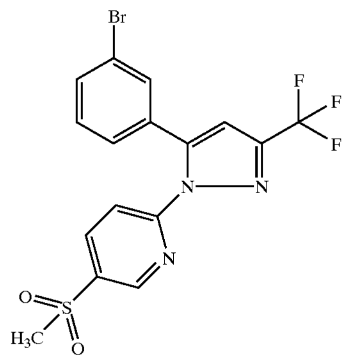 | | |

TABLE 2

| Ex | Structure | MP | MS(M+) | C,H,N | NMR |
|---|---|---|---|---|---|
| 103 | 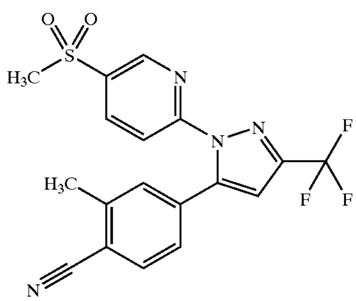 | 191° C. | (EI) 406 | C 53.16%; H 3.42%; N 13.55%. | $^1$H-NMR (270 MHz, CDCl3) δ 8.69 (1 H, d, J=2.5 Hz), 8.39 (1 H, dd, J=2.5 and 8.5 Hz), 8.16 (1 H, d, J=8.6 Hz), 7.61 (1 H, d, J=8.2 Hz), 7.35 (1 H, s), 7.18 (1 H, d, J=7.9 Hz), 6.79 (1 H, s), 3.11 (3 H, s), 2.59 (3 H, s). |
| 104 | 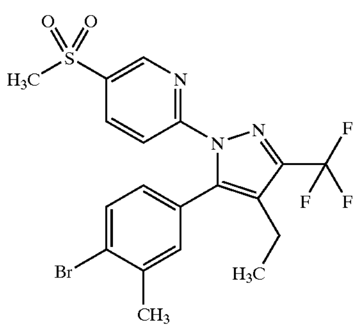 | 149° C. | | C 46.73; H 3.752; N, 8.56. | (CDCl$_3$): 8.66 (dd, J= 0.7, 2.3 Hz, 1H), 8.28 (dd, J =2.5, 8.7 Hz, 1H), 8.00 (dd, J= 0.7, 8.7 Hz, 1H), 7.57 (d,J=8.1 Hz, 1H), 7.14 (d, J=1.8 Hz, 1H), 6.91 (dd, J= 1.8, 8.1 Hz, 1H), 3.08 (s, 3H), 2.49 (q, J=7.4 Hz, 2H), 2.42 (s, 3H), 1.09 (t, J= 7.6 Hz, 3H). |
| 105 | 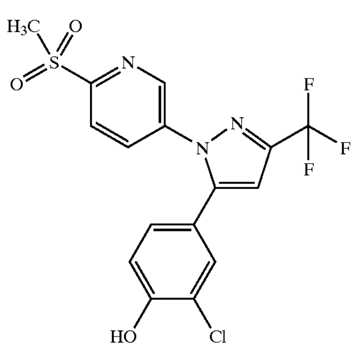 | | | | (DMSO-d$_6$) δ: 8.79 dd, J=1.1, 2.0 Hz, 1H, 8.18-8.12 (m, 2H), 7.49 (d, J=2.2 Hz, 1H), 7.27 (s, 1H), 7.06 (dd, J=2.0, 8.4 Hz, 1H), 6.95 (d, J=8.4 Hz, 1H), 3.24 (s, 3H). |

TABLE 2-continued

| Ex | Structure | MP | MS(M+). | C,H,N | NMR |
|---|---|---|---|---|---|
| 106 | 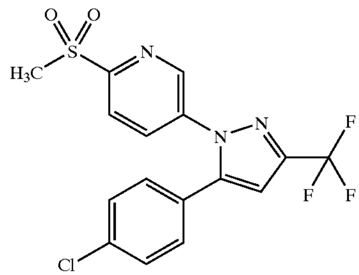 | 138° C. | (EI) 401 | C 47.76%; H 2.97%; N 10.39%. | (300 MHz, CDCl3) δ 8.69 (1 H, dd, J=0.7 and 2.6 Hz), 8.12 (1 H, dd, J=0.6 and 8.4 Hz), 7.94 (1 H, dd, J=2.6 and 8.4 Hz), 7.46-7.40 (2 H, m), 7.24-7.18 (2 H, m), 6.83 (1 H, s), 3.25 (3 H, s). |

Example 107

5-METHANESULFONYL-2-(5-NAPHTHALEN-2-YL-3-TRIFLUOROMETHYL-PYRAZOL-1-YL)-PYRIDINE

5-Hydrazino-2-(methylsulfonyl)pyridine hydrochloride (63 mg, 0.34 mmol) was added to a solution of 1-(2-napthoyl)-3,3,3-trifluoroacetone (98 mg, 0.37 mmol) in trifluoroethanol (3.5 mL) with two drops of conc sulfuric acid. The mixture was heated at reflux temperature (85–90° C. bath temperature) for 18 hours and cooled down to room temperature. The reaction mixture was poured into a saturated aqueous sodium bicarbonate (20 ml) and extracted with ethyl acetate (20 ml×2), dried (MgSO₄), filtered and concentrated in vacuo. The resulting crude mixture was subjected to preparative thin layer chromatographic (TLC) (1000 um plate) purification with dichloromethane as eluant. The desired product was isolated after the band containing the product was washed with ethyl acetate and concentrated in vacuo to provide 28 mg of a pale white solid.

Liquid chromatography yielded product eluting at 11.277 minutes with major mass spectral fragment peaks at 418.3 AMU.

Example 108

2-METHYLSULFONYL-5-[5-PHENYL-3-TRIFLUOROMETHYL-1H-PYRAZOL-1-YL]PYRIMIDINE

5-Fluoro-4-thiouracil can be prepared from 5-fluorouracil as described (*J. Med. Chem.*, Vol. 6, pp. 697–701 (1963)). 5-Fluoro-2(1H)-pyrimidinone can be subsequently prepared as described (*Acta Chem. Scand.*, Vol. 23, pp. 294–299 (1969)). 5-Fluoro-2(1H)-pyrimidinone can then be converted to 2-methanesulfonyl-5-fluoropyrimidine by treatment with phosphorus oxychloride, followed by reaction with sodium methanethiolate and oxidation with m-chloroperbenzoic acid as described (*Acta Chem. Scand.*, Vol. B39, pp. 696–696 (1985)). Conversion to the hydrazine is then effected by treatment of 2-methylsulfonyl-5-fluoropyrimidine with hydrazine hydrate in ethanol (*Coll. Czech. Chem. Commun.*, Vol. 37, pp. 1721–17330 (1972)). Subsequent reaction of 2-methylsulfonyl-5-hydrazinopyrimidine with 4,4,4-trifluoro-1-phenyl-1,3-butanedione will then produce the title compound.

Example 109

5-METHYLSULFONYL-2-[5-(4-METHOXY)PHENYL-3-TRIFLUOROMETHYL-1H-PYRAZOL-1-YL]PYRAZINE

2-Amino-5-bromopyrazine can be prepared from aminopyrazine as described (*Tetrahedron*, Vol. 44, pp. 2977–2984 (1988)). Reaction of 2-amino-5-bromopyrazine with sodium methanethiolate proceeds to form 2-amino-5-methylthiopyrazine (*J. Het. Chem.*, Vol. 28, pp. 1131–1137 (1991)). Oxidation of 2-amino-5-methylthiopyrazine with m-chloroperbenzoic acid produces 2-amino-5-methanesulfonylpyrazine. 2-Hydrazino-5-methanesulfonylpyrazine can be prepared by known procedures (*J. Het. Chem.*, Vol. 27, pp. 2151–2163 (1990)). Subsequent reaction of 2-Hydrazino-5-methanesulfonylpyrazine with 4,4,4-trifluoro-1-(4-methoxyphenyl)-1,3-butanedione (made from 4-methoxyacetophenone and ethyl trifluoroacetate via Scheme 1) can then produce the title compound.

Example 110

1-METHYLSULFONYL-3-[5-(4-FLUORO)PHENYL-3-TRIFLUOROMETHYL-1H-PYRAZOL-1-YL]PYRROLE

1-Methylsulfonyl-3-nitropyrrole can be prepared from pyrrole as described (*Can. J. Chem.*, Vol 63, pp. 896–902 (1985)). 1-Methylsulfonyl-3-aminopyrrole can then be prepared from 1-Methanesulfonyl-3-nitropyrrole and further reacted to 1-methylsulfonyl-3-hydrazinopyrrole by known procedures (*J. Het. Chem.*, Vol. 27, pp. 2151–2163 (1990)). Subsequent reaction of 1-methylsulfonyl-3-hydrazinopyrrole with 4,4,4-trifluoro-1-(4-fluoro)phenyl-1,3-butanedione (made from 4'-fluoroacetophenone and ethyl trifluoroacetate via Scheme I) can then produce the title compound.

Example 111

1-METHYL-2-METHYLSULFONYL-4-[5-(4-CHLORO)PHENYL-3-TRIFLUOROMETHYL-1H-PYRAZOL-1-YL]PYRROLE

1-Methyl-2-methylsulfonyl-4-nitropyrrole can be prepared from pyrrole by modification of a known procedure (*J. Chem. Res. Miniprint*, Vol. 3, pp. 0725–0754 (1983)). 1-Methyl-2-methylsulfonyl-4-aminopyrrole can then be prepared from 1-methyl-2-methylsulfonyl-4-nitropyrrole and further reacted to 1-methyl-2-methylsulfonyl-4-hydrazinopyrrole by known procedures (*J. Het. Chem.*, Vol. 27, pp. 2151–2163 (1990)). Subsequent reaction of 1-methyl-2-methylsulfonyl-4-hydrazinopyrrole with 4,4,4-trifluoro-1-(4-chloro)phenyl-1,3-butanedione (made from 4'-chloroacetophenone and ethyl trifluoroacetate via Scheme I) can then produce the title compound.

Example 112

1-METHYL-3-METHYLSULFONYL-5-[5-(4-METHYL)PHENYL-3-TRIFLUOROMETHYL-1H-PYRAZOL-1-YL]PYRROLE

1-Methyl-3-methylsulfonyl-5-nitropyrrole can be prepared from pyrrole by modification of a known procedure (*J.

Chem. Res. Miniprint, Vol. 3, pp. 0725–0754 (1983)). 1-Methyl-3-methylsulfonyl-5-aminopyrrole can then be prepared from 1-methyl-3-methylsulfonyl-5-nitropyrrole and further reacted to 1-methyl-3-methylsulfonyl-5-hydrazinopyrrole by known procedures (J. Het. Chem., Vol. 27, pp. 2151–2163 (1990)). Subsequent reaction with 4,4,4-trifluoro-1-(4-methyl)phenyl-1,3-butanedione (made from 4'-methylacetophenone and ethyl trifluoroacetate via Scheme I) can then produce the title compound.

Example 113

2-METHYLSULFONYL-5-[5-(3-METHYL) PHENYL-3-TRIFLUOROMETHYL-1H-PYRAZOL-1-YL]PYRROLE

2-Methylthiopyrrole can be prepared from pyrrole as described (J. Org. Chem., Vol. 47, pp. 1682–1688 (1982)). 5-Chloro-2-methylthiopyrrole can then be prepared from 2-methylthiopyrrole by known procedures (J. Het Chem., Vol. 22, pp. 281–285 (1985)). 5-Hydrazino-2-methylthiopyrrole can then be prepared as in Scheme 2. Subsequent reaction of 5-Hydrazino-2-methylthiopyrrole with 4,4,4-trifluoro-1-(3-methyl)phenyl-1,3-butanedione (made from 3'-methylacetophenone and ethyl trifluoroacetate via Scheme I) followed by oxidation can produce the title compound.

Example 114
Tablet formulation of the product of Example 6.

| Tablet Formulation | |
| --- | --- |
| Ingredients | Weight per Tablet |
| Example 6 | 25.00 mg |
| Lactose, U.S.P. | 64.50 mg |
| Corn Starch | 10.00 mg |
| Magnesium Stearate | 0.50 mg |

Example 115
Capsule formulation of Example 15

| Capsule Formulation | |
| --- | --- |
| Ingredients | Weight per Capsule |
| Example 15 | 50 mg |
| Lactose, U.S.P. | 124 mg |
| Corn Starch, U.S.P. | 30 mg |
| Talc, U.S.P. | 5 mg |
| Total Weight: | 210 mg |

Example 116
Parenteral Formulation of 30

| Parenteral Formulation | |
| --- | --- |
| Ingredients per 1 cc ampule | Weight per Ampule |
| Example 30 | 10.2 mg |
| Methyl Paraben, U.S.P. | 1.8 mg |
| Propyl Paraben, U.S.P. | 0.2 mg |

| Parenteral Formulation | |
| --- | --- |
| Ingredients per 1 cc ampule | Weight per Ampule |
| Sodium Hydroxide, U.S.P. q.s. ph | 9.0 mg |
| Water for Injection, U.S.P. q.s. ad | 1.0 cc |

PREPARATIONS

Preparation 1

Step 1: 3-NITRO-6-(METHYLTHIO)PYRIDINE

2-Mercapto-5-nitro pyridine (20.0 g, 128 mmol) was suspended in water/ethanol (43 mL/13 mL). Sodium carbonate monohydrate (17.49 g, 141 mmol, dissolved in 86 mL of water) was added to the above slurry dropwise. Methyl iodide (20.0 g, 141 mmol) was added to the above mixture and the mixture was stirred at room temperature for one hour. The solid was filtered and washed with water and ethanol to provide the title compound in quantitative yield.

Step 2A: 3-NITRO-6-(METHYLSULFONYL) PYRIDINE

3-Nitro-6-(methylthio)pyridine (22.0 g, 129.3 mmol) was dissolved in acetone (140 mL). Sulfuric acid (2N, 230 mL) was then added dropwise to above solution to form a slurry. Potassium permanganate ($KMnO_4$) (26.5 g, 168.1 mmol, dissolved in 500 mL of $H_2O$) was added to the above mixture dropwise. The mixture that resulted was stirred at room temperature overnight. The solid was filtered and stirred with a warm mixture of ethanol/methanol (10/1). The insoluble salt was filtered, the filtrate was concentrated to provide a pale yellow solid. The crude product was recrystallized from ethanol to furnish the title compound (17.8 g, 70%).

Step 2B: 3-NITRO-6-(METHYLSULFONYL) PYRIDINE

Alternatively, 3-nitro-6-(methylsulfonyl)pyridine was prepared by dissolving of 3-nitro-6-(methylthio)pyridine (1 equivalent) and sodium methane sulfinate in DMSO and heating at 100° C. for 2 hours. The reaction was diluted with a large excess of water and extracted with ethyl acetate. The organic layer was concentrated in vacuo to give the desired 3-nitro-6-(methylsulfonyl)pyridine.

Step 3: 3-AMINO-6-(METHYLSULFONYL) PYRIDINE

3-Nitro-6-(methylsulfonyl)pyridine (10 g, 49.5 mmol) was suspended in water (200 mL). Iron powder (5.0 g, 89.3 mmol) and acetic acid (0.5 mL) were added to the above mixture. The mixture, which resulted, was heated to reflux for 2 hours. The reaction was monitored by thin layer chromatography (ethyl acetate/hexane, 1/1). The reaction mixture was then cooled to room temperature and a saturated solution of sodium bicarbonate ($NaHCO_3$) (100 mL) was added to the mixture. Ethyl acetate (200 mL) was added to the above mixture and the mixture which resulted was stirred at room temperature for 30 minutes. The mixture was filtered through Celite® and the organic layer was collected. The aqueous layer was extracted with ethyl acetate (200 mL×3). The organic extractions were combined and dried over sodium sulfate. The solvent was removed under reduced pressure to provide the 3-amino-6-(methylsulfonyl) pyridine (6g, 70.5%).

Step 4: 5-HYDRAZINO-2-(METHYLSULFONYL) PYRIDINE HYDROCHLORIDE

To a solution of 3-amino-6-(methylsulfonyl)pyridine (3.72 g, 21.6 mmol) in concentrated hydrochloric acid (30 mL), sodium nitrite (1.78 g, 25.7 mmol) in water (20 mL) was added dropwise at −10 to −15° C. and the mixture was stirred for 2 hours at −10 to −5° C. (note: the reaction was monitored by thin layer chromatography to make sure all the starting material was consumed). Tin(II) chloride dihydrate (20 g, 88.6 mmol) in concentrated hydrochloric acid (30 mL) was added dropwise at −5° C. The mixture was stirred 1 hour at −5° C. and then left overnight. The mixture was basified with aqueous sodium hydroxide (pH=9) with ice cooling and tetrahydrofuran (200 mL) was added and stirred for 30 minutes. The mixture was filtered through Celite® and the filtrate was extracted with tetrahydrofuran (200 mL×3). The organic extraction was combined and dried over magnesium sulfate and concentrated under reduced pressure to provide the title compound (3.2g, 78.8%).

5-Hydrazino-2-(methylsulfonyl)pyridine was dissolved in HCl-methanol (10%, 30 mL) and volatiles were removed under reduced pressure. The residue was washed with ether and employed directly to next step without further purification.

Preparation 2
2-HYDRAZINO-5-(METHYLSULFONYL)PYRIDINE HYDROCHLORIDE

STEP 1: 5-Methylthio-2-bromopyridine

To a solution of 2,5-dibromopyridine (23.4 g, 0.099 mol) in ether (500 mL), was added dropwise n-butyl lithium (n-BuLi) (1.52 M in n-hexane, 68 mL, 0.10 mmol) at −78° C. and the mixture was stirred for 1 hour at the temperature. Dimethyldisulfide (9.8 mL, 0.11 mol) was added slowly at −78° C. and the mixture was stirred for 1 hour at that temperature and further 1 hour at 0° C. The mixture was quenched with aqueous 1N hydrochloric acid (200 mL) and extracted with ether (100 mL×2), dried over MgSO$_4$, and concentrated in vacuo to yield the title compound (18.9 g, 94%).

$^1$H-NMR (CDCl$_3$) δ: 8.24 (dd, J=0.8, 2.5 Hz, 1H), 7.43 (dd, J=2.8, 8.4 Hz, 1H), 7.38 (dd, J=0.8, 8.4 Hz, 1H), 2.50 (s, 3H).

STEP 2: 5-Methylsulfonyl-2-bromopyridine

To a solution of 5-methylthio-2-bromopyridine from step 1 (18.9 g, 0.093 mol) in methylene chloride (600 mL), was added portionwise m-chloroperbenzoic acid (48 g, 0.19 mol) at 0° C. and the mixture was stirred for 2 hours at room temperature. Aqueous saturated sodium sulfate (Na$_2$SO$_3$) (200 mL) was added and stirred for 15 minutes and organic phase was separated and washed with aqueous saturated sodium bicarbonate (NaHCO$_3$) (200 mL), dried over MgSO$_4$, and concentrated in vacuo gave the title compound (20.9g, 96%).

$^1$H-NMR (CDCl$_3$) δ: 8.91 (d, J=2.6 Hz, 1H), 8.06 (dd, J=2.6, 8.4 Hz, 1H), 7.73 (d, J=8.4 Hz, 1H), 3.12 (s, 3H).

Step 3: 2-Hydrazino-5-(methylsulfonyl)pyridine hydrochloride

A mixture of 5-methylsulfonyl-2-bromopyridine from step 2 (20.9 g, 0.088 mol) and anhydrous hydrazine (5.6 mL, 0.18 mol) in ethanol (200 mL) was refluxed for 4 hours. After cooling to room temperature the mixture was concentrated. The residual solid was washed with aqueous saturated NaHCO$_3$ (100 mL) and water (100 mL) and collected by filtration to give a pale yellow solid (9.6 g). The solid was treated with 10% methanolic HCl (80 mL) and the precipitate was collected by filtration to give the title compound (9.8 g, 50%).

$^1$H-NMR (DMSO-d$_6$) δ: 8.54 (s, 1H), 7.99 (d, J=8.9 Hz, 1H), 6.94 (d, J=8.9 Hz, 1H), 3.20 (s, 3H). (hydrazine proton was not detected).

Alternative Preparation 2
2-HYDRAZINO-5-(METHANESULFONYL) PYRIDINE HYDROCHLORIDE

STEP 1: 2,5-BIS-METHYLSULFANYL-PYRIDINE

A solution of the 2,5-dichloropyridine and sodium methane thiolate in DMSO was heated at 100–120° C. for 3 days. The reaction mixture was cooled down and diluted with water and then extracted with ether. The organic layer was concentrated in vacuo to give the title compound (52%).

STEP 2: 2,5-BIS-METHANESULFONYL-PYRIDINE

The 2,5-bis-methylsulfanyl-pyridine in dry methylene chloride at 0° C. was treated with mCPBA (~4 equiv.) and allowed to react overnight, while warming to room temperature. The reaction mixture was washed with saturated bicarbonate and extracted with ethyl acetate or ether. The organic layer was dried and concentrated in vacuo to give the title compound in quantitative yield.

STEP 3: 2-HYDRAZINO-5-(METHANESULFONYL) PYRIDINE HYDROCHLORIDE

The 2,5-bis-methanesulfonyl-pyridine and anhydrous hydrazine are stirred in ethanol for two hours between room temperature and reflux temperature. After cooling to room temperature the mixture is concentrated. The residual solid is washed with aqueous saturated NaHCO$_3$ and water and collected by filtration to give a pale yellow solid. The solid is treated with 10% methanolic HCl and the precipitate is collected by filtration to give the title compound.

Preparation 3
2-METHYLSULFONYL-5-HYDRAZINOPYRIMIDINE HYDROCHLORIDE

2-Methylsulfonyl-5-hydrazinopyrimidine (2.0 g, 0.011 mol, J. Vavrina et al., Collection Czechoslov. Chem. Commun., 37, 1721 (1972)) was treated with 10% methanolic HCl, and volatiles were removed by evaporation. The precipitate was collected by filtration to give 1.8 g (78%) of the title compound.

$^1$H-NMR (DMSO-d$_6$) δ: 9.43 (br, 1H), 8.50 (s, 2H), 3.48 (br, 2H), 3.22 (s, 3H).

Preparation of Diketones
Preparation 4
4,4,4-TRIFLUORO-1-[4-(BENZODIHYDROFUR-4-YL)BUTANE-1,3-DIONE A solution mixture of the 1-(2,3-dihydrobenzofuran-5-yl) ethan-1-one (212 mg, 1.31 mmol) and ethyltrifluoroacetate (428 mg, 3.0 mmol) in dry dimethoxyethane (4 ml) at room temperature was treated with sodium methoxide (0.69 ml, 3.0 mmol) and the reaction mixture vigorously stirred at room temperature for 18 hours. The reaction mixture was poured into aqueous 1N hydrochloric acid (20 ml) and extracted with ethyl acetate (20 ml×2), dried (MgSO4), filtered, and concentrated in vacuo to give the desired diketone.

Preparation 5
4,4,4-TRIFLUORO-1-(2,4-DICHLOROPHENYL)-1,3-BUTANEDIONE

To a mixture of 1-(2,4-dichlorophenyl)ethanone (19.3g, 0.102 mol) and 1,1,1-trifluoroacetic acid ethyl ester (21.8 g, 0.1531 mol) in anhydrous ethylene glycol dimethyl ether (200 mL) was added sodium methoxide (44.12 g, 25 wt. % sodium methoxide in methanol, 0.204 mol) and the mixture was stirred at room temperature overnight. The reaction mixture was poured into a flask containing 200 mL of ethyl acetate (EtOAc) and ice, pH was adjusted to 4–5 using 3N hydrochloric acid and then layers were separated. The aqueous layer was extracted with EtOAc (200 mL). The organic layers were combined, dried (MgSO$_4$) and concentrated to give the crude solid. The crude solid was recrystallized from isooctane to provide the desired product as a pale yellow solid (15.2 g, 52% yield).

Preparation 6

4,4-DIFLUORO-1-(4-FLUOROPHENYL)-1,3-BUTANEDIONE

To a mixture of 1-(4-fluorophenyl) ethanone (5 g, 0.036 mol) and 1,1-difluoroacetic acid ethyl ester (4.94 g, 0.040 mol) in anhydrous ethylene glycol dimthyl ether (100 mL) was added sodium methoxide (15.6 g, 25 wt. % sodium methoxide in methanol, 0.072 mol) and the mixture was stirred at room temperature overnight. The reaction mixture was poured into a flask containing 200 mL of EtOAc and ice, pH was adjusted to 4–5 using 3N HCl and then layers were separated. The aqueous layer was extracted with EtOAc (200 mL). The organic layers were combined, dried (MgSO$_4$) and concentrated to give the crude solid. The crude solid was directly used in next step without further purification.

What is claimed is:

1. A compound of the formula

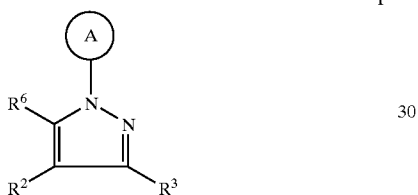

I wherein A is a heterocycle selected from the group consisting of

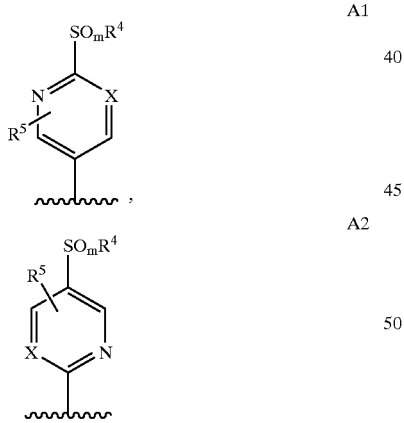

A1

A2 m is 0, 1 or 2;

X is $CR^8$;

$R^2$ is hydrogen, halo, ($C_1$–$C_6$)alkyl, ($C_2$–$C_6$)alkenyl, ($C_2$–$C_6$)alkynyl, ($C_1$–$C_6$)alkoxy, ($C_1$–$C_6$)alkyl-(C=O)—, formyl, formamidyl, cyano, nitro, HO—(C=O)—, ($C_1$–$C_6$)alkoxycarbonyl, aminocarbonyl, N—($C_1$–$C_6$)alkylaminocarbonyl, N,N-[($C_1$–$C_6$)alkyl]$_2$aminocarbonyl, N—($C_6$–$C_{10}$)arylaminocarbonyl, N,N-[($C_6$–$C_{10}$)aryl]$_2$aminocarbonyl, N—($C_1$–$C_6$)alkyl-N—($C_6$–$C_{10}$)arylaminocarbonyl, ($C_6$–$C_{10}$)aryl, ($C_6$–$C_{10}$)aryloxy, ($C_1$–$C_6$)alkoxyaminocarbonyl or ($C_1$–$C_6$)alkyl-carbonylamino;

wherein said $R^2$ ($C_1$–$C_6$)alkyl group may optionally be substituted with one to three substituents independently selected from halo, hydroxy, ($C_1$–$C_6$)alkoxy, cyano, nitro, HO—(C=O)—, ($C_1$–$C_6$)alkoxycarbonyl, aminocarbonyl, N—($C_1$–$C_6$)alkylaminocarbonyl, N,N—[($C_1$–$C_6$)alkyl]$_2$aminocarbonyl, N—($C_6$–$C_{10}$)arylaminocarbonyl, N,N-[($C_6$–$C_{10}$)aryl]$_2$aminocarbonyl, N—($C_1$–$C_6$)alkyl-N—($C_6$–$C_{10}$)arylaminocarbonyl, ($C_6$–$C_{10}$)aryl, ($C_6$–$C_{10}$)aryloxy, ($C_1$–$C_6$)alkoxyaminocarbonyl or ($C_1$–$C_6$)alkyl-carbonylamino;

$R^3$ is hydrogen, halo, ($C_1$–$C_6$)alkyl, ($C_2$–$C_6$)alkenyl, ($C_2$–$C_6$)alkynyl, ($C_1$–$C_6$)alkoxy, ($C_1$–$C_6$)alkyl-(C=O)—, formyl, formamidyl, cyano, nitro, —CO$_2$H, ($C_1$–$C_6$)alkoxycarbonyl, aminocarbonyl, N—($C_1$–$C_6$)alkylaminocarbonyl, N,N-[($C_1$–$C_6$)alkyl]$_2$aminocarbonyl, N—($C_6$–$C_{10}$)arylaminocarbonyl, N,N—[($C_6$–$C_{10}$)aryl]$_2$aminocarbonyl, N—($C_1$–$C_6$)alkyl-N—($C_6$–$C_{10}$)arylaminocarbonyl, ($C_6$–$C_{10}$)aryl, ($C_6$–$C_{10}$)aryloxy, ($C_1$–$C_6$)alkoxyaminocarbonyl or ($C_1$–$C_6$)alkyl-carbonylamino;

wherein said $R^3$ ($C_1$–$C_6$)alkyl group may optionally be substituted with one to three substitutents independently selected from halo, hydroxy, ($C_1$–$C_6$)alkoxy, cyano, nitro, HO—(C=O)—, ($C_1$–$C_6$)alkoxycarbonyl, aminocarbonyl, N—($C_1$–$C_6$)alkylaminocarbonyl, N,N—[($C_1$–$C_6$)alkyl]$_2$aminocarbonyl, N—($C_6$–$C_{10}$)arylaminocarbonyl, N,N—[($C_6$–$C_{10}$)aryl]$_2$aminocarbonyl, N—($C_1$–$C_6$)alkyl-N—($C_6$–$C_{10}$)arylaminocarbonyl, ($C_6$–$C_{10}$)aryl, ($C_6$–$C_{10}$)aryloxy-($C_1$–$C_6$)alkoxyaminocarbonyl or ($C_1$–$C_6$)alkyl-carbonylamino;

$R^4$ is ($C_1$–$C_6$) alkyl optionally substituted by one to three halo atoms;

$R^5$ is hydrogen; halo; hydroxy; mercapto; ($C_1$–$C_6$)alkyl; ($C_1$–$C_6$)alkoxy optionally substituted with one to three halogen atoms; ($C_2$–$C_6$)alkenyl; ($C_2$–$C_6$)alkynyl; cyano; formyl; ($C_1$–$C_6$)alkylcarbonyl; ($C_1$–$C_6$)alkyl-C(=O)—O—; HO—(O=C)—; ($C_1$–$C_6$)alkoxy-C(=O)—; aminocarbonyl; N—($C_1$–$C_6$)alkylaminocarbonyl; N,N—[($C_1$–$C_6$)alkyl]$_2$aminocarbonyl; nitro; amino; ($C_1$–$C_6$)alkylamino; [($C_1$–$C_6$)alkyl]$_2$amino; or ($C_1$–$C_6$)alkyl-S—;

wherein said $R^5$ ($C_1$–$C_6$)alkyl group may optionally be substituted with one to three substitutents independently selected from halo, hydroxy, ($C_1$–$C_6$)alkoxy, cyano, nitro, amino, ($C_1$–$C_6$)alkylamino, ($C_1$–$C_6$)dialkylamino, HO—(O=C)—, ($C_1$–$C_6$)alkoxy-(C=O)—, aminocarbonyl, N—($C_1$–$C_6$)alkylaminocarbonyl, N,N—[($C_1$–$C_6$)alkyl]$_2$aminocarbonyl, N—($C_6$–$C_{10}$)arylaminocarbonyl, N,N—[($C_6$–$C_{10}$)aryl]$_2$aminocarbonyl, N—($C_1$–$C_6$)alkyl-N—($C_6$–$C_{10}$)arylaminocarbonyl, ($C_6$–$C_{10}$)aryl, ($C_6$–$C_{10}$)aryloxy, ($C_1$–$C_6$)alkoxyaminocarbonyl or ($C_1$–$C_6$)alkyl-carbonylamino;

$R^6$ is selected from the group consisting of:

(a) phenyl optionally substituted by 1–3 substituents independently selected from the group consisting of halo, hydroxy, cyano, mercapto, HO—(C=O)—, nitro, ($C_1$–$C_6$)alkyl, ($C_2$–$C_6$)alkenyl, ($C_1$–$C_6$)alkoxy, —OCF$_3$, ($C_1$–$C_6$)alkyl-S—, ($C_1$–$C_6$)alkyl-S(=O)—, ($C_1$–$C_6$)alkyl-SO$_2$—, amino, ($C_1$–$C_6$)alkylamino, di[($C_1$–$C_6$)alkyl]amino, H$_2$N—(C=O)—, ($C_1$–$C_6$)alkyl-NH—(C=O)—, di[($C_1$–$C_6$)alkyl]-N—(C=O)—, ($C_1$–$C_6$)alkyl-(C=O)—O—, ($C_1$–$C_6$)alkyl-(C=O)—N(R')—, formyl, $(C_1-C_6)$alkyl-$(C=O)$—, $(C_1-C_6)$alkoxy-$(C=O)$—, $(C_6-C_{10})$aryl and $(C_2-C_9)$heterocyclic; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—$(C=O)$—, nitro, $(C_1-C_6)$alkyl, $(C_2-C_6)$alkenyl, $(C_1-C_6)$alkoxy, $(C_1-C_6)$alkyl-S—, $(C_1-C_6)$alkyl-S$(=O)$—, $(C_1-C_6)$alkyl-SO$_2$—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-$(C=O)$—O—, $(C_1-C_6)$alkyl-$(C=O)$—N(R')—, formyl, $(C_1-C_6)$alkyl-$(C=O)$— and $(C_1-C_6)$alkoxy-$(C=O)$—; wherein R' is hydrogen or $(C_1-C_6)$alkyl;

(b) phenyl fused to a saturated, partially saturated or aromatic (5- to 7-membered)-carbocyclic ring; wherein either of said phenyl or said fused saturated, partially saturated or aromatic (5- to 7-membered) carbocyclic ring is optionally substituted by 1 to 2 substituents per ring, wherein said substituents are independently selected from the group consisting of halo, hydroxy, cyano, mercapto, HO—$(C=O)$—, nitro, $(C_1-C_6)$alkyl, $(C_2-C_6)$alkenyl, $(C_2-C_6)$alkynyl, $(C_1-C_6)$alkoxy, —OCF$_3$, $(C_1-C_6)$alkyl-S—, $(C_1-C_6)$alkyl-S$(=O)$—, $(C_1-C_6)$alkyl-SO$_2$—, amino, $(C_1-C_6)$alkylamino, di[$(C_1-C_6)$alkyl]amino, $H_2N$—$(C=O)$—, $(C_1-C_6)$alkyl-NH—$(C=O)$—, di[$(C_1-C_6)$alkyl]-N—$(C=O)$—, $(C_1-C_6)$alkyl-$(C=O)$—O—, $(C_1-C_6)$alkyl-$(C=O)$—N(R')—, formyl, $(C_1-C_6)$alkyl-$(C=O)$—, $(C_1-C_6)$alkoxy-$(C=O)$—, $(C_6-C_{10})$aryl and; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—$(C=O)$—, nitro, $(C_1-C_6)$alkyl, $(C_2-C_6)$alkenyl, $(C_1-C_6)$alkoxy, $(C_1-C_6)$alkyl-S—, $(C_1-C_6)$alkyl-S$(=O)$—, $(C_1-C_6)$alkyl-SO$_2$—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-$(C=O)$—O—, $(C_1-C_6)$alkyl-$(C=O)$—N(R')—, formyl, $(C_1-C_6)$alkyl-$(C=O)$— and $(C_1-C_6)$alkoxy-$(C=O)$—; wherein R' is hydrogen or $(C_1-C_6)$alkyl;

(c) (5- to 7-membered)-carbocyclic optionally containing one or two double bonds; wherein said (5- to 7-membered)-carbocyclic may also be optionally substituted by 1–3 substituents independently selected from the group consisting of halo, hydroxy, cyano, mercapto, HO—$(C=O)$—, nitro, $(C_1-C_6)$alkyl, $(C_2-C_6)$alkenyl, $(C_2-C_6)$alkynyl, $(C_1-C_6)$alkoxy, —OCF$_3$, $(C_1-C_6)$alkyl-S—, $(C_1-C_6)$alkyl-S$(=O)$—, $(C_1-C_6)$alkyl-SO$_2$—, amino, $(C_1-C_6)$alkylamino, di[$(C_1-C_6)$alkyl]amino, $H_2N$—$(C=O)$—, $(C_1-C_6)$alkyl-NH—$(C=O)$—, di[$(C_1-C_6)$alkyl]-N—$(C=O)$—, $(C_1-C_6)$alkyl-$(C=O)$—O—, $(C_1-C_6)$alkyl-$(C=O)$—N(R')—, formyl, $(C_1-C_6)$alkyl-$(C=O)$—, $(C_1-C_6)$alkoxy-$(C=O)$—, $(C_6-C_{10})$aryl; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—$(C=O)$—, nitro, $(C_1-C_6)$alkyl, $(C_2-C_6)$alkenyl, $(C_1-C_6)$alkoxy, $(C_1-C_6)$alkyl-S—, $(C_1-C_6)$alkyl-S$(=O)$—, $(C_1-C_6)$alkyl-SO$_2$—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-$(C=O)$—O—, $(C_1-C_6)$alkyl-$(C=O)$—N(R')—, formyl, $(C_1-C_6)$alkyl-$(C=O)$— and $(C_1-C_6)$alkoxy-$(C=O)$—; wherein R' is hydrogen or $(C_1-C_6)$alkyl;

(d) (5- to 7-membered)-carbocyclic fused to a saturated, partially saturated or aromatic (5- to 7-membered)-carbocyclic ring; wherein said (5- to 7-membered)-carbocyclic may optionally contain one or two double bonds; wherein either of said (5- to 7-membered)-carbocyclic or said fused saturated, partially saturated or aromatic (5- to 7-membered)-carbocyclic ring is optionally substituted by 1 to 2 substituents per ring, wherein said substituents are independently selected from the group consisting of halo, hydroxy, cyano, mercapto, HO—$(C=O)$—, nitro, $(C_1-C_6)$alkyl, $(C_2-C_6)$alkenyl, $(C_2-C_6)$alkynyl, $(C_1-C_6)$alkoxy, —OCF$_3$, $(C_1-C_6)$alkyl-S—, $(C_1-C_6)$alkyl-S$(=O)$—, $(C_1-C_6)$alkyl-SO$_2$—, amino, $(C_1-C_6)$alkylamino, di[$(C_1-C_6)$alkyl]amino, $H_2N$—$(C=O)$—, $(C_1-C_6)$alkyl-NH—$(C=O)$—, di[$(C_1-C_6)$alkyl]-N—$(C=O)$—, $(C_1-C_6)$alkyl-$(C=O)$—O—, $(C_1-C_6)$alkyl-$(C=O)$—N(R')—, formyl, $(C_1-C_6)$alkyl-$(C=O)$—, $(C_1-C_6)$alkoxy-$(C=O)$—, $(C_6-C_{10})$aryl and; wherein R' is hydrogen or $(C_1-C_6)$alkyl; wherein each of said $(C_1-C_6)$alkyl is optionally substituted with 1 to 3 substituents independently selected from the group consisting of halo, hydroxy, cyano, mercapto, HO—$(C=O)$—, nitro, $(C_1-C_6)$alkyl, $(C_2-C_6)$alkenyl, $(C_1-C_6)$alkoxy, $(C_1-C_6)$alkyl-S—, $(C_1-C_6)$alkyl-S$(=O)$—, $(C_1-C_6)$alkyl-SO$_2$—, amino, $(C_1-C_6)$alkylamino, di[$(C_1-C_6)$alkyl]amino, amido, $(C_1-C_6)$alkylamido, di[$(C_1-C_6)$alkyl]amido, $(C_1-C_6)$alkyl-$(C=O)$—O—, $(C_1-C_6)$alkyl-$(C=O)$—N(R')—, formyl, $(C_1-C_6)$alkyl-$(C=O)$— and $(C_1-C_6)$alkoxy-$(C=O)$—; wherein R' is hydrogen or $(C_1-C_6)$alkyl;

$R^8$ is hydrogen; halo; hydroxy; mercapto; $(C_1-C_6)$alkyl; $(C_1-C_6)$alkoxy optionally substituted with one to three halogen atoms; $(C_2-C_6)$alkenyl; $(C_2-C_6)$alkynyl; cyano; formyl; $(C_1-C_6)$alkylcarbonyl; $(C_1-C_6)$alkyl-C$(=O)$—O—; HO—$(O=C)$—; $(C_1-C_6)$alkoxy-C$(=O)$—; aminocarbonyl; N—$(C_1-C_6)$alkylaminocarbonyl; N,N—[$(C_1-C_6)$alkyl]$_2$ aminocarbonyl; nitro; amino; $(C_1-C_6)$alkylamino; di[$(C_1-C_6)$alkyl]amino; or $(C_1-C_6)$alkyl-S—;

wherein said $R^8$ $(C_1-C_6)$alkyl group may optionally be substituted with one to three substituents independently selected from halo, hydroxy, $(C_1-C_6)$alkoxy, cyano, nitro, HO—$(O=C)$—, $(C_1-C_6)$alkoxy-C$(=O)$—, aminocarbonyl, N—$(C_1-C_6)$alkylaminocarbonyl, N,N—[$(C_1-C_6)$alkyl]$_2$ aminocarbonyl, N—$(C_6-C_{10})$arylaminocarbonyl, N,N—[$(C_6-C_{10})$aryl]$_2$aminocarbonyl, N—$(C_1-C_6)$alkyl-N—$(C_6-C_{10})$arylaminocarbonyl, $(C_6-C_{10})$aryl, $(C_6-C_{10})$aryloxy, $(C_2-C_9)$heteroaryl, $(C_2-C_9)$heteroaryloxy, morpholino-carbonyl, $(C_1-C_6)$alkoxyaminocarbonyl or $(C_1-C_6)$alkyl-carbonylamino;

and a pharmaceutically acceptable salt thereof.

2. A compound according to claim 1 wherein said compound has the formula

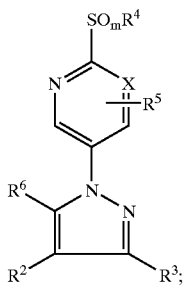

IA1 wherein X is CR$^8$ and m is 2.

3. A compound according to claim 1 wherein said compound has the formula

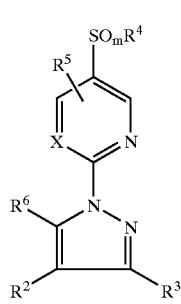

IA2 wherein X is CR$^8$ and m is 2.

4. A compound according to claim 1 wherein R$^6$ is phenyl optionally substituted by 1–3 substituents independently selected from the group consisting of halo, hydroxy, cyano, mercapto, HO—(C=O)—, nitro, (C$_1$–C$_6$)alkyl, (C$_2$–C$_6$)alkenyl, (C$_1$–C$_6$)alkoxy, —OCF$_3$, (C$_1$–C$_6$)alkyl-S—, (C$_1$–C$_6$)alkyl-(S=O)—, (C$_1$–C$_6$)alkyl-SO$_2$—, (C$_1$–C$_6$)alkylsulfonylamino, amino, (C$_1$–C$_6$)alkylamino, di[(C$_1$–C$_6$)alkyl]amino, H$_2$N—(C=O), (C$_1$–C$_6$)alkyl-HN—(C=O)—, di[(C$_1$–C$_6$)alkyl]-N—(C=O)—, (C$_1$–C$_6$)alkyl-(C=O)—O—, (C$_1$–C$_6$)alkyl-(C=O)—N(R')—, formyl, (C$_1$–C$_6$)alkyl-(C=O)—, (C$_1$–C$_6$)alkoxy-(C=O)—, (C$_6$–C$_{10}$)aryl; wherein R' is hydrogen or (C$_1$–C$_6$)alkyl; wherein each of said (C$_1$–C$_6$)alkyl is optionally substituted with 1 to 3 substituents independently selected from the group consisting of halo, hydroxy, cyano, mercapto, HO—(C=O)—, nitro, (C$_1$–C$_6$)alkyl, (C$_2$–C$_6$)alkenyl, (C$_1$–C$_6$)alkoxy, (C$_1$–C$_6$)alkyl-S—, amino, (C$_1$–C$_6$)alkylamino, di[(C$_1$–C$_6$)alkyl]amino, amido, (C$_1$–C$_6$)alkylamido, di[(C$_1$–C$_6$)alkyl]amido, (C$_1$–C$_6$)alkyl-(C=O)—O—, (C$_1$–C$_6$)alkyl-(C=O)—N(R')—, formyl, (C$_1$–C$_6$)alkyl-(C=O)— and (C$_1$–C$_6$)alkoxy-(C=O)—: wherein R' is hydrogen or (C$_1$–C$_6$)alkyl.

5. A compound according to claim 1 wherein R$^6$ is phenyl fused to a saturated, partially saturated or aromatic (5- to 7-membered)-carbocyclic ring; wherein either of said phenyl or said fused saturated, partially saturated or aromatic (5- to 7-membered)-carbocyclic ring is optionally substituted by 1 to 2 substituents per ring, wherein said substituents are independently selected from the group consisting of halo, hydroxy, cyano, mercapto, HO—(C=O)—, nitro, (C$_1$–C$_6$)alkyl, (C$_2$–C$_6$)alkenyl, (C$_2$–C$_6$)alkynyl, (C$_1$–C$_6$)alkoxy, —OCF$_3$, (C$_1$–C$_6$)alkyl-S—, (C$_1$–C$_6$)alkyl-(S=O)—, (C$_1$–C$_6$)alkyl-SO$_2$—, (C$_1$–C$_6$)alkylsulfonylamino, amino, (C$_1$–C$_6$)alkylamino, di[(C$_1$–C$_6$)alkyl]amino, H$_2$N—(C=O), (C$_1$–C$_6$)alkyl-HN—(C=O)—, di[(C$_1$–C$_6$)alkyl]-N—(C=O)—, (C$_1$–C$_6$)alkyl- (C=O)—O—, (C$_1$–C$_6$)alkyl-(C=O)—N(R')—, formyl, (C$_1$–C$_6$)alkyl-(C=O)—, (C$_1$–C$_6$)alkoxy-(C=O)—, (C$_6$–C$_{10}$)aryl and; wherein R' is hydrogen or (C$_1$–C$_6$)alkyl; wherein each of said (C$_1$–C$_6$)alkyl is optionally substituted with 1 to 3 substituents independently selected from the group consisting of halo, hydroxy, cyano, mercapto, HO—(C=O)—, nitro, (C$_1$–C$_6$)alkyl, (C$_2$–C$_6$)alkenyl, (C$_1$–C$_6$)alkoxy, (C$_1$–C$_6$)alkyl-S—, amino, (C$_1$–C$_6$)alkylamino, di[(C$_1$–C$_6$)alkyl]amino, amido, (C$_1$–C$_6$)alkylamido, di[(C$_1$–C$_6$)alkyl]amido, (C$_1$–C$_6$)alkyl-(C=O)—O—, (C$_1$–C$_6$)alkyl-(C=O)—N(R')—, formyl, (C$_1$–C$_6$)alkyl-(C=O)— and (C$_1$–C$_6$)alkoxy-(C=O)—; wherein R' is hydrogen or (C$_1$–C$_6$)alkyl.

6. A compound according to claim 1 wherein R$^6$ is (5- to 7-membered)-carbocyclic optionally containing one or two double bonds; wherein said (5- to 7-membered)-carbocyclic may also be optionally substituted by 1–3 substituents independently selected from the group consisting of halo, hydroxy, cyano, mercapto, HO—(C=O)—, nitro, (C$_1$–C$_6$)alkyl, (C$_2$–C$_6$)alkenyl, (C$_2$–C$_6$)alkynyl, (C$_1$–C$_6$)alkoxy, —OCF$_3$, (C$_1$–C$_6$)alkyl-S—, (C$_1$–C$_6$)alkyl-(S=O)—, (C$_1$–C$_6$)alkyl-SO$_2$—, (C$_1$–C$_6$)alkylsulfonylamino, amino, (C$_1$–C$_6$)alkylamino, di[(C$_1$–C$_6$)alkyl]amino, H$_2$N—(C=O), (C$_1$–C$_6$)alkyl-HN—(C=O)—, di[(C$_1$–C$_6$)alkyl]-N—(C=O)—, (C$_1$–C$_6$)alkyl-(C=O)—O—, (C$_1$–C$_6$)alkyl-(C=O)—N(R')—, formyl, (C$_1$–C$_6$)alkyl-(C=O)—, (C$_1$–C$_6$)alkoxy-(C=O)—, (C$_6$–C$_{10}$)aryl; wherein R' is hydrogen or (C$_1$–C$_6$)alkyl; wherein each of said (C$_1$–C$_6$)alkyl is optionally substituted with 1 to 3 substituents independently selected from the group consisting of halo, hydroxy, cyano, mercapto, HO—(C=O)—, nitro, (C$_1$–C$_6$)alkyl, (C$_2$–C$_6$)alkenyl, (C$_1$–C$_6$)alkoxy, (C$_1$–C$_6$)alkyl-S—, amino, (C$_1$–C$_6$)alkylamino, di[(C$_1$–C$_6$)alkyl]amino, amido, (C$_1$–C$_6$)alkylamido, di[(C$_1$–C$_6$)alkyl]amido, (C$_1$–C$_6$)alkyl-(C=O)—O—, (C$_1$–C$_6$)alkyl-(C=O)—N(R')—, formyl, (C$_1$–C$_6$)alkyl-(C=O)— and (C$_1$–C$_6$)alkoxy-(C=O)—; wherein R' is hydrogen or (C$_1$–C$_6$)alkyl.

7. A compound according to claim 1 wherein R$^6$ is (5- to 7-membered)-carbocyclic fused to a saturated, partially saturated or aromatic (5- to 7-membered)-carbocyclic ring; wherein said (5- to 7-membered)-carbocyclic may optionally contain one or two double bonds; wherein either of said (5- to 7-membered)-carbocyclic or said fused saturated, partially saturated or aromatic (5- to 7-membered)-carbocyclic ring is optionally substituted by 1 to 2 substituents per ring, wherein said substituents are independently selected from the group consisting of halo, hydroxy, cyano, mercapto, HO—(C=O)—, nitro, (C$_1$–C$_6$)alkyl, (C$_2$C$_6$)alkenyl, (C$_2$–C$_6$)alkynyl, (C$_1$–C$_6$)alkoxy, —OCF$_3$, (C$_1$–C$_6$)alkyl-S—, (C$_1$–C$_6$)alkyl-(S=O)—, (C$_1$–C$_6$)alkyl-SO$_2$—, (C$_1$–C$_6$)alkylsulfonylamino, amino, (C$_1$–C$_6$)alkylamino, di[(C$_1$–C$_6$)alkyl]amino, H$_2$N—(C=O), (C$_1$–C$_6$)alkyl-HN—(C=O)—, di[(C$_1$–C$_6$)alkyl]-N—(C=O)—, (C$_1$–C$_6$)alkyl-(C=O)—O—, (C$_1$–C$_6$)alkyl-(C=O)—N(R')—, formyl, (C$_1$–C$_6$)alkyl-(C=O)—, (C$_1$–C$_6$)alkoxy-(C=O)—, (C$_6$–C$_{10}$)aryl; wherein R' is hydrogen or (C$_1$–C$_6$)alkyl; wherein each of said (C$_1$–C$_6$)alkyl is optionally substituted with 1 to 3 substituents independently selected from the group consisting of halo, hydroxy, cyano, mercapto, HO—(C=O)—, nitro, (C$_1$–C$_6$)alkyl, (C$_2$–C$_6$)alkenyl, (C$_1$–C$_6$)alkoxy, (C$_1$–C$_6$)alkyl-S—, amino, (C$_1$–C$_6$)alkylamino, di[(C$_1$–C$_6$)alkyl]amino, amido, (C$_1$–C$_6$)alkylamido, di[(C$_1$–C$_6$)alkyl]amido, (C$_1$–C$_6$)alkyl-(C=O)—O—, (C$_1$–C$_6$)alkyl-(C=O)—N(R')—, formyl, (C$_1$–C$_6$)alkyl-(C=O)— and (C$_1$–C$_6$)alkoxy-(C=O)—; wherein R' is hydrogen or (C$_1$–C$_6$)alkyl.

8. A compound according to claim 1 wherein R$^2$ is hydrogen, halo or (C$_1$–C$_6$)alkyl.

9. A compound according to claim 1 wherein $R^2$ is methyl or hydrogen.

10. A compound according to claim 1 wherein $R^3$ is cyano or $(C_1-C_6)$alkyl optionally substituted with one to three halo atoms.

11. A compound according to claim 1 wherein $R^3$ is —$CF_3$ or —$CF_2H$.

12. A compound according to claim 1 wherein said compound is selected from the group consisting of:

2-[5-(4-Bromo-phenyl)-3-trifluoromethyl-pyrazol-1-yl]-5-methanesulfonyl-pyridine;
{4-[2-(6-Methanesulfonyl-pyridin-3-yl)-5-trifluoromethyl-2H-pyrazol-3-yl]-phenyl}- dimethyl-amine;
{4-[2-(5-Methanesulfonyl-pyridin-2-yl)-5-trifluoromethyl-2H-pyrazol-3-yl]-phenyl}-dimethyl-amine;
2-[3-Difluoromethyl-5-(3-fluoro-4-methoxy-phenyl)-pyrazol-1-yl]-5-methanesulfonyl-pyridine;
2-[5-(3-Bromo-4-methoxy-phenyl)-3-trifluoromethyl-pyrazol-1-yl]-5-methanesulfonyl-pyridine;
2-[5-(3-Chloro-4-methoxy-phenyl)-3-trifluoromethyl-pyrazol-1-yl]-5-methanesulfonyl-pyridine;
2-(3-Difluoromethyl-5-p-tolyl-pyrazol-1-yl)-5-methanesulfonyl-pyridine;
5-Methanesulfonyl-2-(5-o-tolyl-3-trifluoromethyl-pyrazol-1-yl)-pyridine;
5-Methanesulfonyl-2-(5-phenyl-3-trifluoromethyl-pyrazol-1-yl)-pyridine;
2-[5-(3-Chloro-4-methoxy-phenyl)-3-difluoromethyl-pyrazol-1-yl]-5-methanesulfonyl-pyridine;
2-[5-(3-Fluoro-4-methoxy-phenyl)-3-trifluoromethyl-pyrazol-1-yl]-5-methanesulfonyl-pyridine;
5-Methanesulfonyl-2-[5-(4-methoxy-3-methyl-phenyl)-3-trifluoromethyl-pyrazol-1-yl]-pyridine;
2-[3-Difluoromethyl-5-(4-methoxy-3-methyl-phenyl)-pyrazol-1-yl]-5-methanesulfonyl-pyridine;
2-[5-(2-Fluoro-4-methoxy-phenyl)-3-trifluoromethyl-pyrazol-1-yl]-5-methanesulfonyl-pyridine;
2-[3-Difluoromethyl-5-(2-fluoro-4-methoxy-phenyl)-pyrazol-1-yl]-5-methanesulfonyl-pyridine;
2-[3-Difluoromethyl-5-(3,4-dimethyl-phenyl)-pyrazol-1-yl]-5-methanesulfonyl-pyridine;
2-[5-(4-Chloro-phenyl)-3-trifluoromethyl-pyrazol-1-yl]-5-methanesulfonyl-pyridine;
2-[5-(4-Fluoro-phenyl)-3-trifluoromethyl-pyrazol-1-yl]-5-methanesulfonyl-pyridine;
2-[5-(4-Chloro-3-methyl-phenyl)-3-trifluoromethyl-pyrazol-1-yl]-5-methanesulfonyl-pyridine;
2-(3-Difluoromethyl-5-phenyl-pyrazol-1-yl)-5-methanesulfonylpyridine;
2-[3-Difluoromethyl-5-(4-fluoro-phenyl)-pyrazol-1-yl]-5-methanesulfonyl-pyridine;
5-Methanesulfonyl-2-[5-(6-methyl-naphthalen-2-yl)-3-trifluoromethyl-pyrazol-1-yl]-pyridine;
2-(5-Cyclohexyl-3-difluoromethyl-pyrazol-1-yl)-5-methanesulfonyl-pyridine;
2-[3-Difluoromethyl-5-(2-fluoro-phenyl)-pyrazol-1-yl]-5-methanesulfonyl-pyridine;
2-(4-Chloro-5-phenyl-3-trifluoromethyl-pyrazol-1-yl)-5-methanesulfonyl-pyridine; and
2-(5-Cyclohexyl-3-trifluoromethyl-pyrazol-1-yl)-5-methanesulfonyl-pyridine.

* * * * *